US011642395B2

(12) United States Patent
Charles, III et al.

(10) Patent No.: US 11,642,395 B2
(45) Date of Patent: May 9, 2023

(54) MODIFIED FIBROBLAST GROWTH FACTOR 21 (FGF-21) FOR USE IN METHODS FOR TREATING NONALCOHOLIC STEATOHEPATITIS (NASH)

(71) Applicant: BRISTOL-MYERS SQUIBB COMPANY, Princeton, NJ (US)

(72) Inventors: Edgar Davidson Charles, III, Westfield, NJ (US); Rose C. Christian, Hopewell, NJ (US); Yi Luo, Southampton, PA (US)

(73) Assignee: BRISTOL-MYERS SQUIBB COMPANY, Princeton, NJ (US)

( * ) Notice: Subject to any disclaimer, the term of this patent is extended or adjusted under 35 U.S.C. 154(b) by 205 days.

(21) Appl. No.: 16/644,839

(22) PCT Filed: Sep. 6, 2018

(86) PCT No.: PCT/US2018/049729
§ 371 (c)(1),
(2) Date: Mar. 5, 2020

(87) PCT Pub. No.: WO2019/051073
PCT Pub. Date: Mar. 14, 2019

(65) Prior Publication Data
US 2021/0106653 A1    Apr. 15, 2021

Related U.S. Application Data

(60) Provisional application No. 62/640,211, filed on Mar. 8, 2018, provisional application No. 62/571,960, filed on Oct. 13, 2017, provisional application No. 62/556,179, filed on Sep. 8, 2017.

(51) Int. Cl.
A61K 38/18     (2006.01)
A61P 1/16      (2006.01)
A61K 45/06     (2006.01)
G01N 33/68     (2006.01)

(52) U.S. Cl.
CPC .......... A61K 38/1825 (2013.01); A61K 45/06 (2013.01); A61P 1/16 (2018.01); G01N 33/6887 (2013.01); G01N 2333/78 (2013.01); G01N 2800/085 (2013.01)

(58) Field of Classification Search
CPC ....... A61K 38/1825; A61K 45/06; A61P 1/16; G01N 33/6887; G01N 2333/78; G01N 2800/085
See application file for complete search history.

(56) References Cited

U.S. PATENT DOCUMENTS 3,710,795 A     1/1973   Higuchi et al.
4,863,457 A     9/1989   Lee
4,904,584 A     2/1990   Shaw
5,218,092 A     6/1993   Sasaki et al.
5,501,856 A     3/1996   Ohtori et al.
6,716,626 B1    4/2004   Itoh et al.
8,012,931 B2    9/2011   Cujec et al.
8,383,365 B2    2/2013   Cujec et al.
9,079,971 B2    7/2015   Cujec et al.
9,434,778 B2    9/2016   Morin et al.
9,517,273 B2    12/2016  Cujec et al.
9,631,004 B2    4/2017   Morin et al.
9,975,936 B2    5/2018   Cujec et al.
10,189,883 B2 * 1/2019   Morin ................ C07K 14/50
10,377,805 B2   8/2019   Cujec et al.
10,377,806 B2   8/2019   Morin et al.
(Continued)

FOREIGN PATENT DOCUMENTS

CN    103923207 A    7/2014
EP       430539 A2   6/1991
(Continued)

OTHER PUBLICATIONS

Leeming D.J., et al. "Estimation of serum "true collagen type III formation" (Pro-C3) levels as a marker of non-alcoholic steatohepatitis in a prospective cohort," Poster Presentations: Posters Thursday, Apr. 20, 2017: Fatty liver disease: Clinical aspects, [online] [Nov. 2, 2021] Online site: <https://www.infona.pl/resource/bwmeta1.element.elsevier-abdb6528-b727-38ds-8503-356d7ecd5389>).
Abdelmalek M F: "Baseline serum PRO-C3 predicts response to BMS-986036 (PEG-FGF21): A secondary analysis of a multi-center clinical trial in non-alcoholic steatohepatitis (NASH)", Database accession No. EMB-618936642 & Hepatology, vol. 66 (Supplement 1):3 pages (2017).
Anonymous: "Bristol Myers Squibb's BMS-986036 (Pegylated FGF21) Shows Consistent Improvement in Liver Fat, Liver Injury and Fibrosis in Patients with Nonalcoholic Steatohepati-tis (NASH) in Phase 2 Trial," Bristol-Myers Squibb, 5 pages (2017) Retrieved from the Internet: URL:https://news.bms.com/press-release/bmy/bristol-myers-squibbs-oms-986036-pegylated-fgf21-shows-consistent-improvement-live [retrieved on Nov. 26, 2018].
(Continued)

Primary Examiner — Marcela M Cordero Garcia
(74) Attorney, Agent, or Firm — Nelson Mullins Riley & Scarborough LLP; Jane E. Remillard, Esq.; Jill Gorny Sloper, Esq.

(57) ABSTRACT

Provided herein are methods for treating a patient having NASH who has been determined to have a particular threshold level of serum Pro-C3 (e.g., greater than 10 ng/ML) by administering to the patient a modified Fibroblast growth factor 21 (FGF-21) in an amount and with a frequency sufficient to treat NASH. Also provided are methods for monitoring responsiveness of a patient having NASH to treatment with a modified FGF-21, the method comprising: determining the serum Pro-C3 level in a blood sample from the patient obtained during or after treatment, wherein: a decreased serum Pro-C3 level in the blood sample from the patient obtained during or after treatment, as compared to the serum Pro-C3 level in a blood sample from the patient obtained prior to treatment with the modified FGF-21, indicates that the patient is responsive to treatment with the modified FGF-21.

16 Claims, 13 Drawing Sheets

Specification includes a Sequence Listing.

(56) References Cited

U.S. PATENT DOCUMENTS

| | | | |
|---|---|---|---|
| 10,624,913 B2* | 4/2020 | Schentag | A61K 9/2059 |
| 10,961,291 B2 | 3/2021 | Cujec et al. | |
| 11,248,031 B2 | 2/2022 | Morin et al. | |
| 2001/0012628 A1 | 8/2001 | Agarwal et al. | |
| 2002/0164713 A1 | 11/2002 | Itoh et al. | |
| 2004/0185494 A1 | 9/2004 | Itoh et al. | |
| 2004/0259780 A1 | 12/2004 | Glasebrook et al. | |
| 2005/0037457 A1 | 2/2005 | Itoh et al. | |
| 2005/0176631 A1 | 8/2005 | Heuer et al. | |
| 2007/0293430 A1 | 12/2007 | Frye et al. | |
| 2008/0241223 A1 | 10/2008 | Nivaggioli et al. | |
| 2011/0172401 A1 | 7/2011 | Cujec et al. | |
| 2013/0150564 A1 | 6/2013 | Cujec et al. | |
| 2015/0273075 A1 | 10/2015 | Cujec et al. | |
| 2017/0096463 A1 | 4/2017 | Cujec et al. | |
| 2017/0189486 A1 | 7/2017 | Morin et al. | |
| 2018/0243375 A1 | 8/2018 | Morin et al. | |
| 2018/0298073 A1 | 10/2018 | Cujec et al. | |
| 2019/0382460 A1 | 12/2019 | Morin et al. | |
| 2020/0031894 A1 | 1/2020 | Cujec et al. | |
| 2021/0261637 A1 | 8/2021 | Cujec et al. | |
| 2022/0185856 A1 | 6/2022 | Morin et al. | |

FOREIGN PATENT DOCUMENTS

| | | | |
|---|---|---|---|
| EP | 488401 A1 | 6/1992 | |
| WO | 99/03887 A1 | 1/1999 | |
| WO | 99/67291 A2 | 12/1999 | |
| WO | 00/26354 A1 | 5/2000 | |
| WO | 01/18172 A2 | 3/2001 | |
| WO | 01/36640 A2 | 5/2001 | |
| WO | 03/011213 A2 | 2/2003 | |
| WO | 03/059270 A2 | 7/2003 | |
| WO | 04/110472 A2 | 12/2004 | |
| WO | 05/061712 A1 | 7/2005 | |
| WO | 05/072769 A1 | 8/2005 | |
| WO | 2005/091944 A2 | 10/2005 | |
| WO | 05/113606 A2 | 12/2005 | |
| WO | 06/028595 A2 | 3/2006 | |
| WO | 06/028714 A1 | 3/2006 | |
| WO | 06/050247 A2 | 5/2006 | |
| WO | 06/065582 A2 | 6/2006 | |
| WO | 06/078463 A2 | 7/2006 | |
| WO | 2008/121563 A2 | 10/2008 | |
| WO | 09/149171 A2 | 12/2009 | |
| WO | 10/042747 A2 | 4/2010 | |
| WO | 11/154349 A2 | 12/2011 | |
| WO | 2012/066075 A1 | 5/2012 | |
| WO | 13/052311 A1 | 4/2013 | |
| WO | 13/188181 A1 | 12/2013 | |
| WO | 2016/065326 A2 | 4/2016 | |
| WO | WO2016/065326 * | 4/2016 | A61K 38/00 |
| WO | 2017/046181 A1 | 3/2017 | |
| WO | 2017/074117 A1 | 5/2017 | |
| WO | 2017/083276 A1 | 5/2017 | |

OTHER PUBLICATIONS

Charles, E. D. et al., "Multi-biomarker validation of MRI-pdf and mre-derived treatment response with BMS-986036 (PEG-FGF21): A secondary analysis of a multi-center clinical trial in non-alcoholic steatohepatitis (NASH)," Database accession No. EMB-618935379 & Hepatology, vol. 66 (Supplement 1):2 pages (2017).

International Preliminary Report on Patentability, PCT/US2018/049729, dated Mar. 10, 2020, 9 pages.

International Search Report and Written Opinion, PCT/US2018/049729, dated Dec. 17, 2018, 15 pages.

Levin, J. et al., "BMS-986036 (pegylated FGF21) in patients with non-alcoholic steatohepatitis: A phase 2 study", The International Liver Congress, 9 pages (2017) URL:http://natap.org/2017/EASL/EASL_33.htm [retrieved on Nov. 22, 2018].

Sanyal A. et al., "BMS-986036 (pegylated FGF21) in patients with non-alcoholic steatohepatitis: a phase 2 study," Journal of Hepatology, vol. 66(1):Abstract LBO-02, 2 pages (2017).

Argo CK, et al., "Epidemiology and Natural History of Non-Alcoholic Steatohepatitis ," Clin. Liver Dis., vol. 13:511-531 (2009).

Asano T, et al., "Adiponectin knockout mice on high fat diet develop fibrosing steatohepatitis," J Gastroenterol Hepatol., vol. 24(10): 1669-1676 (2009).

Baird et al., "The Fibroblast Growth Factor Family an Overview," NYAS, xi-xii(1991).

Bao X, et al., "Developmental Changes of Col3a1 mRNA Expression in Muscle and Their Association with Intramuscular Collagen in Pigs," J Genet Genomics., vol. 34:223-228 (2007).

Bedogni G, et al., "The Fatty Liver Index: A Simple and Accurate Predictor of Hepatic Steatosis in the General Population ," BMC Gastroenterol., vol. 6: 33 (2006).

Boyle MP, et al., "Development and Validation of the Collagen Neo-Epitope Biomarker Pro-C3 "FIB-C3 Score" for Detection and Staging of Advanced Non-Alcoholic Fatty Liver Disease in a Large International Multi-Centre Patient Cohort," Hepatology, vol. 66(Suppl 1): 54A : 2 pages (2017).

Bristol-Myers Squibb Press Release, Oct. 20, 2017, 25 pages.

Burgess, W. H. et al., "The Heparin-Binding (Fibroblast) Growth Factor Family of Proteins ," Annu. Rev. Biochem. , vol. 58:575-606 (1989).

Charles E, et al., "A Phase 1 Study of BMS-986036 (Pegylated FGF21) in Healthy Obese Subjects," Hepatology, vol. 64(Suppl 1): 546A : 1 page (2016).

Charles E, et al., "A Phase 2 Study of BMS-986036 (Pegylated FGF21) in Obese Adults with Type 2 Diabetes and a High Prevalence of Fatty Liver," Hepatology, vol. 64(Suppl 1): 17A : 1 page (2016).

Charlton M, et al., "Serum Pro-C3 (N-terminal propeptide of type III procollagen) is associated with hepatic steatosis and fibrosis and responsive to changes in steatosis in patients with NASH," Hepatology, vol. 66(Suppl 1): 1180A : 2 pages (2017).

Cohen JC, et al., "Human Fatty Liver Disease: Old Questions and New Insights Science ," vol. 332:1519-1523 (2011).

Coskun T, et al.,"Fibroblast Growth Factor 21 Corrects Obesity in Mice," Endocrinology, vol. 149(12): 6018-6027 (2008).

Cote et al., "Generation of Human Monoclonal Antibodies Reactive With Cellular Antigens," Proc Natl Acad Sci USA, vol. 80:2026-2030 (1983).

Daniels R, et al., "Serum Pro-C3 combined with clinical parameters is superior to established serological fibrosis tests at identifying patients with advanced fibrosis among patients with non-alcoholic fatty liver disease," J Hepatol., vol. 66 (Suppl 1):S671: 1 page (2017).

Fang F, et al., "The adipokine adiponectin has potent anti-fibrotic effects mediated via adenosine monophosphate-activated protein kinase: novel target for fibrosis therapy," Arthritis Res Ther vol. 14(5): R229 (2012).

Gaich G, et al., "The Effects of LY2405319, an FGF21 Analog, in Obese Human Subjects With Type 2 Diabetes " Cell. Metab., vol. 18(3): 333-340 (2013).

Gupta S, et al., "Collagen turnover biomarkers distinguish healthy from NAFLD patients and aid identification of patients with evidence of histologically active NASH," Hepatology, vol. 66(Suppl 1): 1097A : 1 page (2017).

Harlow and Lane, "Antibodies: A Laboratory Manual," Cold Spring Harbor Laboratory: Cold Spring Harbor, NY, 2page, (1988).

Haschek W, et al. "Evaluation of Cutaneous Toxicity" In: Fundamentals of Toxicologic Pathology. Second ed. Academic Press, Chapter 7: 156 (2009).

Hassan, K. et al., "Nonalcoholic Fatty Liver Disease: A Comprehensive Review of a Growing Epidemic ," World J. Gastroenterol., vol. 20(34):12082-12101 (2014).

Jensen LT, et al., "Collagen: Scaffold for Repair or Execution ," Cardiovasc Res., vol. 33:535-539 (1997).

Karsdal MA, et al., "Fibrogenesis Assessed by Serological Type III Collagen Formation Identifies Patients With Progressive Liver Fibrosis and Responders to a Potential Antifibrotic Therapy ," Am J Physiol Gastrointest Liver Physiol., vol. 311(6): G1009-17 (2016).

(56) References Cited

OTHER PUBLICATIONS

Karsdal, A. et al., "Pro-C3, a novel serum marker of pure fibrogenesis, identifies patients with progressive liver fibrosis and responders to anti-fibrotic therapy", Hepatology, vol. 64(Suppl 1): 209A : 1 page (2016).

Kharitonenkov A, et al.,"The Metabolic State of Diabetic Monkeys Is Regulated by Fibroblast Growth Factor-21," Endocrinology, vol. 148(2): 774-781 (2007).

Kharitonenkov, A. et al., "FGF-21 as a Novel Metabolic Regulator," J Clin Invest., vol. 115(6):1627-35 (2005).

Kim AM, et al., "Once-weekly Administration of a Long-Acting Fibroblast Growth Factor 21 Analogue Modulates Lipids, Bone Turnover Markers, Blood Pressure and Body Weight Differently in Obese People With Hypertriglyceridaemia and in Non-Human Primates," Diabetes Obes Metabol., vol. 19(12): 1762-72 (2017).

Kohler and Milstein, "Continuous Cultures of Fused Cells Secreting Antibody of Predefined Specificity," Nature, vol. 256:495-497 (1975).

Kozbor, D. et al., "Specific Immunoglobulin Production and Enhanced Tumorigenicity Following Ascites Growth of Human Hybridomas," J Immunol Methods 81:31-42 (1985).

Krupinski, J. et al., "Effects of BMS-986036 (pegylated fibroblast growth factor 21) on hepatic steatosis and fibrosis in a mouse model of nonalcoholic steatohepatitis", Hepatology, vol. 64(Suppl 1): 749A : 1 page (2016).

Kumar P, et al., "Adiponectin Agonist ADP355 Attenuates CCl4-induced Liver Fibrosis in Mice," PLoS One, vol. 9(10): e110405 (2014).

Le TA, et al., "Effect of Colesevelam on Liver Fat Quantified by Magnetic Resonance in Nonalcoholic Steatohepatitis: A Randomized Controlled Trial," Hepatology, vol. 56(3): 922-32 (2012).

Leeming DJ, et al., "Pro-C3 in combination with clinical parameters is associated with severity of histological features of non-alcoholic steatohepatitis and fibrosis," Hepatology, vol. 66(Suppl 1): 1107A: 2 pages (2017).

Leeming DJ, et al., "Plasma collagen III type III (PRO-C3) levels associate with severity of histological features of non-alcoholic steatohepatitis and fibrosis within the screening population from the CENTAUR study," NASH Biomarkers Workshop 2017; Presented on Saturday, May 5, 2017, 18 pages.

Leeming DJ, et al., ,"Estimation of serum"true collagen type III formation"(Pro-C3) levels as a marker of non-alcoholic steatohepatitisin a prospective cohort," J Hepatol., vol. 66(Suppl 1): Abstract S154: 1 page (2017).

Loomba R, et al., "Longitudinal changes in liver stiffness by magnetic rresonancee lastography (MRE), liverfibrosis, and serum markers of fibrosis in a multi-center clinical trial in nonalcoholic steatohepatitis(NASH)," J Hepatol., vol. 66(Suppl 1):S671: 1 page (2017).

Loomba R, et al., "Multi-Biomarker Validation of MRI-PDFF and MRE-Derived Treatment Response With BMS-986036 (peg-FGF21): A Secondary Analysis of a Multi-center Clinical Trial in Non-Alcoholic Steatohepatitis (NASH)," Hepatology, vol. 66(Suppl 1): 333A: 1 page (2017).

Luo Y, et al., " BMS-986036, a PEGylated fibroblast growth factor 21 analogue, reduces fibrosis and Pro-C3 in a mouse model of non-alcoholic steatohepatitis," J Hepatol., vol. 66(Suppl 1):S396: 2 pages (2017).

Luo Y, et al., "Improvement of fibrosis is associated with the decrease of collagen III formation biomarker Pro-C3 in patients with non-alcoholic steatohepatitis," Hepatology, vol. 66(Suppl 1): 345A : 1 page (2017).

Luo Y., et al., "Collagen formation and degradation biomarkers identify advanced fibrosisin NASH patients," J Hepatol., vol. 66(Suppl 1): S676: 2 pages (2017).

McKeehan, W. et al., "The Heparan Sulfate-Fibroblast Growth Factor Family: Diversity of Structure and Function," Prog. Nucleic Acid Res. Mol. Biol., vol. 59:135-176 (1998).

Neuschwander-Tetri, BA, Nonalcoholic Steatohepatitis and the Metabolic Syndrome,: Am. J. Med. Sci., vol. 330:326-335 (2005).

Nielsen MJ, "Markers of Collagen Remodeling Detect Clinically Significant Fibrosis in Chronic Hepatitis C Patients" PLoS One, vol. 10(9): e0137302, 12 pages (2015).

Nielsen, M. et al., "The Neo-Epitope Specific PRO-C3 ELISA Measures True Formation of Type III Collagen Associated With Liver and Muscle Parameters," Am J Transl Res., vol. 5(3): 303-315 (2013).

Nielsen, M. et al., "Plasma Pro-C3 (N-terminal type III collagen propeptide) predicts fibrosis progression in patients with chronic hepatitis C," Liver International 35:429-437 (2015).

Nishimura et al., "Identification of a novel FGF, FGF-21, preferentially expressed in the liver1," Biochimica et Biophysica Acta, 1492:203-206 (2000).

Ornitz and Itoh, "Fibroblast Growth Factors" Genome Biology 2001, 2(3):reviews 3005.1-3005.12 (2001).

Pagano C, et al. "Plasma Adiponectin Is Decreased in Nonalcoholic Fatty Liver Disease," Eur. J. Endocrinol., vol. 152 (1): 113-118 (2005).

Patel J, et al., "Association of Noninvasive Quantitative Decline in Liver Fat Content on MRI With Histologic Response in Nonalcoholic Steatohepatitis," Therap. Adv. Gastroenterol., vol. 9(5): 692-701 (2016).

Patel NS, et al., "Effect of Weight Loss on Magnetic Resonance Imaging Estimation of Liver Fat and Volume in Patients With Nonalcoholic Steatohepatitis," Clin Gastroenterol Hepatol., vol. 13(3): 561-8 (2015).

Reuss et al., "Fibroblast Growth Factors and Their Receptors in the Central Nervous System," Cell Tissue Res., vol. 313:139-157 (2003).

Sanyal A, et al., "Pegbelfermin (BMS-986036), a PEGylated fibroblast growth factor 21 analogue, in patients with non-alcoholic steatohepatitis: a randomised, double-blind, placebo-controlled, phase 2a trial," Lancet, vol. 392: 2705-2717 (2018).

Sanyal A, et al., "BMS-986036 (pegylated FGF21) in patients with non-alcoholic steatohepatitis: a phase 2 study," J Hepatol., vol. 66(Suppl 1):S89: 2 pages (2017).

Sanyal AJ, et al., "BMS-986036 (pegylated FGF21) in patients with non-alcoholic steatohepatitis: A phase 2 study," Hepatology, vol. 66(Suppl 1): 104A : 2 pages (2017).

Shafiei MS et al., "Adiponectin Regulation of Stellate Cell Activation via PPARgamma-dependent and -Independent Mechanisms," Am J Pathol., vol. 178(6): 2690-2699 (2011).

Susanne Schuster and Ariel E. Feldstein, "NASH: Novel Therapeutic Strategies Targeting ASK1 in NASH," Nature Reviews Gastroenterology & Hepatology, vol. 14: 329-330 (2017).

Talukdar S, et al., "A Long-Acting FGF21 Molecule, PF-05231023, Decreases Body Weight and Improves Lipid Profile in Non-human Primates and Type 2 Diabetic Subjects," Cell Metab., vol. 23(3): 427-40 (2016).

Wei W, et al., "Fibroblast Growth Factor 21 Promotes Bone Loss by Potentiating the Effects of Peroxisome Proliferator-Activated Receptor gamma," Proc Natl Acad Sci USA, vol. 109(8): 3143-3148 (2012).

Xu A, et al., "The Fat-Derived Hormone Adiponectin Alleviates Alcoholic and Nonalcoholic Fatty Liver Diseases in Mice," J. Clin. Invest., vol. 112(1): 91-100 (2003).

Xu J, et al., "Acute Glucose-Lowering and Insulin-Sensitizing Action of FGF21 in Insulin-Resistant Mouse Models—Association With Liver and Adipose Tissue Effects ," Am J Physiol Endocrinol Metab., vol. 297(5): E1105-14 (2009).

Younes R, et al., "Insulin secretion and decreased glucose clearance are associated with enhanced fibrogenesis and a high risk of disease progression in non-diabetic patients with Non Alcoholic Fatty Liver Disease," Hepatology, vol. 66(Suppl 1): 1135A : 2 pages (2017).

Younossi ZM, et al., "Changes in the Prevalence of the Most Common Causes of Chronic Liver Diseases in the United States From 1988 to 2008," Clin. Gastroenterol. Hepatol., vol. 9:524-530 (2011).

Zhang, H. et al., "Phosphoprotein Analysis Using Antibodies Broadly Reactive Against Phosphorylated Motifs," J Biol Chem 277:39379-39387 (2002).

Abdelmalek, Manal F. et al., "Baseline Serum Pro-C3 Predicts Response to BMS-986036 (PEG-FGF21): A Secondary Analysis of

(56) References Cited

OTHER PUBLICATIONS a Multi-Center Clinical Trial in Non-Alcoholic Steatohepatitis (NASH)," The Liver Meeting, American Association for the Study of Liver Diseases (AASLD 2017), Washington, DC, Oct. 20-24, 2017, 1 page.

Edgar D. C. M.D., "PEG FGF21 Translating Science to Clinical Trials," PEG-FGF21 Global NASH Congress 2018 (Presented Feb. 27, 2018) 41 pages.

Luo, Y. et al., "Serum Metabolomics Analysis to Identify Biomarkers for Advanced Fibrosis in NASH Patients," The International Liver Congress' 2018: Annual Meeting of the European Association for the Study of the Liver. Paris, France, Apr. 11-15, 2018, Poster FRI-454, 1 page.

Shi, B. et al., "Clinical value of hepatic fibrosis parameters and serum ferritin in obese children with nonalcoholic fatty liver disease," Zhejiang Da Xue Xue Bao Yi Xue Ban, vol. 37(3): 245-249 (2008).

* cited by examiner

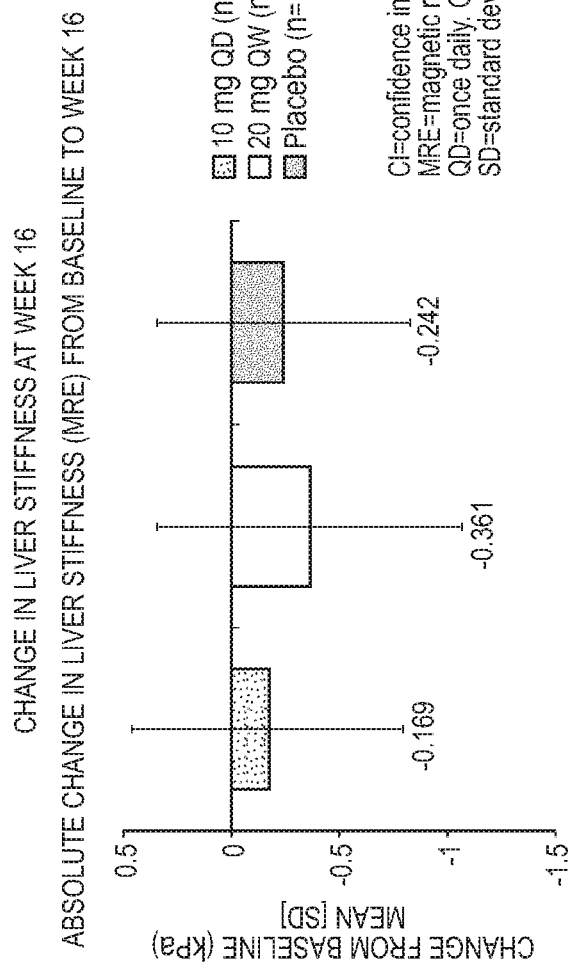
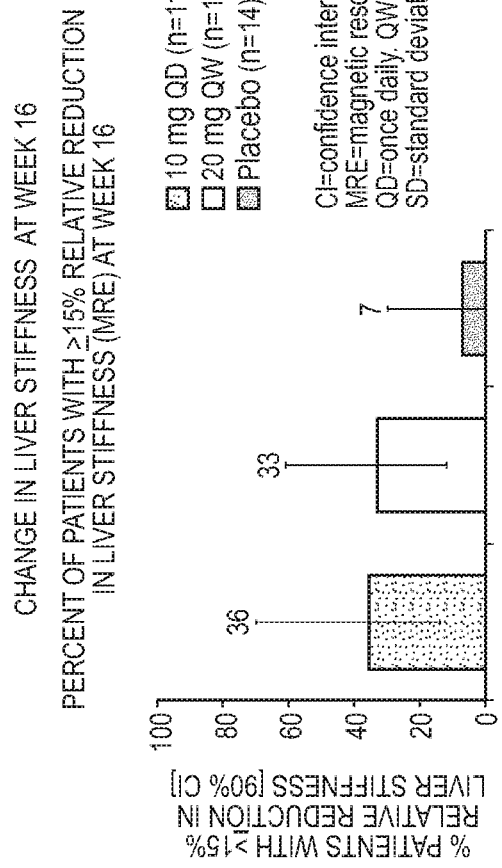

MODIFIED FIBROBLAST GROWTH FACTOR 21 (FGF-21) FOR USE IN METHODS FOR TREATING NONALCOHOLIC STEATOHEPATITIS (NASH)

RELATED APPLICATIONS

This application is a 35 U.S.C. 371 national stage filing of International Application No. PCT/US2018/049729, filed on Sep. 6, 2018, which claims the benefit of priority of U.S. Provisional Application Nos. 62/556,179 (filed on Sep. 8, 2017), 62/571,960 (filed on Oct. 13, 2017) and 62/640,211 (filed on Mar. 8, 2018). The contents of the aforementioned applications are hereby incorporated by reference in their entireties.

SEQUENCE LISTING

The instant application contains a Sequence Listing which has been submitted electronically in ASCII format and is hereby incorporated by reference in its entirety. Said ASCII copy, created on Mar. 5, 2020, is named MXI-609US_Sequence_Listing.txt and is 4,058 bytes in size.

BACKGROUND

Nonalcoholic fatty liver disease (NAFLD) has become one of the major diseases plaguing the nation and world. In the United States, NAFLD is the most common cause of liver disease, representing over 75% of the chronic liver disease (see, e.g., Younossi Z M, et al., Clin. Gastroenterol. Hepatol., 2011; 9:524-530). It also is one of the most common indications for liver transplantation, contributing a major burden to both the morbidity and mortality of the nation.

The spectrum of NAFLD is a continuum ranging from simple steatosis to Nonalcoholic Steatohepatitis (NASH) and finally cirrhosis. The defining characteristic of the disease is the presence of greater than normal lipid deposition within the liver with the absence of excessive alcohol consumption defined as >20 g/d for men and 10 g/d for women. Steatosis is the presence of lipid within the cytoplasm of hepatocytes, the criteria for which is defined in the literature as being either hepatic lipid levels above the 95th percentile for healthy individuals (about >55 mg/g liver) (see Cohen J C, et al., Science. 2011; 332:1519-1523), greater than 5% of the liver's weight (see, Kareem Hassan, et al., World J. Gastroenterol. 2014 Sep. 14; 20(34): 12082-12101), or found in greater than 5% of hepatocytes histologically (see Neuschwander-Tetri B A, *Am. J. Med. Sci.* 2005; 330:326-335).

The progression of steatosis to NASH is a frequently encountered clinical scenario, associated with worse outcomes for patients. A key-defining feature of the NASH is the presence of inflammation and subsequent fibrosis. Specifically, NASH is defined as steatosis in the presence of hepatocyte damage, inflammation and/or subsequent scarring and replacement of the tissue with type I collagen. Approximately 10%-29% of patients with NASH will develop cirrhosis within a 10 year period (Argo C K, et al., Clin. Liver Dis. 2009; 13:511-531). NASH can also lead to liver cancer. Currently, no pharmacological therapies are approved for the treatment of NASH (see Susanne Schuster and Ariel E. Feldstein, Nature Reviews Gastroenterology & Hepatology 14, 329-330 (5 Apr. 2017).

Accordingly, the following disclosure provides a novel method of treating NASH using a modified FGF-21, criteria that allow for optimization of the treatment, and methods for monitoring the progression and abatement of NASH.

SUMMARY

Provided herein are methods for treating a patient having NASH by administering to the patient a modified Fibroblast growth factor 21 (FGF-21) if the patient has a particular serum threshold level (e.g., greater than 10 ng/ML, 15 ng/ML, or 20 ng/ML) of the biomarker, Pro-C3.

In one embodiment, a method for treating a patient having NASH is provided, the method comprising: (a) determining the serum Pro-C3 level in a blood sample from the patient and (b) administering to the patient a modified FGF-21 in an amount and with a frequency sufficient to treat NASH, if the serum Pro-C3 level prior to administration to the patient of the modified FGF-21 is greater than about 10 ng/ML.

In another embodiment, a method for treating a patient having NASH who has been determined to have a serum Pro-C3 level greater than about 10 ng/ML is provided, the method comprising administering to the patient a modified FGF-21 in an amount and with a frequency sufficient to treat NASH.

In another embodiment, a method for treating a patient with NASH with modified FGF-21 is provided, wherein the patient has a serum Pro-C3 level greater than 10 ng/ML prior to treatment, wherein the method comprises administering to the patient a modified FGF-21 in an amount and with a frequency sufficient to treat NASH.

In another embodiment, a method for treating a patient having NASH is provided, wherein the method comprises: (1) obtaining or having obtained a blood sample from the patient, (2) determining or having determined a serum Pro-C3 level in the blood sample that is greater than 10 ng/ML, and (3) administering to the patient a modified FGF-21 in an amount and with a frequency sufficient to treat NASH after a serum Pro-C3 level has been determined.

Also provided are methods for monitoring responsiveness of a patient having NASH to treatment with a modified FGF-21, the method comprising: determining the serum Pro-C3 level in a blood sample from the patient obtained during or after treatment, wherein: a decreased serum Pro-C3 level in the blood sample from the patient obtained during or after treatment, as compared to the serum Pro-C3 level in a blood sample from the patient obtained prior to treatment with the modified FGF-21, indicates that the patient is responsive to treatment with the modified FGF-21.

In one embodiment, the patient having NASH has been determined to have or is determined to have a particular threshold level of Pro-C3 that warrants treatment with a modified FGF-21. In one embodiment, the patient has a serum Pro-C3 level that is greater than 10 ng/ML. In one embodiment, the patient has a serum Pro-C3 level that is greater than 11 ng/ML. In one embodiment, the patient has a serum Pro-C3 level that is greater than 12 ng/ML. In one embodiment, the patient has a serum Pro-C3 level that is greater than 13 ng/ML. In one embodiment, the patient has a serum Pro-C3 level that is greater than 14 ng/ML. In one embodiment, the patient has a serum Pro-C3 level that is greater than 15 ng/ML. In one embodiment, the patient has a serum Pro-C3 level that is greater than 16 ng/ML. In one embodiment, the patient has a serum Pro-C3 level that is greater than 17 ng/ML. In one embodiment, the patient has a serum Pro-C3 level that is greater than 18 ng/ML. In one embodiment, the patient has a serum Pro-C3 level that is greater than 19 ng/ML. In one embodiment, the patient has a serum Pro-C3 level that is greater than 20 ng/ML. In one embodiment, the patient has a serum Pro-C3 level that is greater than 21 ng/ML. In one embodiment, the patient has a serum Pro-C3 level that is greater than 22 ng/ML. In one embodiment, the patient has a serum Pro-C3 level that is greater than 23 ng/ML. In one embodiment, the patient has a serum Pro-C3 level that is greater than 24 ng/ML. In one embodiment, the patient has a serum Pro-C3 level that is greater than 25 ng/ML.

In another embodiment, the patient has a serum Pro-C3 level between 10 ng/ML and 25 ng/ML. In another embodiment, the patient has a serum Pro-C3 level between 10 ng/ML and 20 ng/ML. In another embodiment, the patient has a serum Pro-C3 level between 10 ng/ML and 15 ng/ML. In another embodiment, the patient has a serum Pro-C3 level between 12 ng/ML and 20 ng/ML. In another embodiment, the patient has a serum Pro-C3 level between 12 ng/ML and 15 ng/ML. In another embodiment, the patient has a serum Pro-C3 level between 15 ng/ML and 25 ng/ML. In another embodiment, the patient has a serum Pro-C3 level between 15 ng/ML and 20 ng/ML.

Expression levels Pro-C3 can be measured by quantitation of protein and/or RNA levels in a biological sample from the patient (e.g., blood or a blood fraction) using any suitable technique. In one embodiment, expression levels are measured by quantitation of protein and/or RNA levels, using at least one of an immunoassay, immunochemistry assay, immunohistochemistry assay, nucleoprobe assay, in situ hybridization, fluorescent RNA probes, RT-PCR, microarray transcription assay, and/or RNA transcription assay. In another embodiment, expression levels are measured using an immunoassay (e.g., an enzyme-linked immunosorbent assay (ELISA) or a radioimmunoassay (RIA)), e.g. the ELISA described in Nielsen et al., Am J Transl Res 2013; 5(3):303-315. Pro-C3 level or levels may be measured by an FDA-approved test.

Any suitable modified FGF-21 can be used in the method described herein. In one embodiment, the modified FGF-21 comprises the polypeptide of SEQ ID NO:1, except that an amino acid in the polypeptide is substituted by a non-naturally encoded amino acid, wherein: (a) said non-naturally encoded amino acid is at a position corresponding to residue 108 of SEQ ID NO:1; (b) said non-naturally encoded amino acid comprises para-acetyl phenylalanine linked to a polymer comprising a poly(ethylene glycol). In another embodiment, the poly(ethylene glycol) has an average molecular weight of about 30 kDa. In another embodiment, the modified FGF-21 comprises the polypeptide of SEQ ID NO:1 except that the amino acid at position 108 of SEQ ID NO:1 is substituted by a non-naturally encoded amino acid, wherein: (a) said non-naturally encoded amino acid comprises para-acetyl phenylalanine, and (b) said non-naturally encoded amino acid is linked to a polymer comprising a poly(ethylene glycol) having an average molecular weight of about 30 kDa. In another embodiment, the non-naturally encoded amino acid is linked to said polymer through an oxime linkage. In another embodiment, the modified FGF-21 comprises SEQ ID NO:2. In some embodiment, the para-acetyl phenylalanine in SEQ ID NO:2 is linked to a polymer comprising a poly(ethylene glycol). In some embodiment, the poly(ethylene glycol) has an average molecular weight of about 30 kDa.

In another embodiment a method for treating a patient having NASH is provided, comprising: (a) determining the serum Pro-C3 level in a blood sample from the patient and (b) administering to the patient a modified FGF-21 in an amount and with a frequency sufficient to treat NASH, if the serum Pro-C3 level prior to administration to the patient of a modified FGF-21 is greater than about 10 ng/ML (e.g. greater than about 11 ng/ML, about 12 ng/ML, about 13 ng/ML, about 14 ng/ML, about 15 ng/ML, about 16 ng/ML, about 17 ng/ML, about 18 ng/ML, about 19 ng/ML, about 20 ng/ML, about 21 ng/ML, about 22 ng/ML, about 23 ng/ML, about 24 ng/ML, or about 25 ng/ML), wherein the modified FGF-21 comprises the polypeptide of SEQ ID NO:1, except that an amino acid in the polypeptide is substituted by a non-naturally encoded amino acid, wherein: (a) said non-naturally encoded amino acid is at a position corresponding to residue 108 of SEQ ID NO:1; and (b) said non-naturally encoded amino acid comprises para-acetyl phenylalanine linked to a polymer comprising a poly(ethylene glycol).

In another embodiment a method for treating a patient having NASH is provided, comprising: (a) determining the serum Pro-C3 level in a blood sample from the patient and (b) administering to the patient a modified FGF-21 in an amount and with a frequency sufficient to treat NASH, if the serum Pro-C3 level prior to administration to the patient of a modified FGF-21 is greater than about 10 ng/ML (e.g., greater than about 11 ng/ML, about 12 ng/ML, about 13 ng/ML, about 14 ng/ML, about 15 ng/ML, about 16 ng/ML, about 17 ng/ML, about 18 ng/ML, about 19 ng/ML, about 20 ng/ML, about 21 ng/ML, about 22 ng/ML, about 23 ng/ML, about 24 ng/ML, or about 25 ng/ML), wherein the modified FGF-21 comprises the polypeptide of SEQ ID NO:1 except that the amino acid at position 108 of SEQ ID NO:1 is substituted by a non-naturally encoded amino acid, wherein: (a) said non-naturally encoded amino acid comprises para-acetyl phenylalanine, and (b) said non-naturally encoded amino acid is linked to a polymer comprising a poly(ethylene glycol) having an average molecular weight of about 30 kDa.

In another embodiment, a method for treating a patient having NASH is provided, comprising: (a) determining the serum Pro-C3 level in a blood sample from the patient and (b) administering to the patient a modified FGF-21 in an amount and with a frequency sufficient to treat NASH, if the serum Pro-C3 level prior to administration to the patient of a modified FGF-21 is greater than about 10 ng/ML (e.g. greater than about 11 ng/ML, about 12 ng/ML, about 13 ng/ML, about 14 ng/ML, about 15 ng/ML, about 16 ng/ML, about 17 ng/ML, about 18 ng/ML, about 19 ng/ML, about 20 ng/ML, about 21 ng/ML, about 22 ng/ML, about 23 ng/ML, about 24 ng/ML, or about 25 ng/ML), wherein the modified FGF-21 consists of or comprises SEQ ID NO:2. In some embodiment, the para-acetyl phenylalanine in SEQ ID NO:2 is linked to a polymer comprising a poly(ethylene glycol). In some embodiments, the poly(ethylene glycol) has an average molecular weight of about 30 kDa.

In another embodiment, a method for treating a patient having NASH who has been determined to have a serum Pro-C3 level greater than about 10 ng/ML is provided, the method comprising administering to the patient a modified FGF-21 in an amount and with a frequency sufficient to treat NASH, wherein the modified FGF-21 comprises the polypeptide of SEQ ID NO:1, except that an amino acid in the polypeptide is substituted by a non-naturally encoded amino acid, wherein: (a) said non-naturally encoded amino acid is at a position corresponding to residue 108 of SEQ ID NO:1; and (b) said non-naturally encoded amino acid comprises para-acetyl phenylalanine linked to a polymer comprising a poly(ethylene glycol).

In another embodiment, a method for treating a patient having NASH who has been determined to have a serum Pro-C3 level greater than about 10 ng/ML is provided, the method comprising administering to the patient a modified FGF-21 in an amount and with a frequency sufficient to treat NASH, wherein the modified FGF-21 comprises the polypeptide of SEQ ID NO:1 except that the amino acid at position 108 of SEQ ID NO:1 is substituted by a non-naturally encoded amino acid, wherein: (a) said non-naturally encoded amino acid comprises para-acetyl phenylalanine, and (b) said non-naturally encoded amino acid is linked to a polymer comprising a poly(ethylene glycol) having an average molecular weight of about 30 kDa. In another embodiment, a method for treating a patient having NASH who has been determined to have a serum Pro-C3 level greater than about 10 ng/ML is provided, the method comprising administering to the patient a modified FGF-21 in an amount and with a frequency sufficient to treat NASH, wherein the modified FGF-21 consists of or comprises SEQ ID NO:2. In some embodiments, the para-acetyl phenylalanine in SEQ ID NO:2 is linked to a polymer comprising a poly(ethylene glycol). In some embodiments, the poly(ethylene glycol) has an average molecular weight of about 30 kDa.

In some embodiments described herein, the patient having NASH has been determined to have a serum Pro-C3 level greater than about 11 ng/ML, about 12 ng/ML, about 13 ng/ML, about 14 ng/ML, about 15 ng/ML, about 16 ng/ML, about 17 ng/ML, about 18 ng/ML, about 19 ng/ML, about 20 ng/ML, about 21 ng/ML, about 22 ng/ML, about 23 ng/ML, about 24 ng/ML, or about 25 ng/ML.

In another embodiment, a method for monitoring responsiveness of a patient having NASH to treatment with a modified FGF-21 is provided, the method comprising: determining the serum Pro-C3 level in a blood sample from the patient obtained during or after treatment, wherein: a decreased serum Pro-C3 level in the blood sample from the patient obtained during or after treatment, as compared to the serum Pro-C3 level in a blood sample from the patient obtained prior to treatment with the modified FGF-21, indicates that the patient is responsive to treatment with the modified FGF-21, wherein the modified FGF-21 comprises the polypeptide of SEQ ID NO:1, except that an amino acid in the polypeptide is substituted by a non-naturally encoded amino acid, wherein: (a) said non-naturally encoded amino acid is at a position corresponding to residue 108 of SEQ ID NO:1; and (b) said non-naturally encoded amino acid comprises para-acetyl phenylalanine linked to a polymer comprising a poly(ethylene glycol)

In another embodiment, a method for monitoring responsiveness of a patient having NASH to treatment with a modified FGF-21 is provided, the method comprising: determining the serum Pro-C3 level in a blood sample from the patient obtained during or after treatment, wherein: a decreased serum Pro-C3 level in the blood sample from the patient obtained during or after treatment, as compared to the serum Pro-C3 level in a blood sample from the patient obtained prior to treatment with the modified FGF-21, indicates that the patient is responsive to treatment with the modified FGF-21, wherein the modified FGF-21 comprises the polypeptide of SEQ ID NO:1 except that the amino acid at position 108 of SEQ ID NO:1 is substituted by a non-naturally encoded amino acid, wherein: (a) said non-naturally encoded amino acid comprises para-acetyl phenylalanine, and (b) said non-naturally encoded amino acid is linked to a polymer comprising a poly(ethylene glycol) having an average molecular weight of about 30 kDa.

In another embodiment, a method for monitoring responsiveness of a patient having NASH to treatment with a modified FGF-21 is provided, the method comprising: determining the serum Pro-C3 level in a blood sample from the patient obtained during or after treatment, wherein: a decreased serum Pro-C3 level in the blood sample from the patient obtained during or after treatment, as compared to the serum Pro-C3 level in a blood sample from the patient obtained prior to treatment with the modified FGF-21, indicates that the patient is responsive to treatment with the modified FGF-21, wherein the modified FGF-21 consists of or comprises SEQ ID NO:2. In some embodiments, the para-acetyl phenylalanine in SEQ ID NO:2 is linked to a polymer comprising a poly(ethylene glycol). In some embodiments, the poly(ethylene glycol) has an average molecular weight of about 30 kDa.

In one embodiment, the modified FGF-21 is administered at a fixed dose. In one embodiment, the modified FGF-21 is administered at a fixed daily or weekly dose.

In one embodiment, a method for treating a patient having NASH is provided, the method comprising administering to the patient a modified FGF-21 at 10 mg once daily to treat NASH, wherein the modified FGF-21 comprises the polypeptide of SEQ ID NO:1 except that the amino acid at position 108 of SEQ ID NO:1 is substituted by a non-naturally encoded amino acid, wherein: (a) said non-naturally encoded amino acid comprises para-acetyl phenylalanine, and (b) said non-naturally encoded amino acid is linked to a polymer comprising a poly(ethylene glycol) having an average molecular weight of about 30 kDa.

In one embodiment, a method for treating a patient having NASH is provided, the method comprising administering to the patient a modified FGF-21 at 20 mg once weekly to treat NASH, wherein the modified FGF-21 comprises the polypeptide of SEQ ID NO:1 except that the amino acid at position 108 of SEQ ID NO:1 is substituted by a non-naturally encoded amino acid, wherein: (a) said non-naturally encoded amino acid comprises para-acetyl phenylalanine, and (b) said non-naturally encoded amino acid is linked to a polymer comprising a poly(ethylene glycol) having an average molecular weight of about 30 kDa.

In another embodiment, the modified FGF-21 is administered at a dose of about 10 mg once weekly. In another embodiment, the modified FGF-21 is administered at a dose of about 11 mg once weekly. In another embodiment, the modified FGF-21 is administered at a dose of about 12 mg once weekly. In another embodiment, the modified FGF-21 is administered at a dose of about 13 mg once weekly. In another embodiment, the modified FGF-21 is administered at a dose of about 14 mg once weekly. In another embodiment, the modified FGF-21 is administered at a dose of about 15 mg once weekly. In another embodiment, the modified FGF-21 is administered at a dose of about 16 mg once weekly. In another embodiment, the modified FGF-21 is administered at a dose of about 17 mg once weekly. In another embodiment, the modified FGF-21 is administered at a dose of about 18 mg once weekly. In another embodiment, the modified FGF-21 is administered at a dose of about 19 mg once weekly. In another embodiment, the modified FGF-21 is administered at a dose of about 20 mg once weekly. In another embodiment, the modified FGF-21 is administered at a dose of about 21 mg once weekly. In another embodiment, the modified FGF-21 is administered at a dose of about 22 mg once weekly. In another embodiment, the modified FGF-21 is administered at a dose of about 23 mg once weekly. In another embodiment, the modified FGF-21 is administered at a dose of about 24 mg once weekly. In another embodiment, the modified FGF-21 is administered at a dose of about 25 mg once weekly. In another embodiment, the modified FGF-21 is administered at a dose of about 26 mg once weekly. In another embodiment, the modified FGF-21 is administered at a dose of about 27 mg once weekly. In another embodiment, the modified FGF-21 is administered at a dose of about 28 mg once weekly. In another embodiment, the modified FGF-21 is administered at a dose of about 29 mg once weekly. In another embodiment, the modified FGF-21 is administered at a dose of about 30 mg once weekly.

In another embodiment, the modified FGF-21 is administered at a fixed daily dose. In another embodiment, the modified FGF-21 is administered at a dose of about 5 mg once daily. In another embodiment, the modified FGF-21 is administered at a dose of about 10 mg once daily. In another embodiment, the modified FGF-21 is administered at a dose of about 11 mg once daily. In another embodiment, the modified FGF-21 is administered at a dose of about 12 mg once daily. In another embodiment, the modified FGF-21 is administered at a dose of about 13 mg once daily. In another embodiment, the modified FGF-21 is administered at a dose of about 14 mg once daily. In another embodiment, the modified FGF-21 is administered at a dose of about 15 mg once daily. In another embodiment, the modified FGF-21 is administered at a dose of about 16 mg once daily. In another embodiment, the modified FGF-21 is administered at a dose of about 17 mg once daily. In another embodiment, the modified FGF-21 is administered at a dose of about 18 mg once daily. In another embodiment, the modified FGF-21 is administered at a dose of about 19 mg once daily. In another embodiment, the modified FGF-21 is administered at a dose of about 20 mg once daily.

The modified FGF-21 can be administered according to the methods described herein alone or in combination with one or more additional therapeutic agents. In some embodiments, the one or more additional therapeutic agents may be selected from anti-fibrotic agents, N-cadherin antagonist, anti-N cadherin antibody, small molecule N-cadherin antagonist, antagonistic N-cadherin fragment, anti-inflammatory agents, hepatoprotective agents suppressing renin-angiotensin system (RAS) system, probiotics, and polyunsaturated fatty acids (PUFAs). In some embodiments, the anti-fibrotic agent may be selected from nintedanib, Pirfenidone, LPA1 antagonists, LPA1 receptor antagonists, GLP1 analog, tralokinumab (IL-13, AstraZeneca), vismodegib (hedgehog antagonist, Roche), PRM-151 (pentraxin-2, TGF beta-1, Promedior), SAR-156597 (bispecific Mab IL-4&IL-13, Sanofi), simtuzumab (anti-lysyl oxidase-like 2 (anti-LOXL2) antibody, Gilead), CKD-942, PTL-202 (PDE inh./pentoxifylline/NAC oral control. release, Pacific Ther.), omipalisib (oral PI3K/mTOR inhibitor, GSK), IW-001 (oral sol. bovine type V collagen mod., ImmuneWorks), STX-100 (integrin alpha V/beta-6 ant. Stromedix/Biogen), Actimmune (IFN gamma), PC-SOD (midismase; inhaled, LTT Bio-Pharma/CKD Pharm), lebrikizumab (anti-IL-13 SC humanized mAb, Roche), AQX-1125 (SH1P1 activator, Aquinox), CC-539 (JNK inhibitor, Celgene), FG-3019 (FibroGen), and SAR-100842 (Sanofi). In some embodiments, the hepatoprotective agent may be ursodeoxycholic acid (UDCA) or obeticholic acid (OCA or INT-747, Intercept).

In one embodiment, the modified FGF-21 is administered first in time and the one or more additional active agents are administered second in time. In some embodiments, the one or more additional active agents are administered first in time and the modified FGF-21 is administered second in time.

In one embodiment, the treatment methods described herein result in a decrease in Pro-C3 levels in a patient. In another embodiment, the treatment methods described herein produce a shift toward normal levels of Pro-C3 in a patient. In another embodiment, the treatment methods described herein result in a reduction in liver stiffness in a patient, as assessed by magnetic resonance elastography (MRE). For example, in one embodiment, treatment with a modified FGF-21 results in a reduction in liver stiffness in the patient compared to the patient's liver stiffness prior to treatment, wherein liver stiffness is assessed by MRE. In another embodiment, treatment with a modified FGF-21 results in a 15% or greater (e.g., 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 50%, 55%, 60%, 65%, 70%, 75% or greater) reduction in liver stiffness in the patient compared to the patient's liver stiffness prior to treatment, wherein liver stiffness is assessed by MRE.

In another embodiment, the treatment methods described herein result in a reduction in hepatic fat fraction in a patient. For example, in one embodiment, treatment with a modified FGF-21 results in a reduction in hepatic fat fraction in the patient compared to the patient's hepatic fat fraction prior to treatment, wherein hepatic fat fraction is as assessed by magnetic resonance imaging-estimated proton density fat fraction (MRI-PDFF). In another embodiment, treatment with the modified FGF-21 results in a 30% or greater (e.g., 31%, 32%, 33%, 34%, 35%, 36%, 37%, 38%, 39%, 40%, 41%, 42%, 43%, 44%, 45%, 46%, 47%, 48%, 49% 50%, 51%, 52%, 53%, 54%, 55%, 56%, 57%, 58%, 59%, 60%, 65%, 70%, 75% or greater) reduction in hepatic fat fraction in the patient compared to the patient's hepatic fat fraction prior to treatment, wherein hepatic fat fraction is assessed by MRI-PDFF.

In another embodiment, the treatment methods described herein result in a reduction in live stiffness, a reduction in hepatic fat fraction, and/or a decrease in serum Pro-C3 levels in a patient. In another embodiment, treatment with a modified FGF-21 results in a reduction in liver stiffness in the patient compared to the patient's liver stiffness prior to treatment, and a decrease in serum Pro-C3 levels in the patient compared to the patient's serum Pro-C3 levels prior to treatment, wherein liver stiffness is assessed by MRE, and wherein the patient has been determined to have a serum Pro-C3 level greater than 10, 15 or 20 ng/ML prior to treatment with the modified FGF-21.

In another embodiment, the treatment methods described herein produces at least one therapeutic effect in a patient selected from the group consisting of a reduction or cessation in fatigue, malaise, weight loss, and/or right upper quadrant abdominal discomfort in the patient.

Also provided herein is a modified FGF-21 for use in the methods described herein. In one embodiment, a modified FGF-21 for use in a method of treating NASH in a patient is provided, wherein the method comprises administering to the patient a modified FGF-21 in an amount and with a frequency sufficient to treat NASH, wherein the patient has been determined to have a serum Pro-C3 level greater than 10, 15 or 20 ng/ML. In another embodiment, a modified FGF-21 for use in a method of monitoring responsiveness of a patient having NASH to treatment with a modified FGF-21 is provided, wherein a decreased serum Pro-C3 level in a blood sample from the patient obtained during or after treatment, as compared to a serum Pro-C3 level in a blood sample from the patient obtained prior to treatment with the modified FGF-21, indicates that the patient is responsive to treatment with the modified FGF-21.

Finally, methods of identifying a patient having NASH that is suitable for treatment with a modified FGF-21 are provided, wherein the methods comprise determining a serum Pro-C3 level in a blood sample from the patient using an in vitro assay, wherein the serum Pro-C3 level in the blood sample is greater than 10, 15 or 20 ng/ML. Other features and advantages of the methods of treatment will be apparent from the following description, the examples, and from the claims. All publications, patent applications, patents, and other references mentioned herein are incorporated by reference in their entirety.

BRIEF DESCRIPTION OF THE DRAWINGS

FIG. 2A depicts the absolute change in hepatic fraction in patients from baseline to week 16. FIG. 2B shows the MRI-PDFF measurements of a patient who experienced a reduction in hepatic fat fraction following BMS-986036 treatment. FIG. 2C depicts the percent of patients with ≥30%, ≥20%, or ≥10% relative reductions in hepatic fat fraction.

FIGS. 3A-3B depict the change in liver stiffness in patients at week 16. FIG. 3A shows the absolute change in liver stiffness (MRE) from baseline to Week 16 and FIG. 3B shows the percent of patients with ≥15% relative reduction in liver stiffness (MRE) at week 16.

FIG. 6A shows Pro-C3 levels for individuals treated with BMS-986036. FIG. 6B shows the frequency of Pro-C3 levels.

FIG. 7A shows the percent change from baseline PRO-C3 levels at week 16. FIG. 7B shows the percent of patients with ≥15% relative reduction in PRO-C3 at week 16. Inferential statistical analyses were conducted post hoc using a longitudinal repeated measurements model analysis. $^a$Sample size for serum Pro-C3 was smaller than MRI-PDFF due to some non-evaluable samples at baseline.

FIG. 8A shows the percent change in ALT from baseline to week 16. FIG. 8B shows the percent change in AST from baseline to week 16. BMS-986036 QD and QW treatment were associated with improvements from baseline in biomarkers of liver injury (n indicates number of patients with ALT/AST data at end of treatment (EOT)).

DETAILED DESCRIPTION

Figure 1:
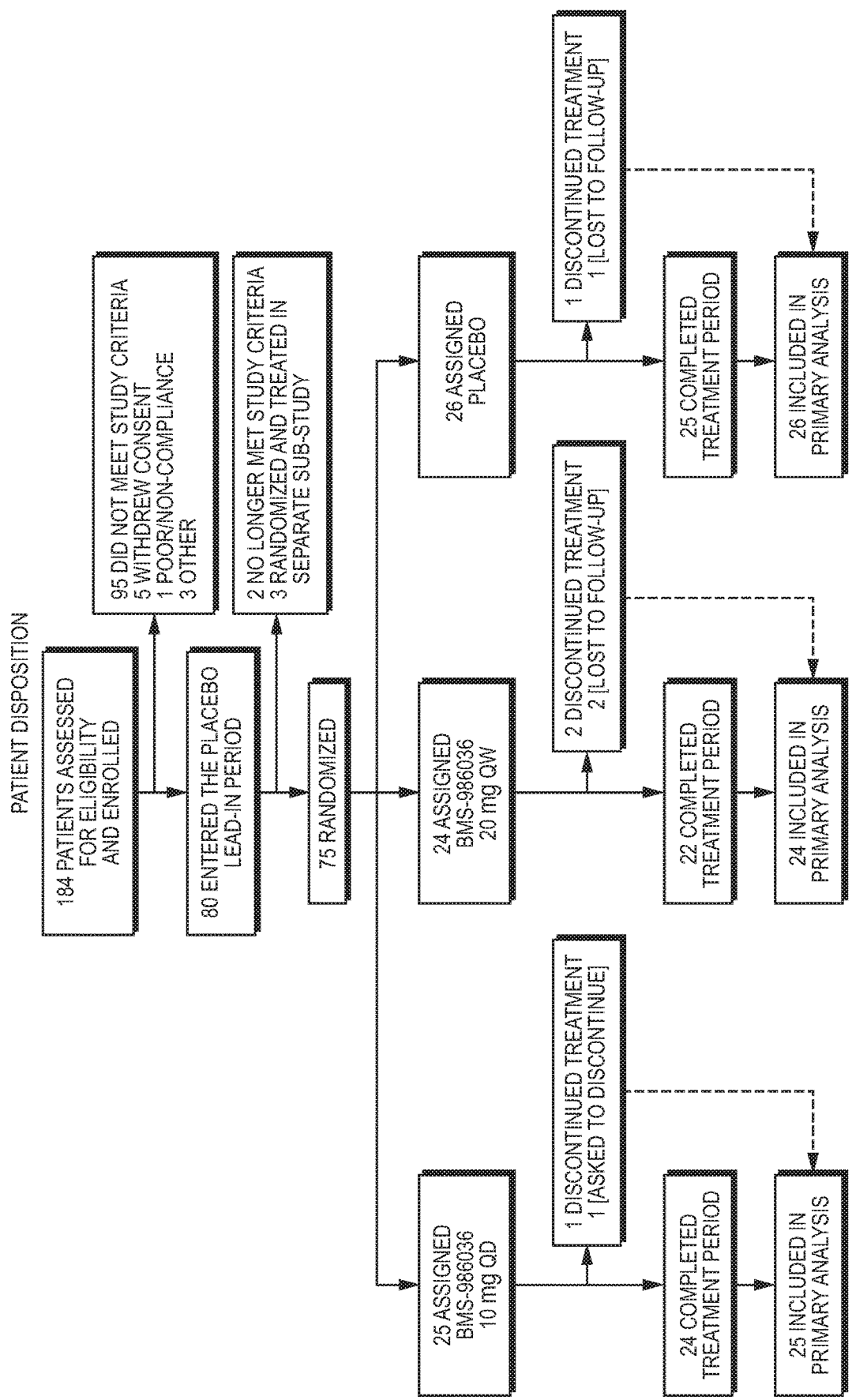
FIG. 1 is a schematic showing the patient disposition for the trial.

Provided herein are methods for treating a patient having NASH by administering to the patient a modified FGF-21 if the patient has been determined to have a particular serum threshold level of Pro-C3 (e.g., greater than about 10 ng/ML, greater than 15 ng/ML, or greater than about 17 ng/ML, or greater than about 20 ng/ML) prior to administration to the patient of a modified FGF-21, as well as methods for monitoring responsiveness of a patient having NASH to treatment with a modified FGF-21 based on serum levels of Pro-C3.

I. Definitions

In order that the present description may be more readily understood, certain terms are first defined. Additional definitions are set forth throughout the detailed description. Unless defined otherwise, all technical and scientific terms used herein have the same meaning as commonly understood by one of ordinary skill in the art, and conventional methods of immunology, protein chemistry, biochemistry, recombinant DNA techniques, and pharmacology are employed.

As used herein, the singular forms "a", "an" and "the" include plural referents unless the context clearly dictates otherwise. The use of "or" or "and" means "and/or" unless stated otherwise. Furthermore, use of the term "including" as well as other forms, such as "include", "includes", and "included", is not limiting.

The term "about" as used herein when referring to a measurable value such as an amount, a temporal duration and the like, is encompasses variations of up to ±10% from the specified value. Unless otherwise indicated, all numbers expressing quantities of ingredients, properties such as molecular weight, reaction conditions, etc., used herein are to be understood as being modified by the term "about".

As used herein, the term "normal," when used to modify the term "individual" or "subject" refers to an individual or group of individuals who does/do not have a particular disease or condition (e.g., NASH) and is also not suspected of having or being at risk for developing the disease or condition. The term "normal" is also used herein to qualify a biological specimen or sample (e.g., a blood or a fraction thereof) isolated from a normal or healthy individual or subject (or group of such subjects), for example, a "normal control sample" or "normal control biological fluid".

"Polypeptide," "peptide," and "protein" are used interchangeably and mean any peptide-linked chain of amino acids, regardless of length or post-translational modification. The proteins described herein can contain or be wild-type proteins or can be variants that have not more than 50 (e.g., not more than one, two, three, four, five, six, seven, eight, nine, ten, 12, 15, 20, 25, 30, 35, 40, or 50) conservative amino acid substitutions. Conservative substitutions typically include substitutions within the following groups: glycine and alanine; valine, isoleucine, and leucine; aspartic acid and glutamic acid; asparagine, glutamine, serine and threonine; lysine, histidine and arginine; and phenylalanine and tyrosine.

As used herein, percent (%) amino acid sequence identity is defined as the percentage of amino acids in a candidate sequence that are identical to the amino acids in a reference sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST software. Appropriate parameters for measuring alignment, including any algorithms needed to achieve maximal alignment over the full-length of the sequences being compared can be determined by known methods.

The term "pharmaceutical formulation" or "pharmaceutical composition" refers to preparations which are in such form as to permit the biological activity of the active ingredients to be unequivocally effective, and which contain no additional components which are significantly toxic to the subjects to which the formulation would be administered.

As used herein, an "aqueous" pharmaceutical composition is a composition suitable for pharmaceutical use, wherein the aqueous carrier is water. A composition suitable for pharmaceutical use may be sterile, homogeneous and/or isotonic. Aqueous pharmaceutical compositions may be prepared directly in an aqueous form and/or may be reconstituted from a lyophilisate.

Unless otherwise defined, all technical and scientific terms used herein have the same meaning as commonly understood by one of ordinary skill in the art to which this disclosure pertains. Preferred methods and materials are described below, although methods and materials similar or equivalent to those described herein can also be used in the practice or testing of the presently disclosed methods and compositions. All publications, patent applications, patents, and other references mentioned herein are incorporated by reference in their entirety.

Other features and advantages of the present disclosure, e.g., methods for treating NASH in a subject, will be apparent from the following description, the examples, and from the claims.

1. Pro-C3

Pro-C3 levels above a particular threshold level (e.g., greater than about 10 ng/ML, greater than 15 ng/ML, or greater than 20 ng/ML) can be used as an indicator to evaluate whether a patient having NASH will be responsive to treatment with a modified FGF-21 (such as BMS-986036) and/or to monitor response to treatment with a modified FGF-21.

Pro-C3 (also known as "true collagen type III formation") is a marker of true type III collagen formation. Together with type I collagen, type III collagen constitutes the major structural proteins in the human body, in which type III collagen is crucial for type I collagen fibrillogenesis except in bones, which almost exclusively consist of type I collagen (see Bao X, et al., J Genet Genomics. 2007; 34:223-228; Jensen L T, et al., Cardiovasc Res. 1997; 33:535-539; and Nielsen et al., Am J Transl Res. 2013; 5(3): 303-315). During fibrillar assembly the N-terminal propeptide of type III collagen is cleaved off by specific N-proteases prior to incorporation of the mature collagen in the extracellular matrix (ECM), thus released in the ECM and into circulation. The propeptide molecule consists of three identical α-chains with a total molecular weight of 42 kDa. The GenBank (National Center for Biotechnology Information (NCBI)) reference numbers for the protein and gene sequences of Pro-C3 (Collagen α-1 (III) chain) are NP 000081.1 (UniProt P02461) and NM_000090.3, respectively, the sequences of which are expressly incorporated herein by reference. Fragments of the protein, for example, the N-terminal propeptide, such as amino acid sequence 144-CPTGPQNYSP-153 (SEQ ID NO: 3), in the al chain Pro-C3, may be used to generate antibodies for immunoassay (e.g., ELISA). Nielsen et al., Am J Transl Res. 2013; 5(3): 303-315.

Measuring or determining protein levels of a biomarker, such as Pro-C3, in a biological sample may be performed by any suitable method (see, e.g., Harlow and Lane (1988) "Antibodies: A Laboratory Manual", Cold Spring Harbor Laboratory: Cold Spring Harbor, N.Y.).

In general, protein levels are determined by contacting a biological sample obtained from a subject with binding agents for one or more of the biomarker proteins; detecting, in the biological sample the expression level (e.g., levels) of one or more of the biomarker proteins that bind to the binding agents; and comparing the levels of one or more of the biomarker proteins in the sample with the levels of the corresponding protein biomarkers in a control sample (e.g., a normal sample).

Suitable binding agents also include an antibody specific for a biomarker protein described herein (e.g., Pro-C3). Suitable antibodies for use in the methods of the present invention include monoclonal and polyclonal antibodies and antigen-binding fragments (e.g., Fab fragments or scFvs) of antibodies. Antibodies, including monoclonal and polyclonal antibodies, fragments and chimeras, may be prepared using methods known in the art (see, for example, Kohler and Milstein (1975) Nature 256:495-497; Kozbor et al. (1985) J Immunol Methods 81:31-42; Cote et al. (1983) Proc Natl Acad Sci USA 80:2026-203; and Zhang et al. (2002) J Biol Chem 277:39379-39387). Exemplary antibodies include antibodies or fragments thereof that bind to the N-terminal propeptide, such as amino acid sequence 144-CPTGPQNYSP-153 (SEQ ID NO: 3), in the al chain Pro-C3 (e.g., antibody NB61N-62, as described in Nielsen et al., Am J Transl Res. 2013; 5(3): 303-315). Antibodies to be used in the methods of the invention can be purified by methods well known in the art. Antibodies may also be obtained from commercial sources.

In certain embodiments, the binding agent is directly or indirectly labeled with a detectable moiety. The role of a detectable agent is to facilitate the detection step of the diagnostic method by allowing visualization of the complex formed by binding of the binding agent to the protein marker (or fragment thereof). The detectable agent can be selected such that it generates a signal that can be measured and whose intensity is related (preferably proportional) to the amount of protein marker present in the sample being analyzed. Methods for labeling biological molecules such as polypeptides and antibodies are well-known in the art. Any of a wide variety of detectable agents can be used in the practice of the present invention. Suitable detectable agents include, but are not limited to: various ligands, radionuclides, fluorescent dyes, chemiluminescent agents, microparticles (such as, for example, quantum dots, nanocrystals, phosphors and the like), enzymes (such as, e.g., those used in an ELISA, i.e., horseradish peroxidase, beta-galactosidase, luciferase, alkaline phosphatase), colorimetric labels, magnetic labels, and biotin, digoxigenin or other haptens and proteins for which antisera or monoclonal antibodies are available.

In certain embodiments, the binding agents (e.g., antibodies) may be immobilized on a carrier or support (e.g., a bead, a magnetic particle, a latex particle, a microtiter plate well, a cuvette, or other reaction vessel). Examples of suitable carrier or support materials include agarose, cellulose, nitrocellulose, dextran, Sephadex®, Sepharose®, liposomes, carboxymethyl cellulose, polyacrylamides, polystyrene, gabbros, filter paper, magnetite, ion-exchange resin, plastic film, plastic tube, glass, polyamine-methyl vinyl-ether-maleic acid copolymer, amino acid copolymer, ethylene-maleic acid copolymer, nylon, silk, and the like. Binding agents may be indirectly immobilized using second binding agents specific for the first binding agents (e.g., mouse antibodies specific for the protein markers may be immobilized using sheep anti-mouse IgG Fc fragment specific antibody coated on the carrier or support).

Protein expression levels in a biological sample may be determined using immunoassays. Examples of such assays are time resolved fluorescence immunoassays (TR-FIA), radioimmunoas says, enzyme immunoassays (e.g., ELISA), immunofluorescence immunoprecipitation, latex agglutination, hemagglutination, Western blot, and histochemical tests, which are conventional methods well-known in the art. Methods of detection and quantification of the signal generated by the complex formed by binding of the binding agent with the protein marker will depend on the nature of the assay and of the detectable moiety (e.g., fluorescent moiety). An exemplary Pro-C3 ELISA is described in Nielson et al., Am J Transl Res 2013; 5(3):303-315, which is incorporated herein by reference.

In one example, the presence or amount of protein expression of a gene (e.g., a biomarker, such as Pro-C3) can be determined using a Western blotting technique. For example, a lysate can be prepared from a biological sample, or the biological sample (e.g., blood or a fraction thereof) itself, can be contacted with Laemmli buffer and subjected to sodium-dodecyl sulfate polyacrylamide gel electrophoresis (SDS-PAGE). SDS-PAGE-resolved proteins, separated by size, can then be transferred to a filter membrane (e.g., nitrocellulose) and subjected to immunoblotting techniques using a detectably-labeled antibody specific to the protein of interest. The presence or amount of bound detectably-labeled antibody indicates the presence or amount of protein in the biological sample.

In another example, an immunoassay can be used for detecting and/or measuring the protein expression of a biomarker protein, such as Pro-C3. As above, for the purposes of detection, an immunoassay can be performed with an antibody that bears a detection moiety (e.g., a fluorescent agent or enzyme). Proteins from a biological sample can be conjugated directly to a solid-phase matrix (e.g., a multi-well assay plate, nitrocellulose, agarose, Sepharose®, encoded particles, or magnetic beads) or it can be conjugated to a first member of a specific binding pair (e.g., biotin or streptavidin) that attaches to a solid-phase matrix upon binding to a second member of the specific binding pair (e.g., streptavidin or biotin). Such attachment to a solid-phase matrix allows the proteins to be purified away from other interfering or irrelevant components of the biological sample prior to contact with the detection antibody and also allows for subsequent washing of unbound antibody. Here, as above, the presence or amount of bound detectably-labeled antibody indicates the presence or amount of protein in the biological sample.

Alternatively, the protein expression levels may be determined using mass spectrometry based methods or image-based methods known in the art for the detection of proteins. Other suitable methods include 2D-gel electrophoresis, proteomics-based methods such as the identification of individual proteins recovered from the gel (e.g., by mass spectrometry or N-terminal sequencing) and/or bioinformatics.

Methods for detecting or measuring protein expression can, optionally, be performed in formats that allow for rapid preparation, processing, and analysis of multiple samples. This can be, for example, in multi-well assay plates (e.g., 96 wells or 386 wells) or arrays (e.g., protein chips). Stock solutions for various reagents can be provided manually or robotically, and subsequent sample preparation, pipetting, diluting, mixing, distribution, washing, incubating (e.g., hybridization), sample readout, data collection (optical data) and/or analysis (computer aided image analysis) can be done robotically using commercially available analysis software, robotics, and detection instrumentation capable of detecting the signal generated from the assay. Examples of such detectors include, but are not limited to, spectrophotometers, luminometers, fluorimeters, and devices that measure radio-isotope decay. Exemplary high-throughput cell-based assays (e.g., detecting the presence or level of a target protein in a cell) can utilize ArrayScan® VTI HCS Reader or KineticScan® HCS Reader technology (Cellomics Inc., Pittsburgh, Pa.).

Expression of the biomarker can also be detected at the nucleic acid level (e.g., based on RNA levels). In one embodiment, RNA is detected using an RNA-ISH assay. Another method for determining the level of RNA in a sample involves the process of nucleic acid amplification from homogenized tissue, e.g., by RT-PCR (reverse transcribing the RNA and then, amplifying the resulting cDNA employing PCR or any other nucleic acid amplification method, followed by the detection of the amplified molecules. In another embodiment, RNA expression is assessed by quantitative fluorogenic RT-PCR (qPCR).

In one embodiment, the methods described herein involve comparing the measured expression level or activity of a biomarker protein, such as Pro-C3 (as measured in a biological sample obtained from a patient) to a control sample. In some embodiments, control sample is obtained from the patient prior to administering to the patient the modified FGF-21 (e.g., BMS-986036). In some embodiments, the control sample can be (or can be based on), e.g., a collection of samples obtained from one or more (e.g., two, three, four, five, six, seven, eight, nine, 10, 15, 20, 25, 30, 35, or 40 or more) healthy individuals that have not been administered modified FGF-21. In some embodiments, the control sample can be (or can be based on), e.g., a pooled sample obtained from two or more (e.g., two, three, four, five, six, seven, eight, nine, 10, 15, 20, 25, 30, 35, or 40 or more) individuals. In some embodiments of any of the methods described herein, the pooled samples can be from healthy individuals, or at least, individuals who do not have or are not suspected of having NASH. In another embodiment, determining whether the expression level or activity of a biomarker, such as Pro-C3, or hepatic fat fraction, has decreased following treatment with a modified FGF-21 can involve comparing the expression level or activity of the biomarker in a biological sample obtained from a patient prior to treatment to the expression level of the biomarker in a sample of the same biological type obtained from the patient after treatment with the modified FGF-21 (e.g., one day, two days, three days, four days, five days, six days, 1 week, 2 weeks, 3 weeks, a month, 6 weeks, two months, three months, four months, 5 months, or 6 months after treatment).

In some embodiments, determining whether a modified FGF-21 has produced a desired effect (e.g., a reduction in serum Pro-C3 levels (e.g., by about 5, 10, 15, 20, 25, 30, 40, or 50%) and/or liver stiffness) in a human can be performed by querying whether the post-treatment expression level of the biomarker (e.g., Pro-C3) falls within a predetermined range indicative of responsiveness to a modified FGF-21 by a human. In some embodiments, determining whether a modified FGF-21 has produced a desired effect in a human can include querying if the post-treatment expression level or activity of the biomarker (e.g., Pro-C3) falls above or below a predetermined cut-off value. A cut-off value is typically the expression level or activity of a given biomarker in a given biological sample above or below which is considered indicative of a certain phenotype, e.g., responsiveness to therapy with a modified FGF-21.

In some embodiments of any of the methods described herein, the same practitioner may administer the modified FGF-21 to the patient prior to determining whether a change in the expression level or activity of the biomarker (e.g., Pro-C3) has occurred, whereas in some embodiments, the practitioner who administers the modified FGF-21 to the patient is different from the practitioner who determines whether a response has occurred in the patient. In some embodiments, the practitioner may obtain a biological sample from the patient prior to administration of the modified FGF-21. In some embodiments, the practitioner may obtain a biological sample from the patient following the administration of the modified FGF-21 to the patient. In some embodiments, the post-treatment sample can be obtained from the patient less than 48 (e.g., less than 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, nine, eight, seven, six, five, four, three, two, or even less than one) hours following administration of the modified FGF-21 to the patient. In some embodiments, the post-treatment sample can be obtained from the patient less than 20 (e.g., less than 19, 18, 17, 16, 15, 14, 13, 12, 11, 10, nine, eight, seven, six, five, four, three, two, or one) day(s) after administering to the patient the modified FGF-21. In some embodiments, the biological sample is obtained from the patient no more than 20 (e.g., no more than 19, 18, 17, 16, 15, 14, 13, 12, 11, 10, nine, eight, seven, six, five, four, three, two, or one) day(s) after the modified FGF-21 is administered to the patient.

In some embodiments, the serum level of Pro-C3 is decreased by at least 5 (e.g., at least 10, 15, 20, 25, 30, 35, 40, 45, 50, 55, 60, 65, or 70) % following administration of the modified FGF-21. In some embodiments, the serum level of Pro-C3 is decreased by at least 15% following administration of the modified FGF-21. In some embodiments, the serum level of Pro-C3 is decreased by at least 20% following administration of the modified FGF-21.

In some embodiments, the serum level of Pro-C3 is decreased to within 90 (e.g., 85, 80, 75, 70, 65, 60, 55, 50, 45, 40, 35, or 30) % of the normal serum level of Pro-C3 following administration of the modified FGF-21.

In some embodiments, the serum level of Pro-C3 is decreased to within 90 (e.g., 85, 80, 75, 70, 65, 60, 55, 50, 45, 40, 35, or 30) % of the pre-treatment (prior to treatment) Baseline serum level of Pro-C3 following administration of the modified FGF-21.

2. Modified FGF-21 Polypeptides

As described in U.S. Pat. No. 9,434,778 (the contents of which are expressly incorporated reference herein in its entirety), fibroblast growth factors are polypeptides widely expressed in developing and adult tissues (Baird et al., Cancer Cells, 3:239-243, 1991) that play crucial roles in multiple physiological functions (McKeehan et al., Prog. Nucleic Acid Res. Mol. Biol. 59:135-176, 1998; Burgess, W. H. et al., Annu. Rev. Biochem. 58:575-606 (1989). According to the literature, the FGF family consists of at least twenty-two members (Reuss et al., Cell Tissue Res. 313: 139-157 (2003)).

Fibroblast growth factor 21 (FGF-21) has been described in the literature (Nishimura et al., Biochimica et Biophysica Acta, 1492:203-206 (2000); WO 01/36640; and WO 01/18172, and U.S. Patent Publication No. 20040259780, each of which is expressly incorporated by reference herein in its entirety). Unlike other FGFs, FGF-21 has been reported not to have proliferative and tumorigenic effects (Ornitz and Itoh, Genome Biology 2001, 2(3): reviews 3005.1-3005.12).

Certain FGF-21 polypeptides and uses thereof are described in U.S. Patent Publication No. 20010012628, U.S. Pat. No. 6,716,626, U.S. Patent Publication No. 2004/0259780, WO 03/011213, Kharitonenkov et al. J Clin Invest. 2005 June; 115(6):1627-35, WO 03/059270, U.S. Patent Publication No. 2005/0176631, WO 2005/091944, WO 2007/0293430, U.S. Patent Publication No. 2007/0293430, WO/2008/121563, U.S. Pat. No. 4,904,584, WO 99/67291, WO 99/03887, WO 00/26354, and U.S. Pat. No. 5,218,092 each of which is incorporated by reference herein in its entirety.

As used herein, "modified FGF-21 polypeptide," "modified fibroblast growth factor 21" or "modified FGF-21" and unhyphenated forms thereof are used interchangeably and shall include those polypeptides and proteins that differ from wild-type FGF-21 (e.g., wild-type human FGF-21 of SEQ ID NO:1) and typically have at least one biological activity of a fibroblast growth factor 21, as well as FGF-21 analogs, FGF-21 isoforms, FGF-21 mimetics, FGF-21 fragments, hybrid FGF-21 proteins, fusion proteins, oligomers and multimers, homologues, glycosylation pattern variants, variants, splice variants, and muteins, thereof, regardless of the biological activity of same. The term "modified FGF-21 polypeptide" and "modified FGF-21" encompass FGF-21 polypeptides comprising one or more amino acid substitutions, additions or deletions. For example, modified FGF-21 polypeptides of the present disclosure may comprise one or more non-natural amino acid modification, optionally in conjunction with modifications with one or more natural amino acids. Exemplary substitutions, insertions or deletions in a wide variety of amino acid positions in FGF-21 polypeptides (including those described herein and others), including but not limited to substitutions that modulate pharmaceutical stability, that modulate one or more of the biological activities of the FGF-21 polypeptide, such as but not limited to, increase agonist activity, increase solubility of the polypeptide, decrease protease susceptibility, decrease deamidation, convert the polypeptide into an antagonist, reduce immunogenicity or toxicity, or facilitate purification or manufacturability, etc., are encompassed by the term "modified FGF-21 polypeptide."

In some embodiments, the "modified FGF-21" encompass FGF-21 polypeptides comprising one or more non-naturally encoded amino acid substitutions or additions. In some embodiments, the "modified FGF-21" encompass FGF-21 polypeptides comprising one or more non-naturally encoded amino acid substitutions.

In some cases, the non-naturally encoded amino acid substitution(s) may be combined with other additions, substitutions or deletions within the modified FGF-21 polypeptide to affect other biological traits of the modified FGF-21 polypeptide relative to another FGF-21 polypeptide.

In some cases, the other additions, substitutions or deletions may increase the stability (including but not limited to, resistance to proteolytic degradation) of the modified FGF- 21 polypeptide or increase affinity of the modified FGF-21 polypeptide for its receptor. In some cases, the other additions, substitutions or deletions may increase the pharmaceutical stability of the modified FGF-21 polypeptide. In some cases, the other additions, substitutions or deletions may increase the solubility (including but not limited to, when expressed in E. coli or other host cells) of the modified FGF-21 polypeptide. In some embodiments, the other addition, substitution or deletion may modulate affinity of the modified FGF-21 polypeptide for its receptor, binding proteins, or associated ligand, modulate signal transduction after binding to its receptor, modulates circulating half-life, modulate release or bio-availability, facilitates purification, or improve or alter a particular route of administration. In some embodiments, modified FGF-21 polypeptides can comprise chemical or enzyme cleavage sequences, protease cleavage sequences, reactive groups, antibody-binding domains (including but not limited to, FLAG or poly-His) or other affinity based sequences (including, but not limited to, FLAG, poly-His, GST, etc.) or linked molecules (including, but not limited to, biotin) that improve detection (including, but not limited to, GFP), purification, transport through tissues or cell membranes, or other traits of the polypeptide.

Multiple polymorphisms of FGF-21 have been identified. Leucine or proline have been described at the same position in U.S. Patent Publication No. 20010012628 and U.S. Pat. No. 6,716,626. N-terminal leader or signal sequences that differ by 1 amino acid (leucine) are shown in U.S. Pat. No. 6,716,626 and U.S. Patent Publication No. 20040259780. FGF-21 polypeptide variants or mutants include, but are not limited to, those disclosed in U.S. Pat. No. 6,716,626; U.S. Patent Publication Nos. 2005/0176631, 2005/0037457, 2004/0185494, 2004/0259780, 2002/0164713, and 2001/0012628; WO 01/36640; WO 03/011213; WO 03/059270; WO 04/110472; WO 05/061712; WO 05/072769; WO 05/091944; WO 05/113606; WO 06/028595; WO 06/028714; WO 06/050247; WO 06/065582; WO 06/078463; WO01/018172; WO09/149171; WO10/042747; WO12/066075; WO11/154349; WO13/052311; WO13/188181, which are expressly incorporated by reference in their entireties herein.

The term "modified FGF-21 polypeptide" also includes biologically-active fragments, biologically active variants and stereoisomers of the naturally-occurring FGF-21 as well as agonist, mimetic, and antagonist variants of the naturally-occurring FGF-21 and polypeptide fusions thereof. Fusions comprising additional amino acids at the amino terminus, carboxyl terminus, or both, are encompassed by the term "modified FGF-21 polypeptide." Exemplary fusions include, but are not limited to, e.g., methionyl FGF-21 in which a methionine is linked to the N-terminus of FGF-21 resulting from the recombinant expression of the mature form of FGF-21 lacking the leader or signal peptide or portion thereof (a methionine is linked to the N-terminus of FGF-21 resulting from the recombinant expression, e.g. in E. coli), fusions for the purpose of purification (including, but not limited to, to poly-histidine or affinity epitopes), fusions with serum albumin binding peptides such as PK extending (PKE) adnectin and fusions with serum proteins such as serum albumin, and fusion proteins comprising FGF-21 and one or more other molecules ("fusion partner"), including but not limited to, serum albumin, Fc domain, immunoglobulin constant region, unstructured polypeptide, and adnectin, and a fragment thereof. Any such fragments can be prepared from the proteins by standard biochemical methods, or by expressing a polynucleotide encoding the fragment.

The term "modified FGF-21 polypeptide" includes polypeptides conjugated to a polymer such as PEG and may optionally comprise one or more additional derivitizations of cysteine, lysine, or other residues. For example, the modified FGF-21 polypeptide may be conjugated to a linker or polymer, wherein the linker or polymer may be conjugated to a non-natural amino acid in the modified FGF-21 polypeptide according to the present disclosure, or may be conjugated to a naturally encoded amino acid utilizing techniques known in the art such as coupling to lysine or cysteine. Exemplary linkers including but are not limited to, small organic compounds, water soluble polymers of a variety of lengths such as poly(ethylene glycol) or polydextran, or peptide or polypeptides of various lengths.

The term "modified FGF-21 polypeptide" also includes glycosylated modified FGF-21, such as but not limited to, polypeptides glycosylated at any amino acid position, N-linked or 0-linked glycosylated forms of the polypeptide. Variants containing single nucleotide changes are also considered as biologically active variants of FGF-21 polypeptide. In addition, splice variants are also included. The term "modified FGF-21 polypeptide" also includes FGF-21 polypeptide heterodimers, homodimers, heteromultimers, or homomultimers of any one or more unmodified or modified FGF-21 polypeptides or any other polypeptide, protein, carbohydrate, polymer, small molecule, linker, ligand, or other biologically active molecule of any type, linked by chemical means or expressed as a fusion protein, as well as polypeptide analogues containing, for example, specific deletions or other modifications yet maintain biological activity.

A "non-naturally encoded amino acid" refers to an amino acid that is not one of the 20 common amino acids or pyrrolysine or selenocysteine. Other terms that may be used synonymously with the term "non-naturally encoded amino acid" are "non-natural amino acid," "unnatural amino acid," "non-naturally occurring amino acid," and variously hyphenated and non-hyphenated versions thereof. The term "non-naturally encoded amino acid" also includes, but is not limited to, amino acids that occur by modification (e.g. post-translational modifications) of a naturally encoded amino acid (including but not limited to, the 20 common amino acids or pyrrolysine and selenocysteine) but are not themselves naturally incorporated into a growing polypeptide chain by the translation complex. Examples of such non-naturally encoded amino acids include, but are not limited to, N-acetylglucosaminyl-L-serine, N-acetylglucosaminyl-L-threonine, and O-phosphotyrosine.

An "amino terminus modification group" refers to any molecule that can be attached to the amino terminus of a polypeptide. Similarly, a "carboxy terminus modification group" refers to any molecule that can be attached to the carboxy terminus of a polypeptide. Terminus modification groups include, but are not limited to, various water soluble polymers, methionine, peptides or proteins such as serum albumin, Fc domain, immunoglobulin constant region, unstructured polypeptide, adnectin, or a fragment thereof, or other moieties that increase serum (in vivo) half-life of peptides.

The terms "functional group", "active moiety", "activating group", "leaving group", "reactive site", "chemically reactive group" and "chemically reactive moiety" are used in the art and herein to refer to distinct definable portions or units of a molecule. The terms are somewhat synonymous in the chemical arts and are used herein to indicate the portions of molecules that perform some function or activity and are reactive with other molecules.

The term "linkage" is used herein to refer to groups or bonds that normally are formed as the result of a chemical reaction and typically are covalent linkages. Hydrolytically stable linkages means that the linkages are substantially stable in water and do not react with water at useful pH values, including but not limited to, under physiological conditions for an extended period of time, perhaps even indefinitely. Hydrolytically unstable or degradable linkages mean that the linkages are degradable in water or in aqueous solutions, including for example, blood. Enzymatically unstable or degradable linkages mean that the linkage can be degraded by one or more enzymes. As understood in the art, PEG and related polymers may include degradable linkages in the polymer backbone or in the linker group between the polymer backbone and one or more of the terminal functional groups of the polypetide molecule. For example, ester linkages formed by the reaction of PEG carboxylic acids or activated PEG carboxylic acids with alcohol groups on a biologically active agent generally hydrolyze under physiological conditions to release the agent. Other hydrolytically degradable linkages include, but are not limited to, carbonate linkages; imine linkages resulted from reaction of an amine and an aldehyde; phosphate ester linkages formed by reacting an alcohol with a phosphate group; hydrazone linkages which are reaction product of a hydrazide and an aldehyde; acetal linkages that are the reaction product of an aldehyde and an alcohol; orthoester linkages that are the reaction product of a formate and an alcohol; peptide linkages formed by an amine group, including but not limited to, at an end of a polymer such as PEG, and a carboxyl group of a peptide; and oligonucleotide linkages formed by a phosphoramidite group, including but not limited to, at the end of a polymer, and a 5' hydroxyl group of an oligonucleotide. Exemplary linkages also include oxime linkage resulted from the reaction of a carbonyl group and aminooxy group.

Modified FGF-21 polypeptides suitable for use in the invention can be generated using methods well known in the art. Alternatively, art recognized modified FGF-21 polypeptides can be used. For example modified FGF-21 polypeptides are described in U.S. Pat. Nos. 9,079,971 and 9,434,778, the contents of which are expressly incorporated herein by reference in their entireties.

An exemplary modified FGF-21 may be a pegylated analogue of human FGF-21. In one embodiment, the modified FGF-21 comprises the polypeptide of SEQ ID NO:1, except that an amino acid in the polypeptide is substituted by a non-naturally encoded amino acid, wherein said non-naturally encoded amino acid is at a position corresponding to residue 108 of SEQ ID NO:1.

In another embodiment, the modified FGF-21 comprises the polypeptide of SEQ ID NO:1, except that an amino acid in the polypeptide is substituted by a non-naturally encoded amino acid, wherein: (a) said non-naturally encoded amino acid is at a position corresponding to residue 108 of SEQ ID NO:1; (b) said non-naturally encoded amino acid is linked to a polymer comprising a poly(ethylene glycol).

In another embodiment, the modified FGF-21 comprises the polypeptide of SEQ ID NO:1 except that the amino acid at position 108 of SEQ ID NO:1 is substituted by a non-naturally encoded amino acid, wherein: (a) said non-naturally encoded amino acid comprises para-acetyl phenylalanine, and (b) said non-naturally encoded amino acid is linked to a polymer comprising a poly(ethylene glycol). In one embodiment, the poly(ethylene glycol) may have an average molecular weight of about 30 kDa.

In another embodiment, the non-naturally encoded amino acid is linked to said polymer through an oxime linkage.

In another embodiment, the modified FGF-21 comprises SEQ ID NO:2.

In another embodiment, the modified FGF-21 comprises SEQ ID NO:2, wherein the para-acetyl phenylalanine in SEQ ID NO:2 is linked to a polymer comprising a poly (ethylene glycol).

In another embodiment, the modified FGF-21 comprises SEQ ID NO:2, wherein the para-acetyl phenylalanine in SEQ ID NO:2 is linked to a polymer comprising a poly (ethylene glycol) having an average molecular weight of about 30 kDa. In another embodiment, the modified FGF-21 may be BMS-986036.

Also provided is a modified FGF-21 for use in the methods described herein. In one embodiment, a modified FGF-21 for use in a method of treating NASH in a patient is provided, wherein the method comprises administering to the patient a modified FGF-21 in an amount and with a frequency sufficient to treat NASH, wherein the patient has been determined to have a serum Pro-C3 level greater than 10, 15 or 20 ng/ML. In another embodiment, a modified FGF-21 for use in a method of monitoring responsiveness of a patient having NASH to treatment with a modified FGF-21 is provided, wherein a decreased serum Pro-C3 level in a blood sample from the patient obtained during or after treatment, as compared to a serum Pro-C3 level in a blood sample from the patient obtained prior to treatment with the modified FGF-21, indicates that the patient is responsive to treatment with the modified FGF-21.

3. Samples and Collection

Suitable biological samples for use in the methods described herein include whole blood (or a fraction thereof). A biological sample can be further fractionated, if desired, to a fraction containing particular analytes (e.g., proteins) of interest. For example, a whole blood sample can be fractionated into serum or into fractions containing particular types of proteins.

The biological samples can be obtained from a subject, e.g., a patient having, suspected of having, or at risk of developing NASH. Any suitable methods for obtaining the biological samples can be employed.

In some embodiments, a protein extract may be prepared from a biological sample. In some embodiments, a protein extract contains the total protein content. Methods of protein extraction are well known in the art. See, e.g., Roe (2001) "Protein Purification Techniques: A Practical Approach", 2$^{nd}$ Edition, Oxford University Press. Numerous different and versatile kits can be used to extract proteins from bodily fluids and tissues, and are commercially available from, for example, BioRad Laboratories (Hercules, Calif.), BD Biosciences Clontech (Mountain View, Calif.), Chemicon International, Inc. (Temecula, Calif.), Calbiochem (San Diego, Calif.), Pierce Biotechnology (Rockford, Ill.), and Invitrogen Corp. (Carlsbad, Calif.).

Methods for obtaining and/or storing samples that preserve the activity or integrity of cells in the biological sample are well known to those skilled in the art. For example, a biological sample can be further contacted with one or more additional agents such as appropriate buffers and/or inhibitors, including protease inhibitors, the agents meant to preserve or minimize changes (e.g., changes in osmolarity or pH) in protein structure. Such inhibitors include, for example, chelators such as ethylenediamine tetraacetic acid (EDTA), ethylene glycol tetraacetic acid (EGTA), protease inhibitors such as phenylmethylsulfonyl fluoride (PMSF), aprotinin, and leupeptin. Appropriate buffers and conditions for storing or otherwise manipulating whole cells are described in, e.g., Pollard and Walker (1997), "Basic Cell Culture Protocols," volume 75 of *Methods in molecular biology*, Humana Press; Masters (2000) "Animal cell culture: a practical approach," volume 232 of *Practical approach series*, Oxford University Press; and Jones (1996) "Human cell culture protocols," volume 2 of *Methods in molecular medicine*, Humana Press.

A sample also can be processed to eliminate or minimize the presence of interfering substances. For example, a biological sample can be fractionated or purified to remove one or more materials (e.g., cells) that are not of interest. Methods of fractionating or purifying a biological sample include, but are not limited to, flow cytometry, fluorescence activated cell sorting, and sedimentation.

4. Methods for Treatment

Also provided herein are methods for treating a patient having NASH by administering to the patient a modified Fibroblast growth factor 21 (FGF-21) if the patient has been determined to have a particular serum threshold level of Pro-C3 (e.g., greater than about 10 ng/ML, 11 ng/ML, 12 ng/ML, 13 ng/ML, 14 ng/ML, 15 ng/ML, 16 ng/ML, 17 ng/ML, 18 ng/ML, 19 ng/ML, 20 ng/ML, 22 ng/ML, 23 ng/ML).

The terms "treat," "treating," and "treatment," as used herein, refer to therapeutic measures described herein. The methods of treatment employ administration to a patient (such as a human) the combination disclosed herein in order to cure, delay, reduce the severity of, or ameliorate one or more symptoms of the disease or disorder or recurring disease or disorder, or in order to prolong the survival of a patient beyond that expected in the absence of such treatment.

The terms "effective amount" or "therapeutically effective amount" are used interchangeably and refer to an amount of formulation effective to alleviate or ameliorate one or more symptom(s) of the disease or disorder (e.g., NASH) or to prolong the survival of the patient being treated. Determination of a therapeutically effective amount is well within the capability of those skilled in the art, especially in light of the detailed disclosure provided herein. Therapeutically effective dosages may be determined by using in vitro and in vivo methods.

In one embodiment, a method for treating a patient having NASH is provided comprising: (a) determining the serum Pro-C3 level in a blood sample from the patient and (b) administering to the patient a modified FGF-21 in an amount and with a frequency sufficient to treat NASH, if the serum Pro-C3 level is greater than about 10 ng/ML prior to administration to the patient of the modified FGF-21.

In another embodiment, a method for treating a patient having NASH who has been determined to have a serum Pro-C3 level greater than about 10 ng/ML is provided, the method comprising administering to the patient a modified FGF-21 in an amount and with a frequency sufficient to treat NASH.

In another embodiment, a method for treating a patient with NASH with modified FGF-21 is provided, wherein the patient has a serum Pro-C3 level greater than 10 ng/ML prior to treatment, wherein the method comprises administering to the patient a modified FGF-21 in an amount and with a frequency sufficient to treat NASH.

In another embodiment, a method for treating a patient having NASH is provided, wherein the method comprises: (1) obtaining or having obtained a blood sample from the patient, (2) determining or having determined a serum Pro-C3 level in the blood sample that is greater than 10 ng/ML, and (3) administering to the patient a modified FGF-21 in an amount and with a frequency sufficient to treat NASH after a serum Pro-C3 level has been determined.

In another embodiment a method for treating a patient having NASH is provided, comprising: (a) determining the serum Pro-C3 level in a blood sample from the patient and (b) administering to the patient a modified FGF-21 in an amount and with a frequency sufficient to treat NASH, if the serum Pro-C3 level is greater than about 10 ng/ML, wherein the modified FGF-21 comprises the polypeptide of SEQ ID NO:1, except that an amino acid in the polypeptide is substituted by a non-naturally encoded amino acid, wherein: (a) said non-naturally encoded amino acid is at a position corresponding to residue 108 of SEQ ID NO:1; (b) said non-naturally encoded amino acid comprises para-acetyl phenylalanine linked to a polymer comprising a poly(ethylene glycol).

In another embodiment a method for treating a patient having NASH is provided, comprising: (a) determining the serum Pro-C3 level in a blood sample from the patient and (b) administering to the patient a modified FGF-21 in an amount and with a frequency sufficient to treat NASH, if the serum Pro-C3 level is greater than about 10 ng/ML, wherein the modified FGF-21 comprises the polypeptide of SEQ ID NO:1 except that the amino acid at position 108 of SEQ ID NO:1 is substituted by a non-naturally encoded amino acid, wherein: (a) said non-naturally encoded amino acid comprises para-acetyl phenylalanine, and (b) said non-naturally encoded amino acid is linked to a polymer comprising a poly(ethylene glycol) having an average molecular weight of about 30 kDa.

In another embodiment, a method for treating a patient having NASH is provided, comprising: (a) determining the serum Pro-C3 level in a blood sample from the patient and (b) administering to the patient a modified FGF-21 in an amount and with a frequency sufficient to treat NASH, if the serum Pro-C3 level is greater than about 10 ng/ML, wherein the modified FGF-21 consists of or comprises SEQ ID NO:2.

In another embodiment, a method for treating a patient having NASH who has been determined to have a serum Pro-C3 level greater than about 10 ng/ML is provided, the method comprising administering to the patient a modified FGF-21 in an amount and with a frequency sufficient to treat NASH, wherein the modified FGF-21 comprises the polypeptide of SEQ ID NO:1, except that an amino acid in the polypeptide is substituted by a non-naturally encoded amino acid, wherein: (a) said non-naturally encoded amino acid is at a position corresponding to residue 108 of SEQ ID NO:1; (b) said non-naturally encoded amino acid comprises para-acetyl phenylalanine linked to a polymer comprising a poly(ethylene glycol).

In another embodiment, a method for treating a patient having NASH who has been determined to have a serum Pro-C3 level greater than about 10 ng/ML is provided, the method comprising administering to the patient a modified FGF-21 in an amount and with a frequency sufficient to treat NASH, wherein the modified FGF-21 comprises the polypeptide of SEQ ID NO:1 except that the amino acid at position 108 of SEQ ID NO:1 is substituted by a non-naturally encoded amino acid, wherein: (a) said non-naturally encoded amino acid comprises para-acetyl phenylalanine, and (b) said non-naturally encoded amino acid is linked to a polymer comprising a poly(ethylene glycol) having an average molecular weight of about 30 kDa.

In another embodiment, a method for treating a patient having NASH who has been determined to have a serum Pro-C3 level greater than about 10 ng/ML is provided, the method comprising administering to the patient a modified FGF-21 in an amount and with a frequency sufficient to treat NASH, wherein the modified FGF-21 consists of or comprises SEQ ID NO:2.

In another embodiment, a method for treating a patient having NASH who has been determined to have a serum Pro-C3 level greater than about 10 ng/ML is provided, the method comprising administering to the patient a modified FGF-21 in an amount and with a frequency sufficient to treat NASH, wherein the modified FGF-21 consists of or comprises SEQ ID NO:2, wherein the non-naturally encoded amino acid in SEQ ID NO: 2 is linked to a polymer comprising a poly(ethylene glycol) having an average molecular weight of about 30 kDa.

In another embodiment, a modified FGF-21 for use in a method of treating NASH in a patient is provided, wherein the method comprises administering to the patient a modified FGF-21 in an amount and with a frequency sufficient to treat NASH, wherein the patient has been determined to have a serum Pro-C3 level greater than 10, 15 or 20 ng/ML.

The modified FGF-21 can be administered to a subject, e.g., a human patient, using a variety of methods that depend, in part, on the route of administration. The route can be, e.g., intravenous injection or infusion (IV), subcutaneous injection (SC), intraperitoneal (IP) injection, or intramuscular injection.

Administration can be achieved by, e.g., local infusion, injection, or by means of an implant. The implant can be of a porous, non-porous, or gelatinous material, including membranes, such as sialastic membranes, or fibers. The implant can be configured for sustained or periodic release of the composition to the patient. See, e.g., U.S. patent publication no. 20080241223; U.S. Pat. Nos. 5,501,856; 4,863,457; and 3,710,795; and European patent nos. EP488401 and EP430539, the disclosures of each of which are incorporated herein by reference in their entirety. The composition can be delivered to the patient by way of an implantable device based on, e.g., diffusive, erodible or convective systems, e.g., osmotic pumps, biodegradable implants, electrodiffusion systems, electroosmosis systems, vapor pressure pumps, electrolytic pumps, effervescent pumps, piezoelectric pumps, erosion-based systems, or electromechanical systems.

A suitable dose of a modified FGF-21 which is capable of treating NASH in a patient, can depend on a variety of factors including, e.g., the age, sex, and weight of a patient to be treated. Other factors affecting the dose administered to the patient include, e.g., the severity of the disease. Other factors can include, e.g., other medical disorders concurrently or previously affecting the patient, the general health of the patient, the genetic disposition of the patient, diet, time of administration, rate of excretion, drug combination, and any other additional therapeutics that are administered to the patient. It should also be understood that a specific dosage and treatment regimen for any particular patient will depend upon the judgment of the treating medical practitioner (e.g., doctor or nurse).

In one embodiment, the modified FGF-21 is administered at a fixed dose. As used herein, the terms "fixed dose", "flat dose", and "flat-fixed dose" are used interchangeably and refer to a dose that is administered to a patient without regard for the weight or body surface area (BSA) of the patient. The fixed or flat dose is therefore not provided as a mg/kg dose, but rather as an absolute amount of the agent.

In one embodiment, the modified FGF-21 is administered at a fixed weekly dose. In another embodiment, the modified FGF-21 is administered at a dose of about 10 mg once weekly. In another embodiment, the modified FGF-21 is administered at a dose of about 11 mg once weekly. In another embodiment, the modified FGF-21 is administered at a dose of about 12 mg once weekly. In another embodiment, the modified FGF-21 is administered at a dose of about 13 mg once weekly. In another embodiment, the modified FGF-21 is administered at a dose of about 14 mg once weekly. In another embodiment, the modified FGF-21 is administered at a dose of about 15 mg once weekly. In another embodiment, the modified FGF-21 is administered at a dose of about 16 mg once weekly. In another embodiment, the modified FGF-21 is administered at a dose of about 17 mg once weekly. In another embodiment, the modified FGF-21 is administered at a dose of about 18 mg once weekly. In another embodiment, the modified FGF-21 is administered at a dose of about 19 mg once weekly. In another embodiment, the modified FGF-21 is administered at a dose of about 20 mg once weekly. In another embodiment, the modified FGF-21 is administered at a dose of about 21 mg once weekly. In another embodiment, the modified FGF-21 is administered at a dose of about 22 mg once weekly. In another embodiment, the modified FGF-21 is administered at a dose of about 23 mg once weekly. In another embodiment, the modified FGF-21 is administered at a dose of about 24 mg once weekly. In another embodiment, the modified FGF-21 is administered at a dose of about 25 mg once weekly. In another embodiment, the modified FGF-21 is administered at a dose of about 26 mg once weekly. In another embodiment, the modified FGF-21 is administered at a dose of about 27 mg once weekly. In another embodiment, the modified FGF-21 is administered at a dose of about 28 mg once weekly. In another embodiment, the modified FGF-21 is administered at a dose of about 29 mg once weekly. In another embodiment, the modified FGF-21 is administered at a dose of about 30 mg once weekly. In another embodiment, the modified FGF-21 is administered at a dose of about 35 mg once weekly. In another embodiment, the modified FGF-21 is administered at a dose of about 40 mg once weekly. In another embodiment, the modified FGF-21 is administered at a fixed daily dose. In some embodiments, the modified FGF-21 is administered at a dose of about 5 mg once daily, about 6 mg once daily, about 7 mg once daily, about 8 mg once daily, about 9 mg once daily, about 10 mg once daily, about 11 mg once daily, about 12 mg once daily, about 13 mg once daily, about 14 mg once daily, about 15 mg once daily, about 16 mg once daily, about 17 mg once daily, about 18 mg once daily, about 19 mg once daily, about 20 mg once daily, about 25 mg once daily, or about 30 mg once daily. In one embodiment, the modified FGF-21 is administered at a dose of about 10 mg once daily. In another embodiment, the modified FGF-21 is administered at a dose of about 15 mg once daily. In another embodiment, the modified FGF-21 is administered at a dose of about 20 mg once daily.

In some embodiments, the modified FGF-21 is administered at a fixed dose for 1 month, 2 months, 3 months, 4 months, 5 months, 6 months, 7 months, 8 months, 9 months, 10 months, 11 months, or 12 months.

A pharmaceutical composition can include a therapeutically effective amount of a modified FGF-21 (e.g., such as BMS-986036). Such effective amounts can be readily determined by one of ordinary skill in the art based, in part, on the effect of the modified FGF-21 or the combinatorial effect of the modified FGF-21 and one or more additional active agents, if more than one agent is used. A therapeutically effective amount of a modified FGF-21 can also vary according to factors such as the disease state, age, sex, and weight of the individual, and the ability of the modified FGF-21 (and one or more additional active agents) to elicit a desired response in the individual, e.g., amelioration of at least one condition parameter, e.g., amelioration of at least one symptom of NASH. For example, a therapeutically effective amount of a modified FGF-21 can inhibit (lessen the severity of or eliminate the occurrence of) of any one of the symptoms of NASH. A therapeutically effective amount is also one in which any toxic or detrimental effects of the composition are outweighed by the therapeutically beneficial effects.

Toxicity and therapeutic efficacy of a modified FGF-21 can be determined by known pharmaceutical procedures in cell cultures or experimental animals. These procedures can be used, e.g., for determining the $LD_{50}$ (the dose lethal to 50% of the population) and the EDso (the dose therapeutically effective in 50% of the population). The dose ratio between toxic and therapeutic effects is the therapeutic index and it can be expressed as the ratio $LD_{50}/ED_{50}$.

Compositions that exhibit high therapeutic indices are preferred. While compositions that exhibit toxic side effects may be used, care should be taken to design a delivery system that targets such compounds to the site of affected tissue and to minimize potential damage to normal cells and, thereby, reduce side effects.

5. Methods of Monitoring Responsiveness

Also provided are methods for monitoring responsiveness of a patient having NASH to treatment with a modified FGF-21, the method comprising: determining the serum Pro-C3 level in a blood sample from the patient obtained during or after treatment, wherein: a decreased serum Pro-C3 level in the blood sample from the patient obtained during or after treatment, as compared to the serum Pro-C3 level in a blood sample from the patient obtained prior to treatment with the modified FGF-21, indicates that the patient is responsive to treatment with the modified FGF-21.

In another embodiment, a method for monitoring responsiveness of a patient having NASH to treatment with a modified FGF-21 is provided, the method comprising: determining the serum Pro-C3 level in a blood sample from the patient obtained during or after treatment, wherein: a decreased serum Pro-C3 level in the blood sample from the patient obtained during or after treatment, as compared to the serum Pro-C3 level in a blood sample from the patient obtained prior to treatment with the modified FGF-21, indicates that the patient is responsive to treatment with the modified FGF-21, wherein the modified FGF-21 comprises the polypeptide of SEQ ID NO:1, except that an amino acid in the polypeptide is substituted by a non-naturally encoded amino acid, wherein: (a) said non-naturally encoded amino acid is at a position corresponding to residue 108 of SEQ ID NO:1; (b) said non-naturally encoded amino acid comprises para-acetyl phenylalanine linked to a polymer comprising a poly(ethylene glycol)

In another embodiment, a method for monitoring responsiveness of a patient having NASH to treatment with a modified FGF-21 is provided, the method comprising: determining the serum Pro-C3 level in a blood sample from the patient obtained during or after treatment, wherein: a decreased serum Pro-C3 level in the blood sample from the patient obtained during or after treatment, as compared to the serum Pro-C3 level in a blood sample from the patient obtained prior to treatment with the modified FGF-21, indicates that the patient is responsive to treatment with the modified FGF-21, wherein the modified FGF-21 comprises the polypeptide of SEQ ID NO:1 except that the amino acid at position 108 of SEQ ID NO:1 is substituted by a non-naturally encoded amino acid, wherein: (a) said non-naturally encoded amino acid comprises para-acetyl phenylalanine, and (b) said non-naturally encoded amino acid is linked to a polymer comprising a poly(ethylene glycol) having an average molecular weight of about 30 kDa.

In another embodiment, a method for monitoring responsiveness of a patient having NASH to treatment with a modified FGF-21 is provided, the method comprising: determining the serum Pro-C3 level in a blood sample from the patient obtained during or after treatment, wherein: a decreased serum Pro-C3 level in the blood sample from the patient obtained during or after treatment, as compared to the serum Pro-C3 level in a blood sample from the patient obtained prior to treatment with the modified FGF-21, indicates that the patient is responsive to treatment with the modified FGF-21, wherein the modified FGF-21 consists of or comprises SEQ ID NO:2.

In another embodiment, a modified FGF-21 for use in a method of monitoring responsiveness of a patient having NASH to treatment with a modified FGF-21 is provided, wherein a decreased serum Pro-C3 level in a blood sample from the patient obtained during or after treatment, as compared to a serum Pro-C3 level in a blood sample from the patient obtained prior to treatment with the modified FGF-21, indicates that the patient is responsive to treatment with the modified FGF-21.

In one embodiment, a decrease in serum levels of Pro-C3 by at least 5 (e.g., at least 10, 15, 20, 25, 30, 35, 40, 45, 50, 55, 60, 65, or 70) % following administration of the modified FGF-21, indicates that the patient is responsive to treatment with the modified FGF-21.

In another embodiment, a decrease in serum levels of Pro-C3 to within 90 (e.g., 85, 80, 75, 70, 65, 60, 55, 50, 45, 40, 35, or 30) % of the Baseline serum level of Pro-C3 following administration of one or more doses of the modified FGF-21, indicates that the patient is responsive to treatment with the modified FGF-21.

6. Methods for Identifying Responders

Also provided are methods for identifying responder of a patient having NASH to treatment with a modified FGF-21. In one embodiment, the method comprises: determining the patient has a serum Pro-C3 level greater than about 10 ng/ML in a blood sample obtained prior to treatment, and identifying the patient as a responder to the treatment with the modified FGF-21, wherein the modified FGF-21 comprises the polypeptide of SEQ ID NO:1 except that the amino acid at position 108 of SEQ ID NO:1 is substituted by a non-naturally encoded amino acid, wherein: (a) said non-naturally encoded amino acid comprises para-acetyl phenylalanine, and (b) said non-naturally encoded amino acid is linked to a polymer comprising a poly(ethylene glycol) having an average molecular weight of about 30 kDa. In another embodiment, a method of identifying a patient having NASH that is suitable for treatment with a modified FGF-21 is provided, wherein the method comprises determining a serum Pro-C3 level in a blood sample from the patient using an in vitro assay, wherein the serum Pro-C3 level in the blood sample is greater than 10, 15 or 20 ng/ML. In some embodiments, the method comprises determining the patient has a serum Pro-C3 level greater than about 11 ng/ML, 12 ng/ML, 13 ng/ML, 14 ng/ML, 15 ng/ML, 16 ng/ML, 17 ng/ML, 18 ng/ML, 19 ng/ML, 20 ng/ML, 21 ng/ML, or 22 ng/ML, in a blood sample obtained from the patient prior to treatment.

7. Additional Agents/Therapies

In some embodiments, the modified FGF-21 can be administered to a patient as a monotherapy. Alternatively, as described above, the modified FGF-21 can be administered to a patient as a combination therapy with another treatment. For example, the combination therapy can include administering to the patient (e.g., a human patient) one or more additional agents that provide a therapeutic benefit to the patient who has NASH. In one embodiment, the modified FGF-21 is administered first in time and the one or more additional active agents are administered second in time. In some embodiments, the one or more additional active agents are administered first in time and the modified FGF-21 is administered second in time.

In some embodiments, the one or more additional therapeutic agents may be selected from anti-fibrotic agents, N-cadherin antagonist, anti-N cadherin antibody, small molecule N-cadherin antagonist, antagonistic N-cadherin fragment, anti-inflammatory agents, hepatoprotective agents suppressing renin-angiotensin system (RAS) system, probiotics, and polyunsaturated fatty acids (PUFAs). In some embodiments, the anti-fibrotic agent may be selected from nintedanib, Pirfenidone, LPA1 antagonists, LPA1 receptor antagonists, GLP1 analog, tralokinumab (IL-13, Astra7eneca), vismodegib (hedgehog antagonist, Roche), PRM-151 (pentraxin-2, TGF beta-1, Promedior), SAR-156597 (bispecific Mab IL-4&IL-13. Sanofi), simtuzumab (anti-lysyl oxidase-like 2 (anti-LOXL2) antibody, Gilead), CKD-942, PTL-202 (PDE inh./pentoxifylline/NAC oral control. release, Pacific Ther.), omipalisib (oral PI3K/mTOR inhibitor, GSK), IW-001 (oral sol. bovine type V collagen mod., ImmuneWorks), STX-100 (integrin alpha V/beta-6 ant, Stromedix/Biogen), Actimmune (IFN gamma), PC-SOD (midismase; inhaled, LTT Bio-Pharma/CKD Pharm), lebrikizumab (anti-IL-13 SC humanized mAb, Roche), AQX-1125 (SHIP1 activator, Aquinox), CC-539 (JNK inhibitor, Celgene), FG-3019 (FibroGen), and SAR-100842 (Sanofi). In some embodiments, the hepatoprotective agent may be ursodeoxycholic acid (UDCA) or obeticholic acid (OCA or INT-747, Intercept).

8. Outcomes

Patients treated according to the methods disclosed herein preferably experience improvement in at least one sign of NASH.

In one embodiment, the treatment methods described herein result in a decrease in Pro-C3 levels (e.g., at least 10, 15, 20, 25, 30, 35, 40, 45, 50, 55, 60, 65, or 70%) compared to pre-treatment Pro-C3 levels. In another embodiment, the treatment methods described herein result in a decrease in Pro-C3 levels (e.g., by at least about 1.5-fold, 2-fold, 2.5-fold, or 3-fold compared to pre-treatment Pro-C3 levels).

In another embodiment, the treatment methods described herein produce a shift toward normal levels of Pro-C3 (e.g., to within 50 (e.g., 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1) % above the normal serum level of Pro-C3).

In another embodiment, the treatment methods described herein result in a reduction in liver stiffness in a patient, as assessed by magnetic resonance elastography (MRE). For example, in one embodiment, treatment with a modified FGF-21 results in a reduction in liver stiffness in the patient compared to the patient's liver stiffness prior to treatment, wherein liver stiffness is assessed by MRE. In another embodiment, treatment with a modified FGF-21 results in a 15% or greater (e.g., 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 50%, 55%, 60%, 65%, 70%, 75% or greater) reduction in liver stiffness in the patient compared to the patient's liver stiffness prior to treatment, wherein liver stiffness is assessed by MRE.

In another embodiment, the treatment methods described herein result in a reduction in hepatic fat fraction in a patient. For example, in one embodiment, treatment with a modified FGF-21 results in a reduction in hepatic fat fraction in the patient compared to the patient's hepatic fat fraction prior to treatment, wherein hepatic fat fraction is as assessed by magnetic resonance imaging-estimated proton density fat fraction (MRI-PDFF). In another embodiment, treatment with the modified FGF-21 results in a 30% or greater (e.g., 31%, 32%, 33%, 34%, 35%, 36%, 37%, 38%, 39%, 40%, 41%, 42%, 43%, 44%, 45%, 46%, 47%, 48%, 49% 50%, 51%, 52%, 53%, 54%, 55%, 56%, 57%, 58%, 59%, 60%, 65%, 70%, 75% or greater) reduction in hepatic fat fraction in the patient compared to the patient's hepatic fat fraction prior to treatment, wherein hepatic fat fraction is assessed by MRI-PDFF. In another embodiment, the patient's hepatic fat fraction is decreased by at least 5 (e.g., at least 10, 15, 20, 25, 30, 35, 40, 45, 50, 55, 60, 65, or 70) % following administration of the modified FGF-21 to the patient, compared to the patient's hepatic fat fraction prior to treatment, as assessed by MRI-PDFF. In another embodiment, the patient's hepatic fat fraction is decreased by at least 20% following administration of the modified FGF-21 to the patient, compared to the patient's hepatic fat fraction prior to treatment, as assessed by MRI-PDFF. In another embodiment, the patient's hepatic fat fraction is decreased by at least 30% following administration of the modified FGF-21 to the patient, compared to the patient's hepatic fat fraction prior to treatment, as assessed by MRI-PDFF. In another embodiment, the patient's hepatic fat fraction is decreased to within 90 (e.g., 85, 80, 75, 70, 65, 60, 55, 50, 45, 40, 35, or 30) % of the patient's pre-treatment (prior to treatment) baseline serum level of hepatic fat fraction following administration of the modified FGF-21.

In another embodiment, the treatment methods described herein result in a reduction in live stiffness, a reduction in hepatic fat fraction, and/or a decrease in serum Pro-C3 levels in a patient. In another embodiment, treatment with a modified FGF-21 results in a reduction in liver stiffness in the patient compared to the patient's liver stiffness prior to treatment, and a decrease in serum Pro-C3 levels in the patient compared to the patient's serum Pro-C3 levels prior to treatment, wherein liver stiffness is assessed by MRE, and wherein the patient has been determined to have a serum Pro-C3 level greater than 10, 15 or 20 ng/ML prior to treatment with the modified FGF-21. In another embodiment, the treatment methods described herein produces at least one therapeutic effect selected from the group consisting of a reduction or cessation in fatigue, malaise, weight loss, and/or right upper quadrant abdominal discomfort in the patient.

9. Kits

Also provided are kits comprising various reagents and materials useful for carrying out the methods described herein. The procedures for measuring, diagnosing, evaluating, and/or assessing described herein may be performed by diagnostic laboratories, experimental laboratories, or individual practitioners. The invention provides kits which can be used in any or all of these settings. In some embodiments, the kits described herein comprise materials and reagents for, among other things, characterizing or processing biological samples (e.g., blood), measuring Pro-C3 biomarker levels (e.g., protein or nucleic acid levels), monitoring treatment response in a patient according to the methods provided herein. In certain embodiments, an inventive kit comprises at least one or more reagents that specifically detect serum protein levels of Pro-C3 and, optionally, instructions for using the kit.

In some embodiments, the kits may include suitable control samples (e.g., biological samples from normal healthy individuals or a solution comprising a known, control amount of a particular analyte of interest, such as Pro-C3). In some embodiments, kits of the invention may include instructions for using the kit according to one or more methods described herein and may comprise instructions for processing the biological sample (e.g., blood) obtained from the patient and/or for performing the test or instructions for interpreting the results.

While the present disclosure has been described with reference to the specific embodiments thereof, it should be understood by those skilled in the art that various changes may be made and equivalents may be substituted without departing from the true spirit and scope of the disclosure. In addition, many modifications may be made to adapt a particular situation, material, composition of matter, process, or process step or steps, to the objective, spirit and scope of the present disclosure. All such modifications are intended to be within the scope of the disclosure.

The following example is intended to illustrate, not limit, the invention.

EXAMPLES

Example 1: A Randomized, Double-Blind, Placebo-Controlled, Parallel Group, Multiple Dose Study to Evaluate the Safety, Pharmacokinetics and Pharmacodynamic Effects of BMS-986036 in Adults with Nonalcoholic Steatohepatitis (NASH)

The objectives of this study were to assess the effect of 16 weeks of daily or weekly doses of BMS-986036 (a modified FGF21 comprising the amino acid sequence of SEQ ID NO:2, in which the pAF is linked to a 30 kD PEG) on safety, tolerability and change in hepatic fat fraction (%) by MRI in patients with NASH and to assess the pharmacokinetics and immunogenicity of BMS-986036 in patients with NASH. The objectives also included assessing the effect of daily or weekly doses of BMS-986036 on Liver stiffness by MRE at 16 weeks, Body composition by dual-energy X-ray absorptiometry (DXA), BMS-986036 urinary concentration, Body weight and waist circumference, ALT (alanine aminotransferase) and AST (aspartate aminotransferase) levels, Glucose homeostasis and insulin sensitivity, Fasting lipids, Bone homeostasis, exploratory biomarkers associated with the risk of disease progression and complications, and Calculated indices related to NASH.

A. Methods

Subjects underwent screening evaluations to determine eligibility within 42 days prior to randomization. Eligible subjects were randomized to one of three parallel treatment groups and self-administered double-blind treatment, once daily or once weekly for 16 weeks. Included in the study were male and female subjects aged 21 to 75 years with a BMI of ≥25 kg/m$^2$ with a liver biopsy performed within 1 year of Screening (or between Screening and Lead-in) with documented results of NASH with NASH CRN fibrosis stage 1-3 and a hepatic fat fraction (%) ≥10% by magnetic resonance imaging-proton density fat fraction (MRI-PDFF). Patients were excluded if they had evidence of a medical condition contributing to chronic liver disease other than NASH, evidence of cirrhosis, decompensated liver disease, glycated haemoglobin (Hb$_{A1c}$) ≥9.5%, recent drug or alcohol abuse or significant alcohol consumption, bone trauma, fracture, or bone surgery within 8 weeks of screening, or any clinically significant deviation from normal in physical examination or clinical laboratory determinations beyond what is consistent with the target patient population.

Eligible patients were randomised (1:1:1) on Day 1 using the Interactive Voice Response System (IVRS) to one of the following groups: BMS-986036 10 mg QD, BMS-986036 20 mg QW, or placebo QD. Patients were stratified by diagnosis of T2DM status based on current American Diabetes Association criteria (see American Diabetes Association, "Classification and diagnosis of diabetes", Sec. 2. Diabetes Care 2015; 38(Suppl 1): S8). Blinded treatments were supplied in numbered kits for administration in an outpatient setting. At all study visits when study drugs were dispensed, each patient was randomly assigned a kit number by the IVRS. Kit numbers corresponded to the numbers printed on the packages and kits containing study drug. Each kit contained 8 vials to support one week of dosing. 2 vials were designated for Day 1 and 1 vial was provided for each of Days 2-7.

Clinic visits were scheduled approximately every 2 weeks initially, and then monthly, to collect safety, PK, and PD measures (Table 1).

TABLE 1

| Study Design Schematic Visit Days | | | | | | | | | | | |
|---|---|---|---|---|---|---|---|---|---|---|---|
| D −42 | D −7 | D 1 | D 15 | D 29 | D 43 | D 57 | D 86 | D 112 | D 142 | D 292 |
| Screening 5 weeks | Lead-in 1 week Placebo | | On treatment 4 months Treatment A: 10 mg QD Treatment B: 20 mg QW Treatment C: Placebo QD | | | | | | | Follow-up | |

QD = Once daily;
QW = Once weekly;
D = Day

Prior to randomisation, eligible patients completed a 7-day study skills lead-in period consisting of daily placebo injections (Day −7 to Day −1). Injections were self-administered subcutaneously in the abdomen and patients were trained to rotate injection sites relative to the umbilicus. After randomisation on Day 1, patients self-administered double-blind treatment subcutaneously once daily for 16 weeks as set forth in Table 2. For all treatments, on Day 1 of each treatment week, two 1-mL injections were administered concurrently and on Days 2 to 7, one 1-mL injection was administered. For the BMS-986036 10 mg QD group, the two injections on Day 1 consisted of one active dose and one placebo to maintain the blind between daily and weekly treatment groups. For the BMS-986036 20 mg QW group, on Days 2-7, the daily injection was placebo to maintain the blind between daily and weekly treatment groups.

TABLE 2

Treatment Administration

| | Treatment | Solution strength | Number and volume of injections | |
|---|---|---|---|---|
| | | | Day 1 of each treatment week | Days 2-7 of each treatment week |
| Lead-in phase | Placebo QD | N/A | 2 × 1 mL | 1 × 1 mL, daily |
| A | BMS-986036 10 mg QD | 10 mg/mL | 2 × 1 mL | 1 × 1 mL, daily |
| B | BMS-986036 20 mg QW | 10 mg/mL | 2 × 1 mL | 1 × 1 mL, daily |
| C | Placebo QW | N/A | 2 × 1 mL | 1 × 1 mL, daily |

N/A = not applicable. QD = once daily. QW = once weekly.

On-treatment clinic visits were scheduled for Days 1, 15, 29, 43, 57, 86 and 112. Post-study follow-up visits were scheduled for Days 142 and 292. Physical examinations, vital sign measurements, and clinical laboratory evaluations were performed at screening, at each treatment visit, and at the Day 142 follow-up visit. Twelve-lead electrocardiograms (ECGs) were performed at screening, Day 1, Day 112, and at follow-up. Due to the association of FGF21 and bone loss observed in mouse models (see, e.g., Wei W, et al. Proc Natl Acad Sci USA 2012; 109(8): 3143-8), dual emission X-ray absorptiometry (DXA) was performed to monitor bone mineral density (BMD) and body composition at screening, end of treatment, and 6 months after the end of treatment. MRI-PDFF was performed at screening, and on Day 57 and the end of treatment. At a subset of facilities with the appropriate hardware and software, magnetic resonance elastography (MRE) was conducted at screening and at the end of treatment. Fasting lipids (LabCorp, Burlington, N.C.), adiponectin (Myriad RBM, Austin, Tex.), and insulin (LabCorp) levels were assessed on Days 1, 29, 57, 86, 112, and 142. PRO-C3 levels were assessed on Days 1, 57, and 112 (Nordic Bioscience, Herlev, Denmark). Adverse event (AE) data were collected at every time point throughout the study and at follow-up visits. Patients were monitored for injection site reactions from Day −7 through the end of the post-study follow-up visits. The Draize scale for erythema and oedema was used as a guide for reporting injection site AEs (see Haschek W, et al. "Evaluation of Cutaneous Toxicity" In: Fundamentals of Toxicologic Pathology. Second ed. Academic Press; 2009. p. 156). Immunogenicity to study drug and endogenous FGF21 was assessed pre-dose and on Days 15, 29, 57, 86, 112, 142, and 292. In addition, immunogenicity assessments were also done approximately every 6-8 weeks between Days 142 and 292 or up to 12 months after Day 142.

Primary endpoints were safety, tolerability, and absolute change in hepatic fat fraction by MRI-PDFF in NASH patients treated with 16 weeks of QD or QW doses of BMS-986036. Secondary endpoints included pharmacokinetics and immunogenicity. Exploratory endpoints included change in liver stiffness as measured by MRE at 16 weeks, body composition by DXA, alanine aminotransferase (ALT) and aspartate aminotransferase (AST) levels, adiponectin, fasting lipids, and PRO-C3. Post hoc endpoints included relative improvement in hepatic fat fraction measured by MRI-PDFF, liver stiffness measured by MRE, and PRO-C3.

For the primary endpoint, with 27 patients per treatment group with post-baseline measurements, it was estimated that there was 82% power to detect a difference of 5% in mean change from baseline at Week 16 in hepatic fat fraction between each of the 2 doses of BMS-986036 and placebo at a one-sided significance level of 0-05. These calculations assumed that the hepatic fat fraction change from baseline is normally distributed with a standard deviation of no greater than 7% as estimated from data reported in a similar population (see Le T A, et al., Hepatology 2012; 56(3): 922-32 and Patel N S, et al., Clin Gastroenterol Hepatol 2015; 13(3): 561-8. To allow for about 10% of patients to dropout, it was planned to randomise approximately 30 patients per treatment group.

To evaluate the primary endpoint, a longitudinal repeated measures analysis was used to analyse the change in hepatic fat fraction at Week 16 from baseline in treated patients with both a baseline and at least one post-baseline measurement. The model included treatment group, week and treatment-by-week interactions as main effects and baseline hepatic fat fraction (%) and baseline diabetic status as covariates. An unstructured covariance matrix was used to represent the correlation of the repeated measures within each subject. The model provided point estimates, standard errors and 2-sided 90% confidence intervals for mean change from baseline within and between treatments. For exploratory endpoints, descriptive statistics are provided by treatment and study day. Post hoc analyses were conducted using Fisher's Exact test and not adjusted for multiple comparisons. All recorded adverse events were listed and tabulated by system organ class, preferred term, and treatment group. Any significant physical examination findings and clinical laboratory results were listed. A pre-specified interim analysis was conducted after approximately 60 patients completed 8 weeks of treatment. If the mean change from baseline in hepatic fat fraction compared with placebo was at least −4.5%, then enrolment was stopped. Analyses consisted of summaries of available data without revealing the treatment assignment of individual patients. The results of the analysis were reviewed by a pre-specified panel of personnel and not revealed to other study personnel. All patients who were randomized and received study drug were included in the primary analyses.

Ctrough concentrations of BMS-986036 (Total and C-Terminal intact) were derived from serum concentration versus time data. MRE was performed at specific time points to evaluate potential changes in liver stiffness. DXA was performed at specific time points to evaluate potential changes in body composition. Blood and urine were collected to for exploratory biomarker analysis, including Pro-C3.

Baseline demographics and disease characteristics were generally comparable between treatment groups, as shown below in Table 3. Overall, 96% (72/75) of patients were white, 64% (48/75) were women, 37% (28/75) had T2DM, and 20% (15/75) had stage 3 fibrosis, as assessed by NASH CRN criteria. Across patient groups, baseline mean hepatic fat fraction measured by MRI-PDFF ranged from 18% to 21%, baseline mean liver stiffness assessed by MRE ranged from 3.1 to 3.5 kPa, and baseline mean NAS ranged from 4.0 to 4-4.

TABLE 3

Baseline Demographics and Disease Characteristics

| | | BMS-986036 | |
| --- | --- | --- | --- |
| Patient Characteristics | Placebo (n = 26) | 10 mg QD (n = 25) | 20 mg QW (n = 24) |
| Age, years, mean (SD) | 47 (12) | 52 (10) | 52 (12) |
| Male, n(%) | 10 (39) | 10 (40) | 7 (29) |
| Race, White, n (%) | 25 (96) | 24 (96) | 23 (96) |
| BMI, kg/m$^2$, mean (SD) | 37 (7) | 34 (4) | 35 (6) |
| Disease Characteristics | | | |
| T2DM, n (%) | 11 (42) | 9 (36) | 8 (33) |
| NAFLD activity score | 4 · 0 (1) | 4 · 4 (1) | 4 · 4 (1)* |
| NASH CRN Fibrosis, n (%) | | | |
| Stage 1 | 17 (65) | 10 (40) | 13 (54) |
| Stage 2 | 8 (31) | 6 (24) | 6 (25) |
| Stage 3 | 1 (4) | 9 (36) | 5 (21) |
| Liver, mean (SD) | | | |
| Hepatic fat fraction, % | 21 (7) | 18 (7) | 20 (6) |
| Liver stiffness, kPa | 3 · 1 (1 · 2) | 3 · 5 (1 · 4) | 3 · 4 (1 · 0) |
| ALT, U/L | 80 (51) | 66 (37) | 70 (33) |
| AST, U/L | 58 (49) | 48 (23) | 52 (22) |
| PRO-C3, ng/mL | 19 (12) | 19 (15) | 23 (15) |
| Metabolic, mean (SD) | | | |
| Triglycerides, mg/dL | 171 (75)* | 208 (110)* | 187 (55)† |
| LDL cholesterol, mg/dL | 128 (55) | 129 (38) | 120 (36) |
| HDL cholesterol, mg/dL | 50 (11) | 47 (10) | 45 (12) |
| HbA$_{1c}$, % | 6 · 0 (0 · 9) | 6 · 1 (0 · 9) | 6 · 2 (1 · 1) |

ALT = alanine aminotransferase. AST = aspartate aminotransferase. BMI = body mass index. HbA1c = glycated haemoglobin. HDL = high density lipoprotein. LDL = low density lipoprotein. MRI-PDFF = magnetic resonance imaging-proton density fat-fraction. NASH CRN = Non-Alcoholic Steatohepatitis Clinical Research Network. NAFLD = non-alcoholic fatty liver disease. PRO-C3 = N-terminal type III collagen propeptide. T2DM = type-2 diabetes mellitus. QD = once daily. QW = once weekly.
*n = 23; †n = 20.

Safety assessments included adverse events (AEs), serious adverse events (SAEs), and laboratory abnormalities and were based on medical review of AE reports and the results of vital sign measurements, ECG, physical examinations, and clinical laboratory tests.

B. Results 184 overweight or obese patients with NASH were enrolled in the study and 80 patients entered the lead-in phase. Of the 80 patients who entered the lead-in phase, seventy-five subjects were randomized and treated with BMS-986036 10 mg daily (25 subjects), BMS-986036 20 mg weekly (24 subjects), or placebo daily (26 subjects), as shown in FIG. 1.

The planned sample size was 30 patients per group. However, enrolment ended early due to a significant effect of BMS-986036 observed for the primary endpoint during the pre-planned interim analysis at treatment Week 8. A total of 71 of 75 patients (95%) completed the 16-week treatment period.

Figure 2A:
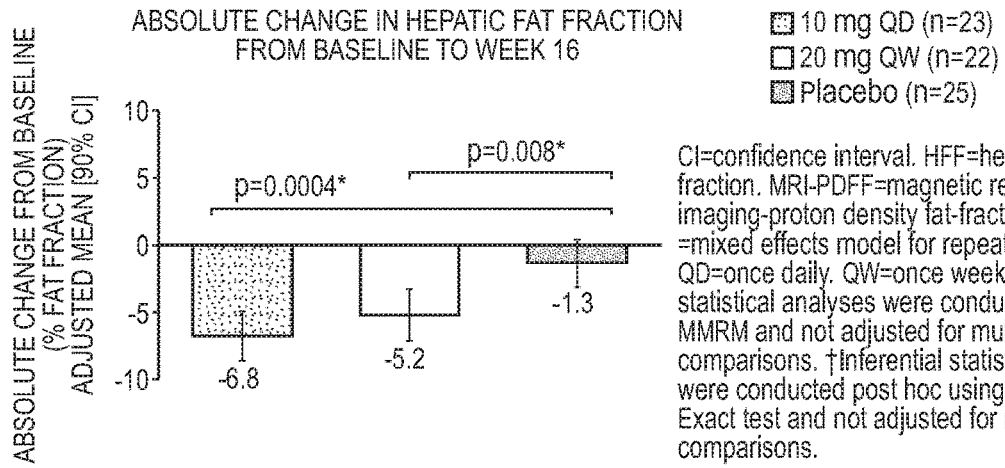
FIGS. 2A-2C depict the change in hepatic fat fraction measured by MRI-PDFF at week 16.
Figure 2B:
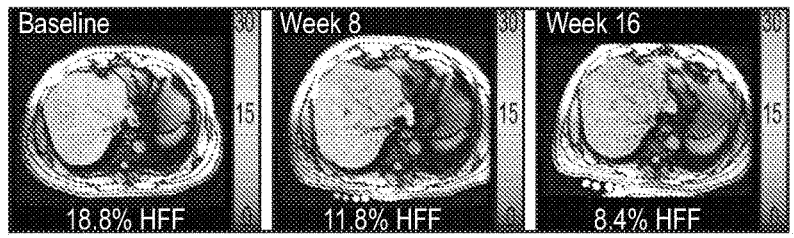
Figure 2C:
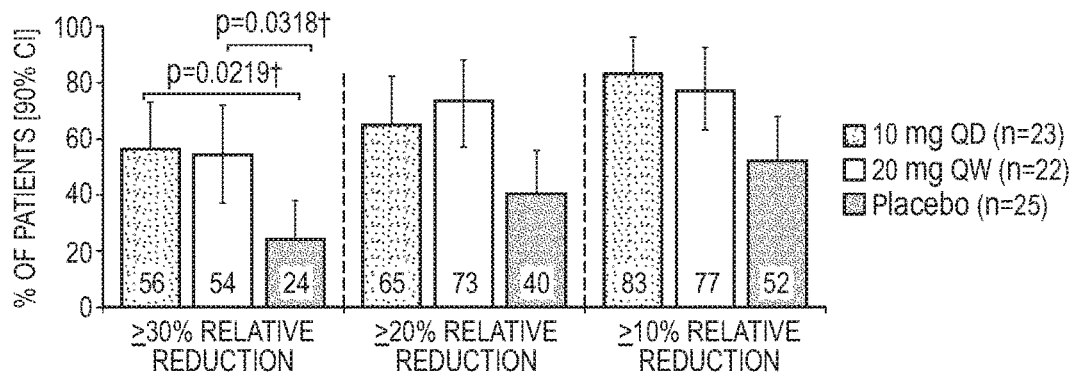

Hepatic Fat Fraction: After 16 weeks of treatment, mean hepatic fat fraction was significantly reduced in patients who received either 10 mg QD BMS-986036 (p=0.0004) or 20 mg QW BMS-986036 (p=0.008), compared with placebo (see FIG. 2A). Mean absolute reductions in hepatic fat fraction at Week 16 were −6.8% for the 10 mg QD dose panel (P=0.0004), −5.2% for the 20 mg QW dose panel (P=0.008), and −1.3% for the placebo panel. Mean absolute changes in hepatic fat fraction at Week 8 were −8.4%, −6.5%, and −1.3% for the 10 mg QD regimen, the 20 mg QW regimen, and the placebo regimen, respectively. A total of 68 subjects had MRI-PDFF data at both Baseline and Week 16. FIG. 2B shows the MRI-PDFF measurements of a patient who experienced a reduction in hepatic fat fraction following BMS-986036 treatment. Post hoc analyses showed that significantly more patients treated with BMS-986036 10 mg QD (p=0.03) or 20 mg QW (p=0.02) compared with placebo-treated patients had ≥30% relative reduction in hepatic fat fraction (FIG. 2C). A greater proportion of patients treated with BMS-986036 10 mg QD or 20 mg QW compared to placebo had ≥20% or ≥10% relative reductions in hepatic fat fraction. Table 4 presents percentage of patients with >=30% relative reduction from Baseline to Week 16 for hepatic fat fraction (56.5%, 54.5% and 24.0% for the 10 mg QD regimen, the 20 mg QW regimen, and the placebo regimen, respectively).

TABLE 4

Change from Baseline at Week 16 - Hepatic Fat Fraction

| Percent Change from Baseline at Week 16 | Number (%) of Subjects | | |
|---|---|---|---|
| | BMS 10 mg daily N = 25 | BMS 20 mg weekly N = 24 | Placebo daily N = 26 |
| HEPATIC FAT FRACTON >= 30% IMPROVEMENT | 13/23 (56.5) | 12/22 (54.5) | 6/25 (24.0) |
| 90% CI | (0.395, 0.735) | (0.370, 0.720) | (0.099, 0.380) |
| ODDS RATO (90% CI) | 4.12 (1.46, 11.59) | 3.80 (1.34, 10.79) | |
| P-VALUE (ONE-SIDED) | 0.0219 | 0.0318 | |

1. Baseline is defined as last non-missing result with a collection date-time less than the date-time of the first active dose of study medication.
2. Fisher exact test is conducted for this analysis.

PK: For each BMS-986036 treatment group of BMS-986036 10 mg daily and BMS-986036 20 mg weekly, the data demonstrated that steady state concentrations were achieved by the first week of treatment for C-terminal intact BMS-986036 and by the fourth week for Total BMS-986036 groups. Ctrough remained constant during the treatment period at 10 mg QD and 20 mg QW dosing group.

Figure 4:
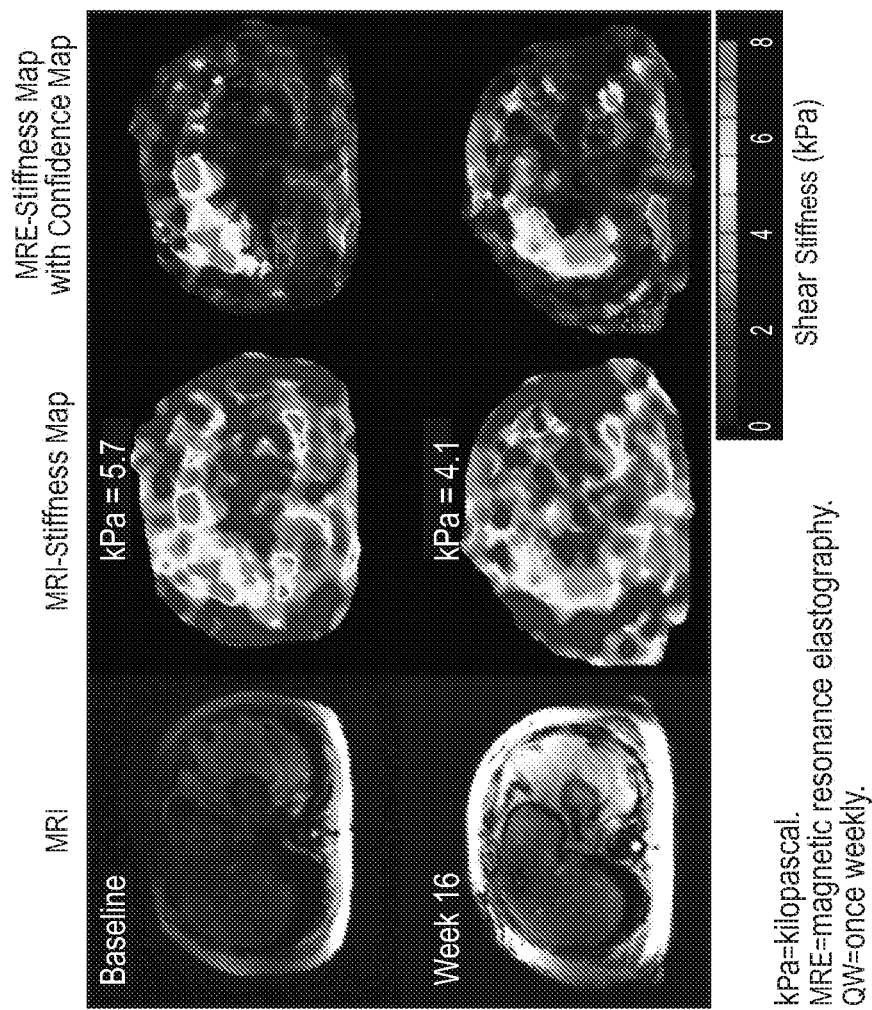
FIG. 4 is an MRE image from a patient treated with 20 mg QW BMS-986036.
Figure 5:
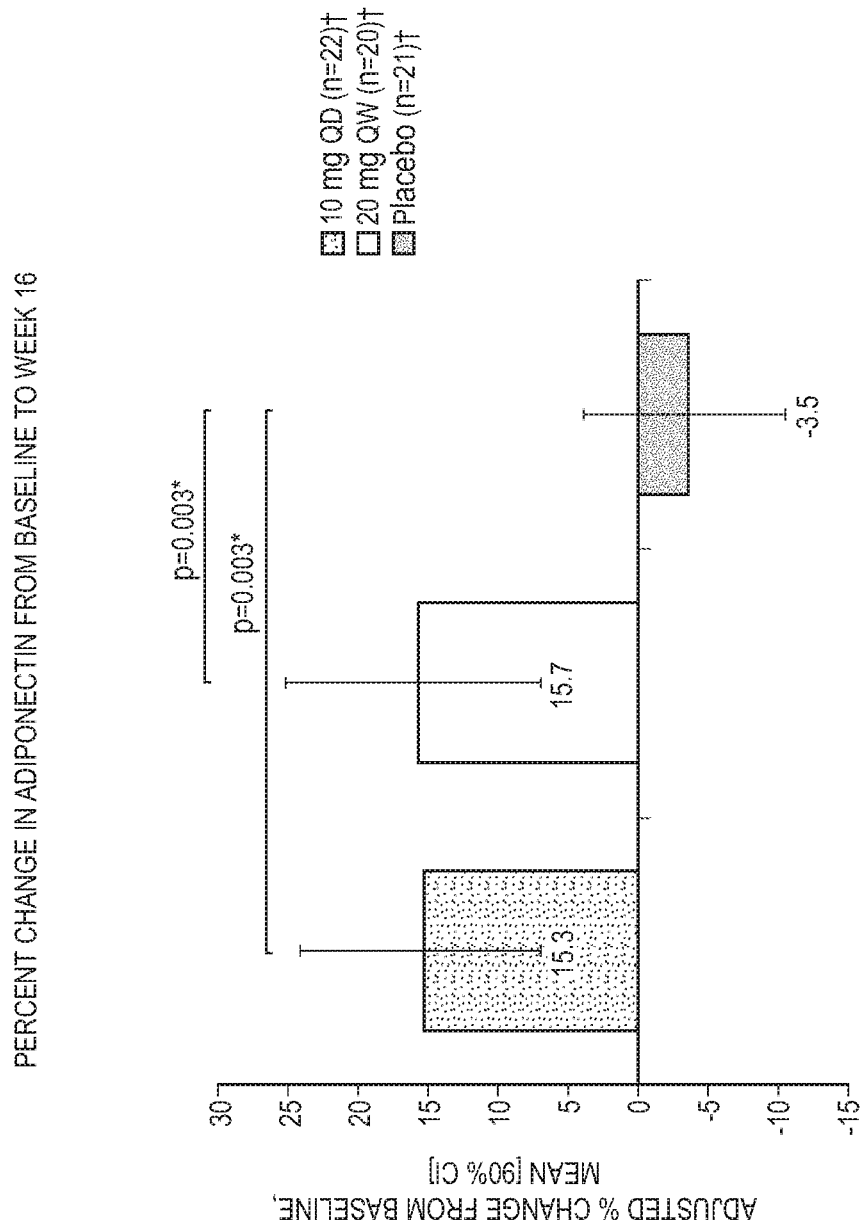
FIG. 5 shows the percent change in adiponectin from baseline to week 16.

MRE: Liver Stiffness: MRE was conducted to assess Liver Stiffness at the subset of imaging facilities where appropriate hardware and software was available. Therefore, the sample size for the liver stiffness (MRE) analysis was smaller than for other endpoints. Mean liver stiffness, as measured by MRE, decreased in all groups (see FIG. 3A). BMS-986036 10 mg QD and 20 mg QW groups compared with placebo had a greater percentage of patients with a ≥15% decrease in liver stiffness (see FIG. 3B). The percentages of subjects with ≥15% relative reduction were 36%, 33%, and 7% for the BMS-986036 10 mg QD regimen, the BMS986036 20 mg QW regimen, and the placebo regimen, respectively. MRE images from a patient who experienced a reduction in liver stiffness following BMS-986036 treatment are shown in FIG. 4.

ing treatment with BMS-986036 10 mg QD (p=0.003) and 20 mg QW (p=0.003) compared with placebo (see FIG. 5), with mean levels peaking at Day 29 and then trending downward toward Baseline. At Day 112, the adiponectin mean percent change from Baseline was 19% and 20% for the BMS-986036 20 mg QW and 10 mg QD treatment groups, respectively, compared with −1.1% for the placebo group, resulting in significant treatment differences (p=0.0071 for BMS-986036 10 QD, 0.0072 for BMS-986036 20 QW).

Figure 6B:
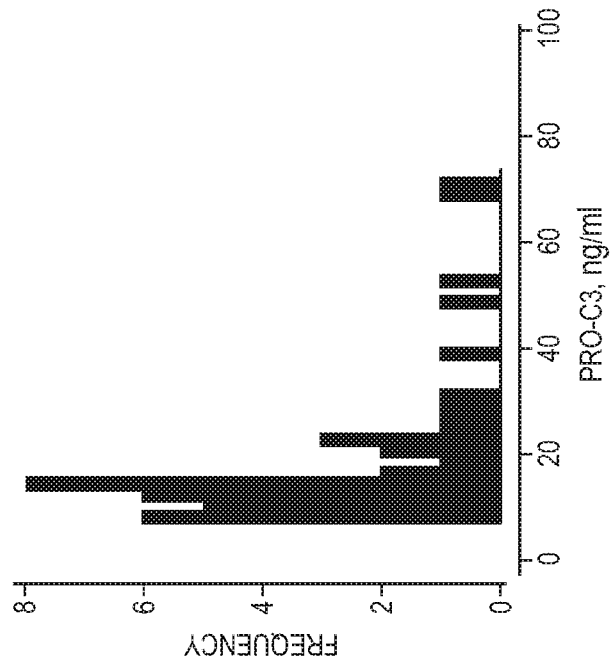
FIGS. 6A-6B show baseline Pro-C3 distribution among BMS-986036-treated patients.
Figure 6A:
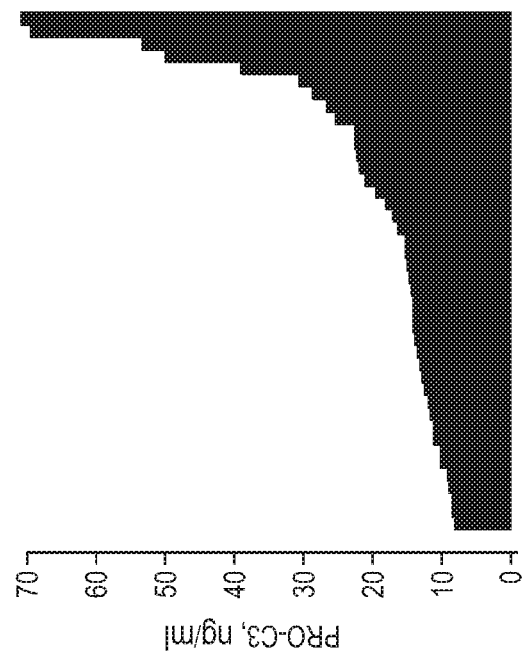
Figure 7A:
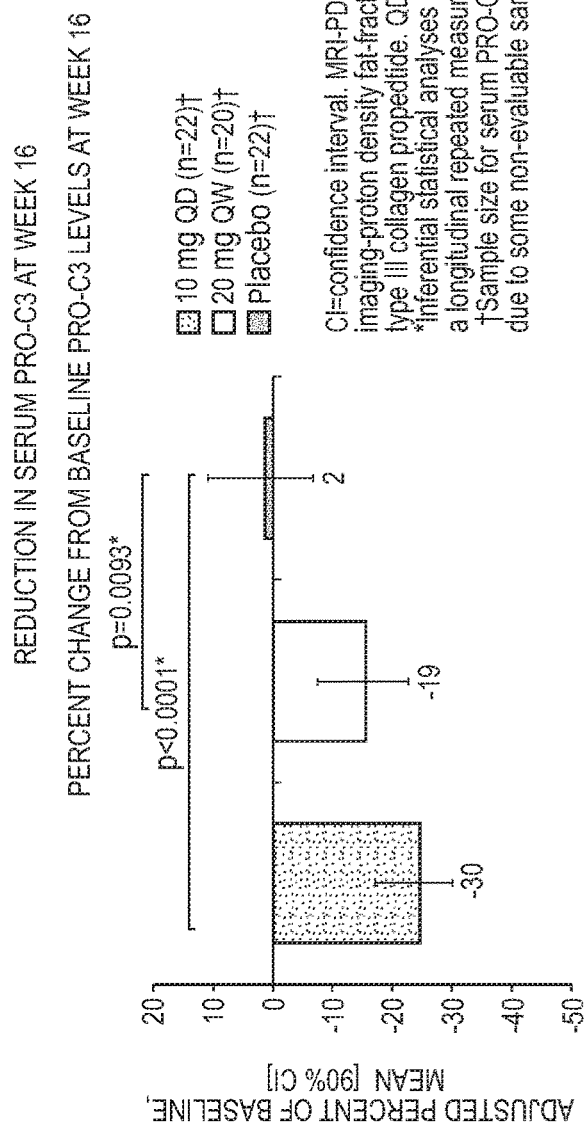
FIGS. 7A-7B show the reduction in Serum Pro-C3 at Week 16.
Figure 7B:
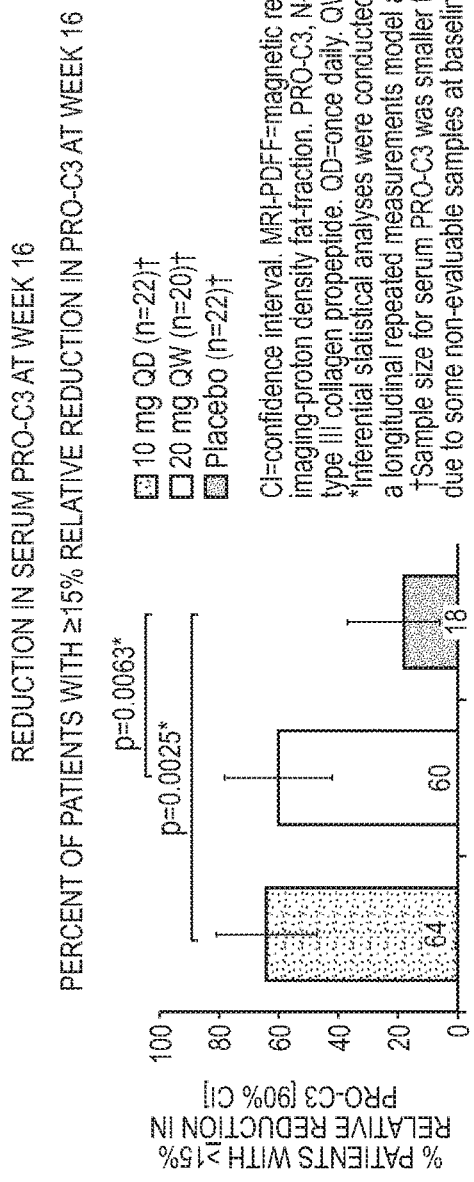

Pro-C3: At baseline, mean serum PRO-C3 levels were comparable across treatment groups, as shown in Table 3. Most patients (67% [28/42]) had baseline Pro-C3 levels of <20 ng/mL as shown in FIGS. 6A-6B. Patients treated with BMS-986036 10 mg QD and 20 mg QW had significantly reduced serum PRO-C3 levels compared with placebo (p<0.0001 and p=0.0093, respectively) at Day 112 from Baseline (see FIG. 7A). A maximal decrease was obtained at Day 57 for BMS-986036 10 mg QD groups and sustained for the rest of treatment period. There was no significant difference in the percent changes between BMS-986036 20 mg QW and BMS-986036 10 mg QD groups at Day 112. Furthermore, BMS-986036 10 mg QD and 20 mg QW groups compared with placebo had a significantly greater percentage of patients with a ≥15% relative reduction in serum PRO-C3 levels (QD: p=0.0025; QW: p=0.0063) (see FIG. 7B). 15% was chosen based on the precision of the assay. The percentages of subjects with ≥15% relative reduction were 64%, 60%, and 18%, for the BMS-986036 10 mg QD regimen, the BMS-986036 20 mg QW regimen, and the placebo regimen, respectively (Table 5). No difference in Pro-C3 response to treatment was observed by Baseline fibrosis stages.

TABLE 5

Change from Baseline at Week 16 - Pro-C3

| Percent Change from Baseline* at Week 16 | Number (%) of Subjects | | |
|---|---|---|---|
| | BMS 10 mg daily N = 25 | BMS 20 mg weekly N = 24 | Placebo daily N = 26 |
| Pro-C3 >=15% IMPROVEMENT | 14/22 (63.6) | 12/20 (60.0) | 4/22 (18.2) |
| 90% CI | (0.467, 0.805) | (0.419, 0.780) | (0.064, 0.369) |
| ODDS RATIO (90% CI) | 7.88 (2.46, 25.26) | 6.75 (2.08, 21.95) | |
| P-VALUE (ONE-SIDED) | 0.0025 | 0.0063 | |

*Baseline is defined as last non-missing result with a collection date-time less than the date-time of the first active dose of study medication. Fisher exact test is conducted for this analysis.

Adiponectin: Higher adiponectin levels are associated with improvements in steatosis, inflammation, and fibrosis. Significant increases in adiponectin were observed follow- ALT/AST: ALT and AST are biomarkers of liver injury. The mean absolute values of ALT and AST at Baseline and Week 16 are set forth in Table 6.

TABLE 6

Mean absolute values of ALT and AST at Baseline and Week 16

|  | Placebo (n = 26) | BMS-986036 10 mg QD (n = 25) | BMS-986036 20 mg QW (n = 24) |
|---|---|---|---|
| ALT, U/L, mean (SD) | | | |
| Baseline | 80 (51) | 66 (37) | 70 (33) |
| Week 16 | 73 (55)* | 39 (18)* | 47 (30)† |
| AST, U/L, mean (SD) | | | |
| Baseline | 58 (49) | 48 (23) | 52 (22) |
| Week 16 | 47 (29)* | 29 (11)* | 35 (12)† |

ALT = alanine aminotransferase. AST = aspartate aminotransferase. QD = once daily. QW = once weekly. SD = standard deviation.
*n = 24. †n = 22.

Figure 8A:
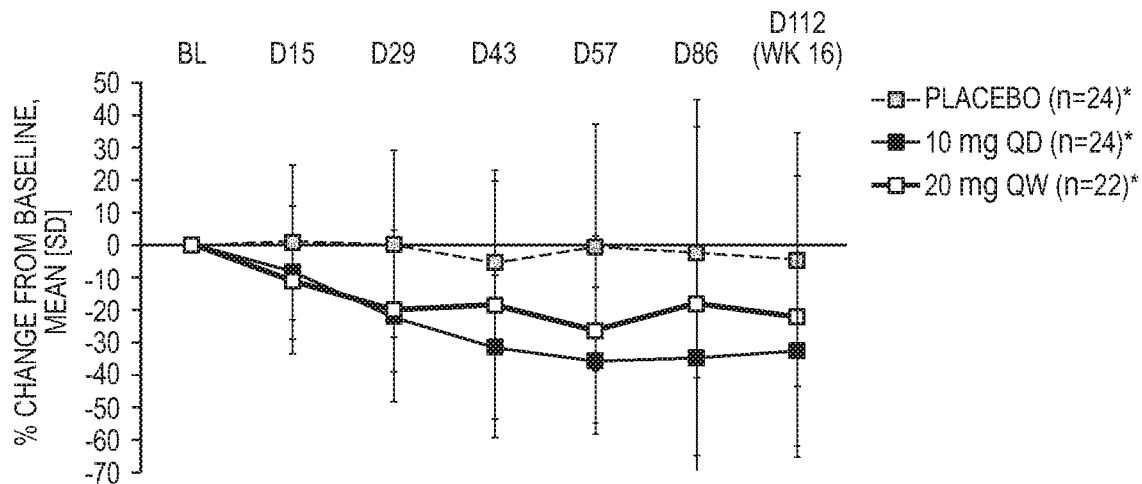
FIGS. 8A-8B show the changes in markers of liver injury at the end of treatment.
Figure 8B:
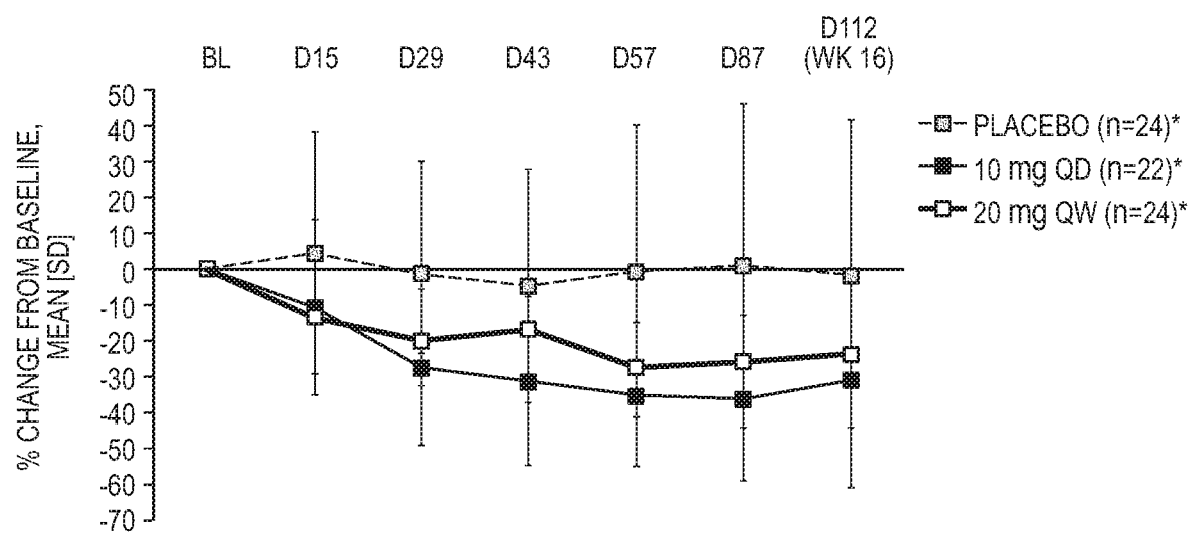

A robust decrease of ALT and AST was observed for both BMS-986036 dose groups starting from Day 29 (see FIGS. 8A-8B). A maximal decrease at Day 43 was observed for 10 mg QD group and at Day 57 for 20 mg QW group. A trend of more decrease was observed in 10 mg QD group compared to 20 mg QW group (see FIGS. 8A-8B). In both treatment groups, aminotransferase decreases were observed by Day 15 and a stable nadir was reached by Day 57; this nadir continued through the end of treatment. In the placebo group, ALT and AST did not change substantially from baseline.

Figure 9A:
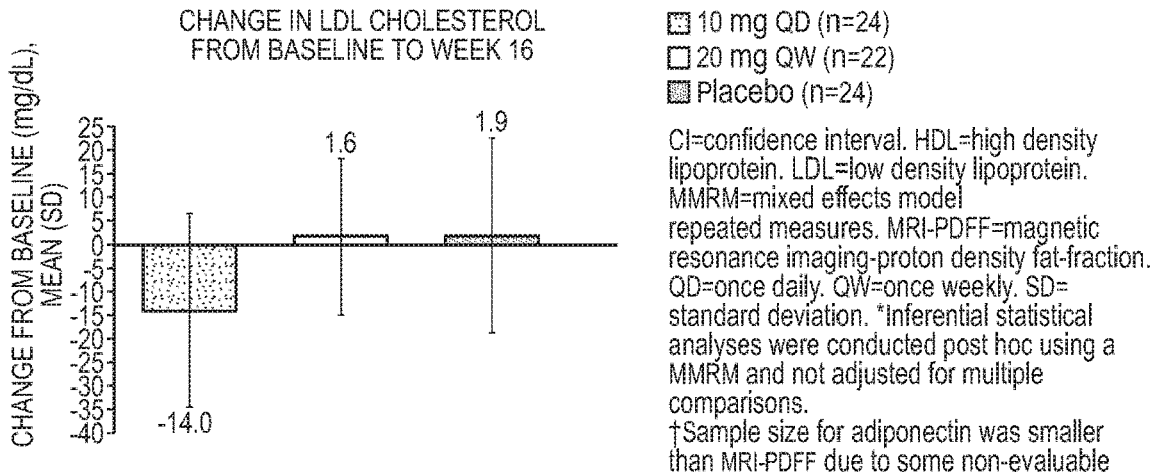
FIGS. 9A-9C show the change in LDL cholesterol (FIG. 9A), HDL cholesterol (FIG. 9B), and triglycerides (FIG. 9C) from baseline to Week 16.
Figure 9B:
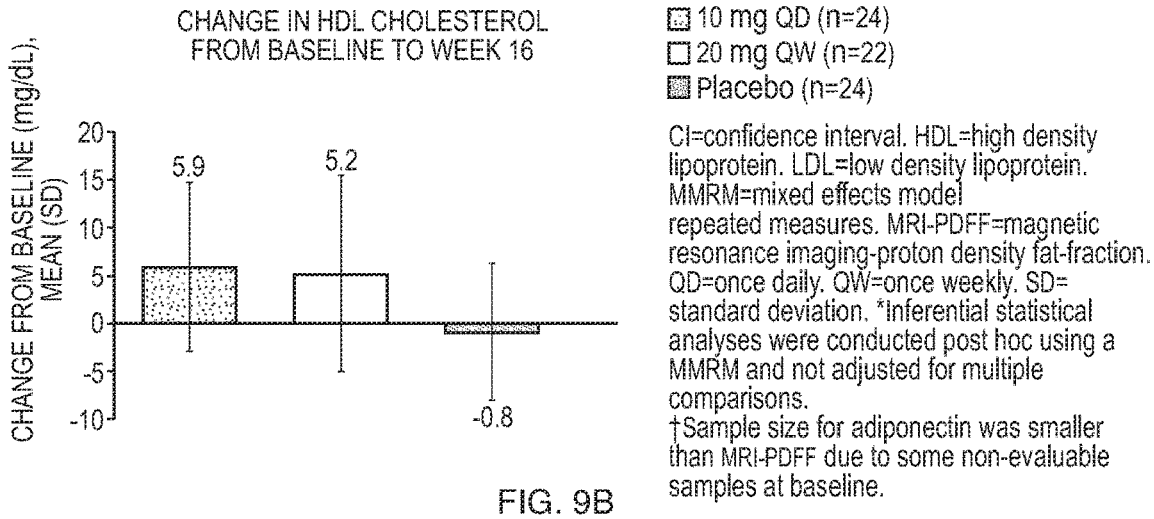
Figure 9C:
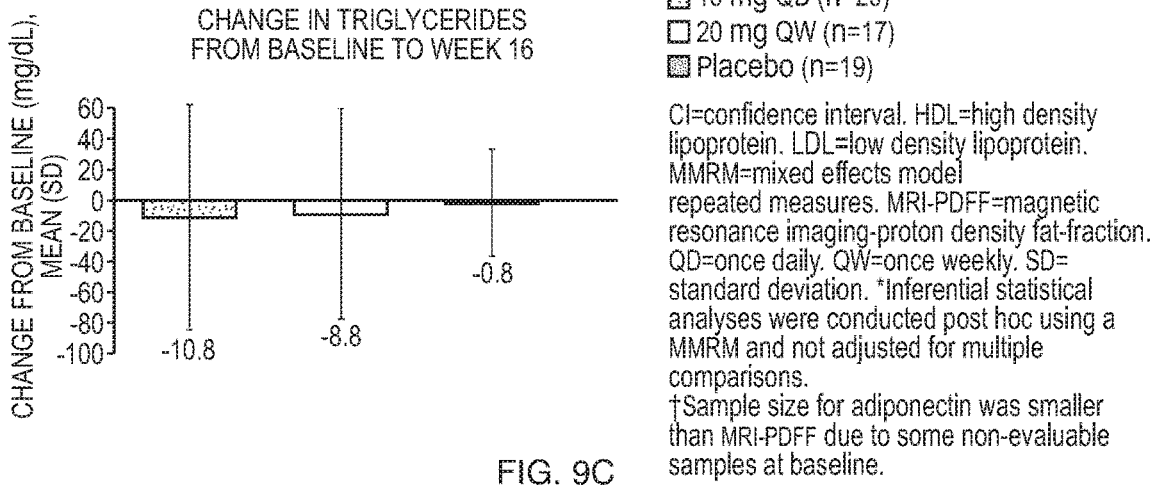

Fasting lipids: NASH is frequently associated with dyslipidemia. BMS 986036 at 10 mg QD and 20 mg QW resulted in improvements in TGs and HDL. HDL levels increased from Baseline for both 20 mg QW and 10 mg QD groups, while there was no changes in HDL for placebo (see FIG. 9B). In general, fasting triglyceride levels have high variability with large standard deviations. However, fasting triglyceride levels were decreased in both BMS-986036 dose groups compared to baseline, with mean levels decreased at Day 29 to Day 86, levels then trended upwards toward Baseline at Day 112 (see FIG. 9C). In addition, a decrease in LDL was observed for 10 mg QD group, while no significant decrease in LDL was observed for 20 mg QW and placebo groups (see FIG. 9A). Calculated Indices Related to NASH: Fibrosure fibrosis scores were reduced from Baseline in the BMS-986036 groups, while no reduction was observed in the placebo group.

BMS-986036 was generally well tolerated. There were no deaths or discontinuations due to adverse events, as set forth in Table 7.

TABLE 7

Safety Summary

| Event, n (%) | Placebo (n = 26) | BMS-986036 10 mg QD (n = 25) | BMS-986036 20 mg QW (n = 24) |
|---|---|---|---|
| Deaths | 0 | 0 | 0 |
| Discontinuation due to AEs | 0 | 0 | 0 |
| Serious AEs | 1 (4) | 1 (4) | 0 |
| Treatment-related SAEs | 0 | 0 | 0 |
| Overall AEs | 15 (58) | 18 (72) | 13 (54) |
| Most frequent AEs | | | |
| Diarrhoea | 2 (8) | 3 (12) | 5 (21) |
| Nausea | 2 (8) | 4 (16) | 3 (13) |
| Fatigue | 5 (19) | 1 (4) | 0 |
| Headache | 3 (12) | 1 (4) | 2 (8) |
| Urinary tract infection | 2 (8) | 1 (4) | 3 (13) |
| Frequent bowel movements | 0 | 5 (20) | 0 |
| Cough | 2 (8) | 1 (4) | 1 (4) |
| Injection site bruising | 0 | 2 (8) | 2 (8) |
| Grade 3 laboratory abnormalities of increased ALT* | 2 (8) | 1 (4) | 1 (4) |

AE = adverse event. ALT = alanine aminotransferase. SAE = serious adverse event.
*There were no grade 4 laboratory abnormalities observed.

Figure 10A:
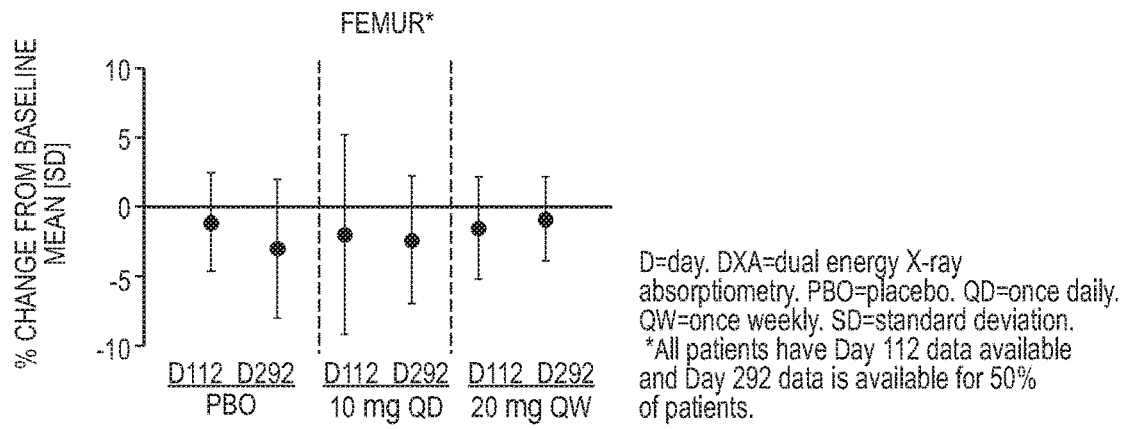
FIGS. 10A-10C show the bone mineral density measured by DXA at weeks 16 (D112) and 6 months post-treatment (D292) in the femur (FIG. 10A), hip (FIG. 10B), and spine (FIG. 10C).
Figure 10B:
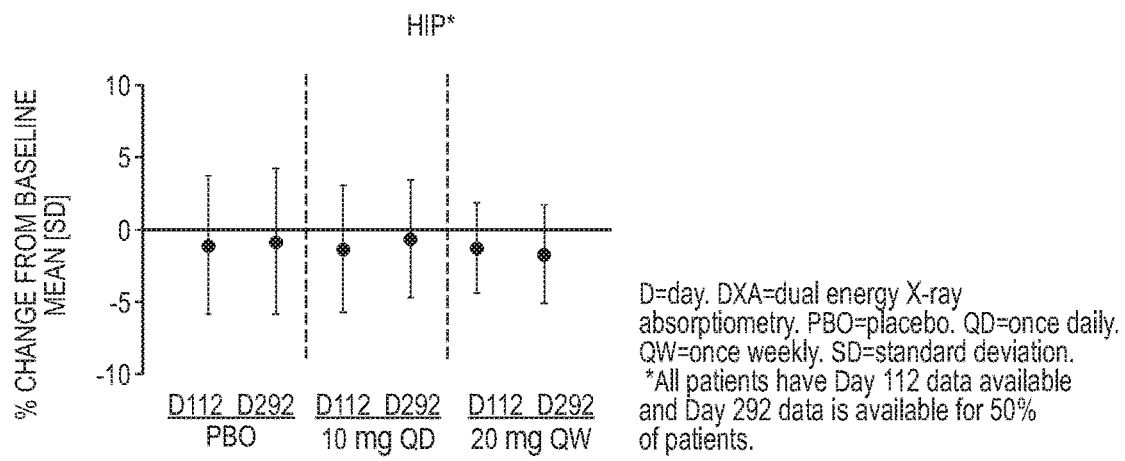
Figure 10C:
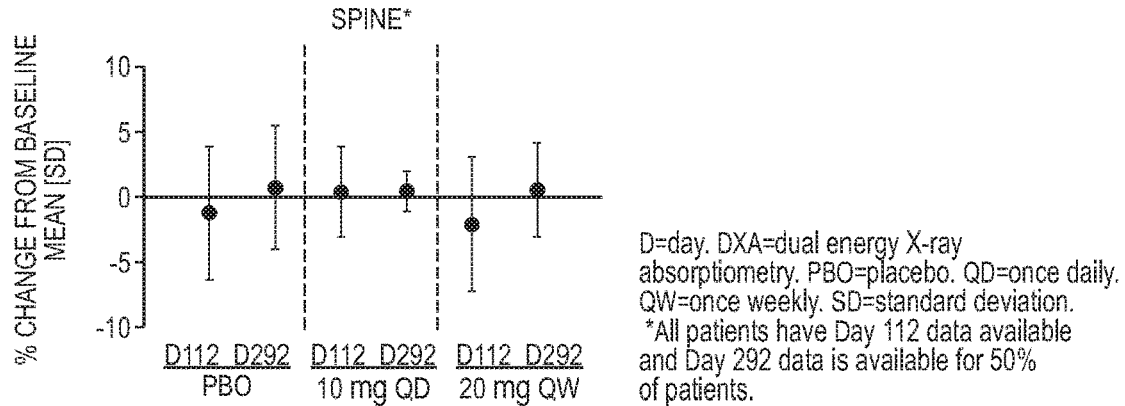

The most frequently reported AEs were diarrhoea (13%, [8/49 patients treated with either dose of BMS-986036 and 2/26 patients who received placebo]) and nausea (12%, [7/49 patients treated with either dose of BMS-986036 and 2/26 patients who received placebo]). There were 2 serious adverse events: one patient in the BMS-986036 10 mg QD group experienced worsened depression and attempted suicide, and one patient who was randomized to the placebo group received the wrong study drug during the placebo lead-in period. There were 28 adverse events among the following composite gastrointestinal AEs: diarrhoea, nausea, frequent bowel movements, upper abdominal pain, and vomiting. Of these 28 events, 11 were considered treatment-related. The frequency of gastrointestinal adverse events was higher in patients treated with BMS-986036 compared with patients who received placebo. However, there was no clear association between AE frequency and BMS-986036 dose. All gastrointestinal events were considered mild or moderate. Of the treatment-related gastrointestinal AEs, only 1/11 required treatment for resolution (1 patient who experienced frequent bowel movements was treated with *Bifidobacterium infantis*). Injection site bruising, erythema, or reactions were reported by 5%, 4%, and 3% of all patients, respectively. These events were mostly mild, transient, and did not require treatment. In total, 5 of 75 patients (7%) experienced a treatment-emergent grade 3 laboratory abnormality. There was 1 event of grade 3 high glucose (increase from grade 2 at baseline in a patient with T2DM treated with BMS-986036 20 mg QW) and 4 events of grade 3 ALT elevations (1 increase from grade 1 at baseline in a patient treated with BMS-986036 20 mg QW, 3 increases from grade 2 at baseline in 2 patients who received placebo and 1 patient who received BMS-986036 10 mg QD), which improved despite continued dosing. No grade 4 laboratory abnormalities were observed. No clinically relevant changes in ECG intervals or vital signs following treatment with BMS-986036 were observed. Mean BMDs of the femur (FIG. 10A), hip (FIG. 10B), and spine (FIG. 10C), as measured by DXA, were not meaningfully different in either BMS-986036 dose group compared with placebo at either Week 16 or 6 months after the end of treatment.

At time points up to study discharge on Day 142, anti-BMS-986036 and anti-FGF21 antibodies were detected in 62.5% (15/24) of patients treated with BMS-986036 20 mg QW and in 92% (23/25) of patients treated with BMS-986036 10 mg QD. Antibody titres were generally low (the majority were <64), and they were not associated with immune-related adverse events, injection site reactions, or changes in pharmacokinetic or pharmacodynamic profiles. At the time of post-study follow up visits that occurred 6 months after the end of treatment, <50% of patients had positive titres for anti-BMS-986036 and/or anti-FGF21 antibodies, and only one patient had an antibody titre >64.

C. Discussion

Compared with placebo, patients with NASH who were treated with 10 mg QD or 20 mg QW BMS-986036 had significantly decreased absolute hepatic fat fraction and significantly increased levels of adiponectin. Mean lipid values and markers of liver injury (ALT and AST) were decreased in the 10 mg QD and 20 mg QW groups compared with baseline values. Mean liver stiffness decreased in all treatment groups. In both the 10 mg QD and 20 mg QW groups, patients had significantly decreased levels of PRO-C3 (a biomarker of fibrosis) compared with placebo. Overall, the effects of daily and weekly dosing appear to be similar and treatment with either BMS-986036 dose was generally well tolerated.

In both BMS-986036 treatment groups, patients achieved a significant absolute reduction in hepatic fat fraction as measured by MRI-PDFF and over half of the patients achieved ≥30% relative reduction. In a previous study, histologic response (≥2-point reduction in NAS) was associated with a mean relative reduction in hepatic fat fraction of 29% as measured by MRI-PDFF (see Patel J, et al. Therap. Adv. Gastroenterol. 2016; 9(5): 692-701). These data, along with future histology-based analyses, further support the clinical utility of MRI-PDFF as a non-invasive method of evaluating steatosis in NASH patients.

Treatment with either dose of BMS-986036 was associated with significant improvements in adiponectin consistent with what has been previously reported in trials of other FGF21 analogues for patients with T2DM (see Gaich G, et al., *Cell. Metab.* 2013; 18(3): 333-40 and Talukdar S, et al., Cell Metab 2016; 23(3): 427-40). In patients with NASH, adiponectin levels can be at least 50% lower than in healthy individuals (see Pagano C, et al., *Eur. J. Endocrinol.* 2005; 152(1): 113-8), suggesting that adiponectin has important hepatic effects that are protective against NASH. Adiponectin knockout mice placed on a high fat diet have increased intrahepatic triglycerides, hepatocyte ballooning and fibrosis and adiponectin administration reduces steatosis, reduce inflammation, and has beneficial effects on lipid metabolism (see Asano T, et al., J Gastroenterol Hepatol 2009; 24(10): 1669-76 and Xu A, et al., J. Clin. Invest. 2003; 112(1): 91-100). Furthermore, adiponectin antagonizes hepatic stellate cell activation, a process critical to fibrogenesis, and it has anti-fibrotic effects in TGF-beta-stimulated fibroblasts and in mice with $CCl_4$-induced liver fibrosis (see Shafiei M S et al., Am J Pathol 2011; 178(6): 2690-9; Fang F, et al., Arthritis Res Ther 2012; 14(5): R229; and Kumar P, et al., PLoS One 2014; 9(10): e110405).

Approximately 1/3 of patients in the 10 mg QD and 20 mg QW groups achieved ≥15% relative reduction in liver stiffness as measured by MRE, a non-invasive imaging technique. A 15% relative reduction in liver stiffness measured by MRE has been associated with significant reduction in serum markers of fibrosis (see Loomba R, et al., J Hepatol 2017; 66(Suppl 1): S671). While the small sample size limits the interpretability of these results, it is encouraging that this threshold can be reached with a relatively short treatment duration. MRE is a promising imaging biomarker of fibrosis. It is reproducible and has a high rate of technical success.

At Week 16, BMS-986036-treated patients also had significantly decreased levels of PRO-C3, a measure of type III collagen formation, compared with placebo. In patients with NASH, the levels of PRO-C3 have been associated with NASH disease activity and fibrosis stage (see Leeming D J, et al., J Hepatol 2017; 66(Suppl 1): S154 and Leeming D J, et al., Plasma collagen III type III (PRO-C3) levels associate with severity of histological features of non-alcoholic steatohepatitis and fibrosis within the screening population from the CENTAUR study. NASH Biomarkers Workshop 2017 2017; Presented on Saturday, May 5, 2017). In patients with chronic hepatitis C virus infection, PRO-C3 has been shown to correlate with the severity of liver fibrosis, and high baseline PRO-C3 levels have been associated with increased fibrotic disease progression (see Nielsen M J, PLoS One 2015; 10(9): e0137302). The serum PRO-C3 assay provides an accurate, non-invasive method to identify anti-fibrotic treatment response (see Karsdal M A, et al., Am J Physiol Gastrointest Liver Physiol 2016; 311(6): G1009-17). Furthermore, longitudinal decreases in PRO-C3 have been correlated with improvements in hepatic fibrosis, as assessed by biopsy (see Luo Y., et al., J Hepatol 2017; 66(Suppl 1): S676). Given the above, the reduction in PRO-C3 observed in BMS-986036-treated patients seems to be indicative of an anti-fibrotic treatment effect.

In this study, no substantial changes in body weight were observed in patients with NASH after 16-week treatment with BMS-986036. Although FGF21-induced weight loss has been shown in animal studies, the absence of weight loss in humans is consistent with observations from a previous trial of BMS-986036 in obese patients with T2DM (see Kharitonenkov A, et al., Endocrinology 2007; 148(2): 774-81; Coskun T, et al., Endocrinology 2008; 149(12): 6018-27; Xu J, et al., Am J Physiol Endocrinol Metab 2009; 297(5): E1105-14; Charles E, et al., Hepatology 2016; 64(Suppl 1): 17A). The reason for the differences in weight loss in animal studies versus clinical trials is unclear. However, there may be a distinct difference in the FGF21 physiology of humans versus rodents and non-human primates.

Overall, daily or weekly doses of BMS-986036 were generally safe and well tolerated, with no deaths, treatment-related serious adverse events, or discontinuations due to injection burden or AEs. The most frequently reported adverse events were gastrointestinal in nature (diarrhoea and nausea), which is consistent with previous observations in other studies of FGF21 analogues (see Talukdar S, et al., Cell Metab 2016; 23(3): 427-40 and Fang F, et al., Arthritis Res Ther 2012; 14(5): R229). These adverse events were generally mild and did not require treatment. Similarly, injection site reactions were mostly mild, transient, and did not require treatment. In contrast to a recent study of an intravenously administered, long-acting FGF21 analog, no obvious changes in heart rate or blood pressure were observed with BMS-986036 treatment; this is consistent with results from the BMS-986036 first-in-human study in which these parameters were intensively monitored (see Kim A M, Somayaji V R, Dong J Q, et al., Diabetes Obes Metab 2017; 19(12): 1762-72 and Charles E, et al., Hepatology 2016; 64(Suppl 1): 546A). In animal models, FGF21 administration has been associated with changes in BMD (see Wei W, et al., Proc Natl Acad Sci USA 2012; 109(8): 3143-8). However, in this study, mean BMD (determined by DXA) did not meaningfully change for either BMS-986036 treatment group, compared with placebo, from baseline through the end of treatment, or through 6 months of follow-up.

Given that BMS-986036 is a pegylated human FGF21 mimetic, the potential exists that it may elicit immunogenic responses in some patients. Immunogenicity studies showed that anti-BMS-986036 and anti-FGF21 antibodies were detectable in over half of the patients treated with BMS-986036 20 mg QW and in over 90% of patients treated with BMS-986036 10 mg QD. These antibody titres were generally low, were not associated with immune-related adverse events or injection site reactions, and were declining in many patients by the time of follow-up visits. There was no evidence to suggest breakage in immune tolerance to endogenous FGF21 since titres to endogenous FGF21 antibodies decreased after discontinuation of treatment. Together, these data suggest that BMS-986036 does not elicit clinically meaningful immunogenicity when administered QD or QW over a 16-week period.

The major findings of this study further extend knowledge gained from with an earlier 12-week, phase 2 trial of BMS-986036 in obese T2DM patients (MB130-002) (see Charles E, Neuschwander-Tetri B, et al., Hepatology 2016; 64(Suppl 1): 17A). Obesity and T2DM are two major risk factors for the development of NAFLD, including NASH. In MB130-002, most patients were likely to have underlying NAFLD. 97% of patients had a Fatty Liver Index (FLI) ≥60, a cutoff indicative of the presence of fatty liver (see Bedogni G, et al., BMC Gastroenterol 2006; 6: 33). In these patients, BMS-986036 also improved lipids, adiponectin and PRO-C3 levels. Importantly, the safety profile of BMS-986036 was comparable in MB130-002 and the instant study, and it was characterized by an increased frequency of predominantly mild gastrointestinal symptoms, no instances of drug-induced liver injury, no clinically meaningful changes in ECG or vital signs, and no apparent effect on bone density (as measured by DXA) over a 16-week time period. Taken together, data suggest that BMS-986036 treatment is well tolerated and has positive effects on liver and metabolic parameters in patients with NASH, as well as in patients with risk factors for NASH. In summary, BMS-986036 was generally safe and well tolerated when administered by SC injection at doses of BMS-986036 20 mg QW or BMS-986036 10 mg QD for 16 weeks in NASH subjects. Results suggest that BMS-986036 has beneficial effects on steatosis, liver injury, and fibrosis in NASH: Both BMS-986036 10 mg QD and BMS-986036 20 mg QW regimens, compared with placebo, significantly reduced hepatic fat fraction at Week 16. Relative to placebo, BMS-986036 QD and QW were associated with improvements in biomarkers of fibrosis (MRE and Pro-C3), metabolic parameters (adiponectin and lipids), and markers of hepatic injury (ALT and AST). Improvements in MRI-PDFF, Pro-C3, LDL, ALT, and AST exhibited dose-dependence. For each marker (except for LDL), the majority of the maximally observed treatment effect difference was achieved with BMS-986036 20 mg QW. Ctrough of BMS-986036 (C-terminal intact and Total) was higher for 10 mg QD relative to 20 mg QW. Ctrough levels remained stable after the steady state achieved.

Example 2: Baseline Serum Pro-C3 Predicts Response to BMS-986036: A Secondary Analysis of a Multi-Center Clinical Trial in NASH The objective of this post hoc analysis of the clinical trial from Example 1 was to assess Baseline predictors of treatment response to BMS-986036.

Post hoc analyses assessed the relationship between Baseline characteristics and changes in markers of metabolism, steatosis, liver injury, and fibrosis. Evaluations included type 2 diabetes mellitus (T2DM) status, liver biopsy grade (NAFLD Activity Score [NAS]) and fibrosis stage (NASH CRN criteria) and serum Pro-C3 levels (≥20 vs<20 ng/mL). Hepatic and metabolic markers were evaluated at Baseline and Week 16 and included liver fat (MRI-PDFF), liver stiffness (MRE) and serum biomarkers: Pro-C3, ALT, AST, adiponectin, LDL, HDL, hyaluronic acid (HA), PAI-1, and CK-18 (cytokeratin-18). For the purposes of this analysis, BMS-986036 groups (20 mg QW [n=23] vs 10 mg QD [n=25]) were combined, and placebo group (n=26) was analyzed separately. Statistical comparisons were made using Kruskal-Wallis tests.

Figure 11A:
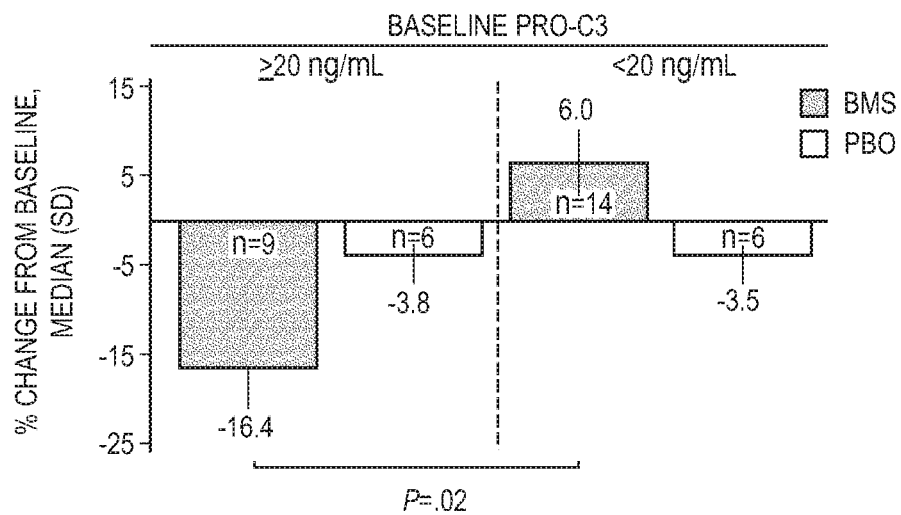
FIGS. 11A-11B show the change in MRE (FIG. 11A) and Pro-C3 (FIG. 11B) at week 16 in patients stratified by baseline Pro-C3 (>=20 ng/ML and <20 ng/ML).
Figure 11B:
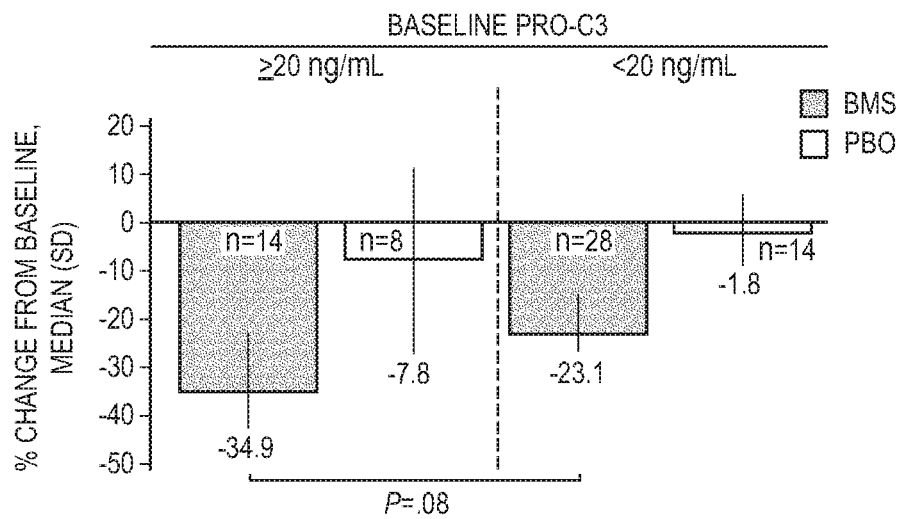
Figure 12A:
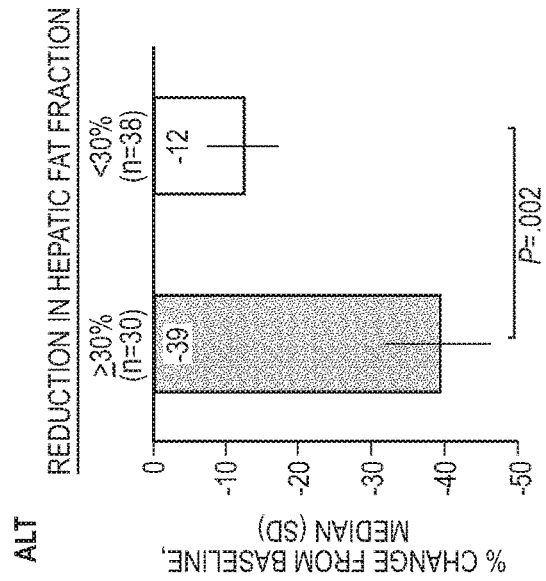
FIGS. 12A-12D show the changes in Pro-C3 (FIG. 12A), ALT (FIG. 12B), AST (FIG. 12C), and CK-18 (FIG. 12D) at week 16 in patients stratified by reduction in hepatic fat fraction.
Figure 12B:
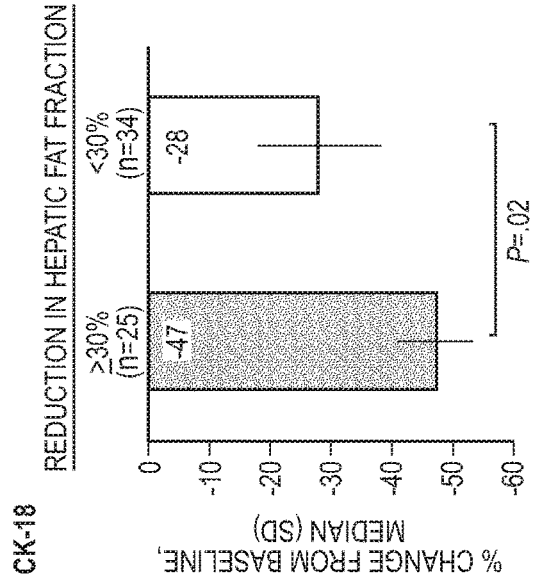
Figure 12C:
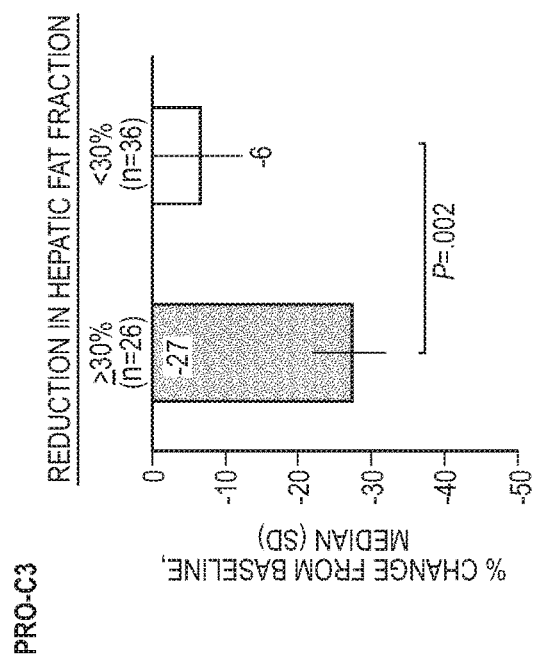
Figure 12D:
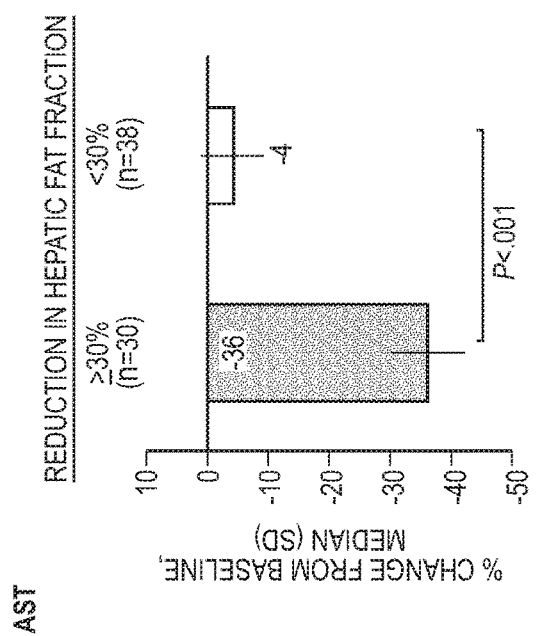

Mean baseline Pro-C3 levels were generally consistent across BMS-986036 treatment groups, in which most patients (67%, [28/42]) had baseline Pro-C3 levels of <20 ng/mL. In BMS-986036-treated patients (n=48), Baseline serum Pro-C3 level ≥20 ng/mL, compared with <20 ng/mL, was associated with greater reduction in MRE (median % change: −16.4% vs 6.0%, P=0.0198) and greater decreases in Pro-C3 levels (median % change: −34.9% vs −23.1%, P=0.08) (FIG. 11A-11B). Baseline Pro-C3 levels did not predict BMS-986036-treatment response assessed via other hepatic or metabolic biomarkers. Other Baseline characteristics, including T2DM status, NAS, or fibrosis stage did not clearly impact biomarker responses in BMS-986036-treated patients. In the placebo group, no Baseline characteristics, including Pro-C3 levels, were clearly associated with differences in the biomarker responses evaluated.

In this Phase 2 clinical trial in NASH, high Baseline Pro-C3 levels were associated with improvements in biomarkers of fibrosis and liver stiffness (Pro-C3 and MRE) in BMS-986036-treated patients. Conversely, other Baseline characteristics, including fibrosis severity, did not appear to predict response to BMS-986036 treatment. These results support the use of serum Pro-C3 as a predictor for treatment response to BMS-986036 and as a potential surrogate marker to identify the ideal NASH patients for treatment.

Figure 13A:
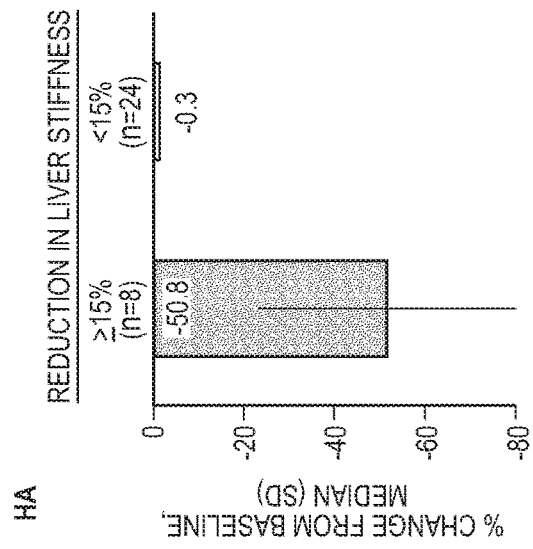
FIGS. 13A-13C show the changes in Pro-C3 (FIG. 13A), HA (FIG. 13B), and HDL (FIG. 13C) at week 16 in patients stratified by reduction in liver stiffness.
Figure 13B:
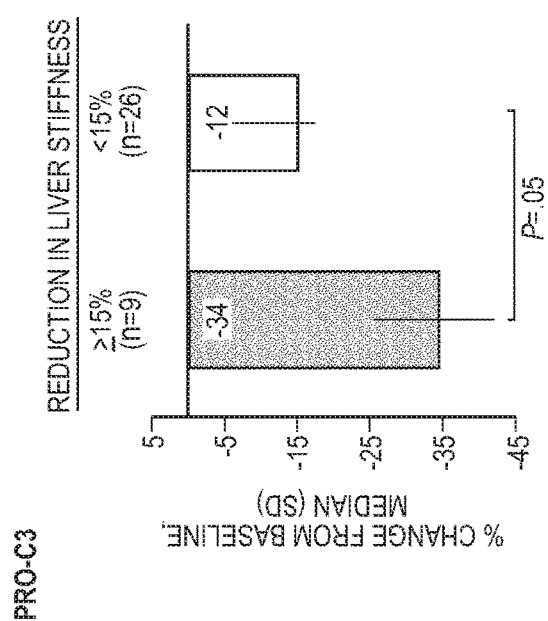
Figure 13C:
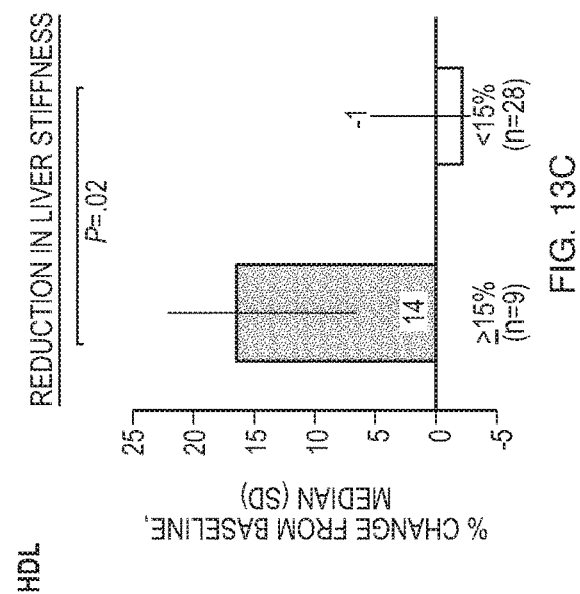

On the other hand, patients with a reduction in hepatic fat fraction ≥30% versus patients with <30% had significantly greater decreases in Pro-C3, ALT, AST, and CK-18 (FIGS. 12A-12D). In addition, a reduction in liver stiffness of ≥15% compared with reduction <15% was associated with decrease in Pro-C3, HA and increase in HDL (FIGS. 13A-13C).

| SEQUENCE SUMMARY | |
|---|---|
| SEQ ID NO: | SEQUENCE |
| SEQ ID NO: 1 (corresponding to SEQ ID NO: 1 of US Pat. No. 9,079,971) | HPIPDSSPLLQFGGQVRQRYLYTDDAQQTEAHLEIREDGTVGGAAD QSPESLLQLKALKPGVIQILGVKTSRFLCQRPDGALYGSLHFDPEACS FRELLLEDGYNVYQSEAHGLPLHLPGNKSPHRDPAPRGPARFLPLPG LPPAPPEPPGILAPQPPDVGSSDPLSMVGPSQGRSPSYAS |

SEQUENCE SUMMARY

| SEQ ID NO: | SEQUENCE |
|---|---|
| SEQ ID NO: 2 (corresponding to SEQ ID NO: 201 of US Pat. No. 9,434,778) | MHPIPDSSPLLQFGGQVRQRYLYTDDAQQTEAHLEIREDGTVGGAA DQSPESLLQLKALKPGVIQILGVKTSRFLCQRPDGALYGSLHFDPEA CSFRELLLEDGYNVY(pAF)SEAHGLPLHLPGNKSPHRDPAPRGPARF LPLPGLPPAPPEPPGILAPQPPDVGSSDPLSMVGPSQGRSPSYAS |

What is claimed is:

1. A method for treating a patient having NASH, wherein the patient has a serum Pro-C3 level greater than 20 ng/ML prior to treatment, the method comprising administering to the patient a modified Fibroblast growth factor 21 (FGF-21) in an amount and with a frequency sufficient to treat NASH, wherein the modified FGF-21 comprises the polypeptide of SEQ ID NO:1, except that an amino acid in the polypeptide is substituted by a non-naturally encoded amino acid, wherein: (a) said non-naturally encoded amino acid is at a position corresponding to residue 108 of SEQ ID NO:1; and (b) said non-naturally encoded amino acid comprises para-acetyl phenylalanine linked to a polymer comprising a poly(ethylene glycol).

2. A method for treating a patient having NASH comprising:
    (1) obtaining or having obtained a blood sample from the patient prior to treatment,
    (2) determining or having determined a serum Pro-C3 level in the blood sample that is greater than 20 ng/ML prior to treatment, and
    (3) administering to the patient a modified Fibroblast growth factor 21 (FGF-21) in an amount and with a frequency sufficient to treat NASH after a serum Pro-C3 level has been determined, wherein the modified FGF-21 comprises the polypeptide of SEQ ID NO:1, except that an amino acid in the polypeptide is substituted by a non-naturally encoded amino acid, wherein: (a) said non-naturally encoded amino acid is at a position corresponding to residue 108 of SEQ ID NO:1; and (b) said non-naturally encoded amino acid comprises para-acetyl phenylalanine linked to a polymer comprising a poly(ethylene glycol).

3. The method of claim 1 or 2, wherein the serum Pro-C3 level prior to administration to the patient of a modified Fibroblast growth factor 21 (FGF-21) is greater than about 21 ng/ML, 22 ng/ML, 23 ng/ML, 24 ng/ML, or 25 ng/ML.

4. The method of claim 1 or 2, wherein the Pro-C3 level or levels are measured by using an immunoassay, immunochemistry, immunohistochemistry assay, nucleoprobe assay, in situ hybridization, fluorescent RNA probes, RT-PCR, microarray transcription assay, or RNA transcription assay.

5. The method of claim 4, wherein the immunoassay is an enzyme-linked immunosorbent assay (ELISA) or a radioimmunoassay (RIA).

6. The method of claim 1 or 2, wherein said poly(ethylene glycol) has an average molecular weight of about 30 kDa.

7. The method of claim 1 or 2, wherein said non-naturally encoded amino acid is linked to said polymer through an oxime linkage.

8. The method of claim 1 or 2, wherein the modified FGF-21 comprises SEQ ID NO:2.

9. The method of claim 1 or 2, wherein the modified FGF-21 is administered at a once weekly dose of 20 mg or a once daily dose of 10 mg.

10. The method of claim 1 or 2, comprising administration of a second therapeutic agent.

11. The method of claim 1 or 2, wherein the treatment:
   (a) results in a decrease in serum Pro-C3 levels in the patient;
   (b) produces a shift toward normal serum levels of Pro-C3 in the patient;
   (c) results in a reduction in liver stiffness in the patient compared to the patient's liver stiffness prior to treatment, wherein liver stiffness is assessed by magnetic resonance elastography (MRE); and/or
   (d) results in a reduction in hepatic fat fraction in the patient compared to the patient's hepatic fat fraction prior to treatment, wherein hepatic fat fraction is as assessed by magnetic resonance imaging-estimated proton density fat fraction (MRI-PDFF).

12. The method of claim 11, wherein the treatment with the modified FGF-21 results in a 15% or greater reduction in liver stiffness in the patient compared to the patient's liver stiffness prior to treatment, wherein liver stiffness is assessed by MRE.

13. The method of claim 11, wherein the treatment with the modified FGF-21 results in a 30% or greater reduction in hepatic fat fraction in the patient compared to the patient's hepatic fat fraction prior to treatment, wherein hepatic fat fraction is assessed by MRI-PDFF.

14. The method of claim 1 or 2, wherein the treatment with the modified FGF-21 results in a reduction in liver stiffness in the patient compared to the patient's liver stiffness prior to treatment, and a decrease in serum Pro-C3 levels in the patient compared to the patient's serum Pro-C3 levels prior to treatment, wherein liver stiffness is assessed by magnetic resonance elastography (MRE).

15. The method of claim 1 or 2, wherein the treatment produces at least one therapeutic effect in the patient selected from the group consisting of a reduction or cessation in fatigue, malaise, weight loss, and/or right upper quadrant abdominal discomfort.

16. A method of identifying a patient having Nonalcoholic Steatohepatitis (NASH) that is suitable for treatment with a modified FGF-21, wherein the patient is identified as having NASH that is suitable for treatment with the modified FGF-21 if a serum Pro-C3 level in a blood sample from the patient is greater than 20 ng/ML prior to treatment, wherein the modified FGF-21 comprises the polypeptide of SEQ ID NO:1, except that an amino acid in the polypeptide is substituted by a non-naturally encoded amino acid, wherein: (a) said non-naturally encoded amino acid is at a position corresponding to residue 108 of SEQ ID NO:1; and (b) said non-naturally encoded amino acid comprises para-acetyl phenylalanine linked to a polymer comprising a poly(ethylene glycol).

* * * * *

SEQUENCE LISTING

<160> NUMBER OF SEQ ID NOS: 3

<210> SEQ ID NO 1
<211> LENGTH: 181
<212> TYPE: PRT
<213> ORGANISM: Homo sapiens

<400> SEQUENCE: 1

```
His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180
```

<210> SEQ ID NO 2
<211> LENGTH: 182
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: MOD_RES
<222> LOCATION: (109)..(109)
<223> OTHER INFORMATION: Para-acetyl phenylalanine

<400> SEQUENCE: 2

```
Met His Pro Ile Pro Asp Ser Ser Pro Leu Leu Gln Phe Gly Gly Gln
1               5                   10                  15
```

```
Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Xaa Ser Glu Ala
            100                 105                 110

His Gly Leu Pro Leu His Leu Pro Gly Asn Lys Ser Pro His Arg Asp
            115                 120                 125

Pro Ala Pro Arg Gly Pro Ala Arg Phe Leu Pro Leu Pro Gly Leu Pro
        130                 135                 140

Pro Ala Pro Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
                180

<210> SEQ ID NO 3
<211> LENGTH: 10
<212> TYPE: PRT
<213> ORGANISM: Homo sapiens

<400> SEQUENCE: 3

Cys Pro Thr Gly Pro Gln Asn Tyr Ser Pro
1               5                   10
```